US006914124B2

(12) United States Patent
Bujard et al.

(10) Patent No.: US 6,914,124 B2
(45) Date of Patent: Jul. 5, 2005

(54) TETRACYCLINE-REGULATED TRANSCRIPTIONAL ACTIVATOR FUSION PROTEINS

(75) Inventors: Hermann Bujard, Heidelberg (DE); Manfred Gossen, El Cerrito, CA (US)

(73) Assignee: TET Systems Holding GmbH & Co. KG, Heidelberg (DE)

( * ) Notice: Subject to any disclaimer, the term of this patent is extended or adjusted under 35 U.S.C. 154(b) by 288 days.

(21) Appl. No.: 09/777,317

(22) Filed: Feb. 5, 2001

(65) Prior Publication Data

US 2002/0086426 A1 Jul. 4, 2002

Related U.S. Application Data

(63) Continuation of application No. 09/163,276, filed on Sep. 29, 1998, now abandoned, which is a continuation of application No. 08/479,306, filed on Jun. 7, 1995, now Pat. No. 5,888,981, which is a continuation-in-part of application No. 08/260,452, filed on Jun. 14, 1994, now Pat. No. 5,650,298, which is a continuation-in-part of application No. 08/076, 327, filed on Jun. 14, 1993, now abandoned.

(51) Int. Cl.$^7$ .............................................. C07K 14/00
(52) U.S. Cl. ...................................................... 530/350
(58) Field of Search ........................................ 530/350

(56) References Cited

U.S. PATENT DOCUMENTS

| | | | | |
|---|---|---|---|---|
| 4,833,080 A | 5/1989 | Brent et al. | ............... | 435/172.3 |
| 5,221,778 A | 6/1993 | Byrne et al. | .................... | 800/2 |
| 5,464,758 A | 11/1995 | Gossen et al. | ............. | 435/69.1 |
| 5,545,808 A | 8/1996 | Hew et al. | ....................... | 800/2 |
| 5,595,895 A | 1/1997 | Miki et al. | ................ | 435/172.3 |
| 6,136,954 A | * 10/2000 | Bujard et al. | ................ | 530/350 |

FOREIGN PATENT DOCUMENTS

| | | |
|---|---|---|
| EP | 0 332 416 | 9/1989 |
| EP | 0 455 424 A2 | 11/1991 |
| EP | 0 455 687 B1 | 11/1991 |
| EP | 0 494 724 A2 | 7/1992 |
| WO | WO 91/13979 | 9/1991 |
| WO | WO 91/19784 | 12/1991 |
| WO | WO 91/19796 | 12/1991 |
| WO | WO 92/11874 | 7/1992 |
| WO | WO 92/20808 | 11/1992 |
| WO | WO 93/04169 | 3/1993 |
| WO | WO 93/23431 | 11/1993 |
| WO | WO 94/04672 | 3/1994 |
| WO | WO 94/18317 | 8/1994 |
| WO | WO 94/29442 | 12/1994 |
| WO | WO 96/01313 | 1/1996 |

OTHER PUBLICATIONS

Ackland–Berglund, C.E. and Leib, D.A. (1995) *BioTechniques 19*:216–217.
Ackland–Berglund, C.E. and Leib, D.A. (1995) "Efficacy of Tetracycline–Controlled Gene Expression Is Influenced by Cell Type" *BioTechniques 18(2)*:196–200.

Agarwal, M.L. et al. (1995) "p53 Controls Both the $G_2$/M and the $G_1$ Cell Cycle Checkpoints and Mediates Reversible Growth Arrest in Human fibroblasts," *Proceedings of the National Academy of Science, Sci USA, 92*:8493–8497.

Altschmied, L. et al. (1988) "A threonine to alanine exchange at position 40 of Tet repressor alters the recognition of the sixth base pair of tet operator from GC to AT", *The EMBO Journal, 7(12)*:4011–4017.

Baim, S.B. et al. (1991) "A chimeric mammalian transactivator based on the lac repressor that is regulated by temperature and isopropyl β–D–thiogalactopyranoside", *Proceedings of the National Academy of Science 88*: 5072–5076.

Baniahmad, A. et al. (1991) "A Transferable Silencing Domain Is Present In the Thyroid Hormone Receptor, In the v–erbA Oncogene Product and In the Retinoic Acid Receptor" *The EMBO Journal 11(3)*:1015–1023.

Baumeister, R. et al. (1992) "Tet Repressor Tet Interactions Derived From Mutants With New Recognition Specificities", *Structural Tools For The Analysis Of Proten–Nucleic Acid Complexes Advances in Life Sciences*, Birkhauser, Basel ;Boston, pp. 175–183.

Baumeister, R. et al., (1992) "Contacts Between Tet Repressor And Tet Operator Revealed By New Recognition Specificities Of Single Amino Acids Replacement Mutants", *Journal Of Molecular Biology, 226*:1257–1270.

Baumeister, R. et al. (1992) Functional Roles of Amino Acid Residues Involved In Forming THE.Alpha.–helix–turn–.alpha.–helix operator DNA Binding Motif Of Tet repressor From Th10, *Proteins: Structure, Function, and Genetics, 14(2)*:168–177.

(Continued)

Primary Examiner—Ram R. Shukla
(74) Attorney, Agent, or Firm—Lahive & Cockfield LLP; DeAnn F. Smith

(57) ABSTRACT

A method for regulating expression of a tet operator-linked gene in a cell of a subject is disclosed. In one embodiment, the method involves introducing into the cell a nucleic acid molecule encoding a tetracycline-controllable transactivator (tTA), the tTA comprising a Tet repressor operably linked to a polypeptide which directly or indirectly activates transcription in eucaryotic cells; and modulating the concentration of a tetracycline, or analogue thereof, in the subject. Alternatively, in another embodiment, the method involves obtaining the cell from the subject, introducing into the cell a first nucleic acid molecule which operatively links a gene to at least one tet operator sequence, introducing into the cell a second nucleic acid molecule encoding a tTA, to form a modified cell, administering the modified cell to the subject, and modulating the concentration of a tetracycline, or analogue thereof, in the subject. The first and second nucleic acid molecule can be within a single molecule (e.g., in the same vector) or on separate molecules.

5 Claims, 32 Drawing Sheets

OTHER PUBLICATIONS

Bergman, M. et al. (1995) "Overexpressed Csk Tyrosine Kinase Is Localized in Focal Adhesions, Causes Reorganization of $\alpha_v\beta_5$ Integrin, and Interferes with HeLa Cell Spreading", *Molecular and Cellular Biology,* 15(2):711–722.

Boshart, M. et al. (1985) "A Very Strong Enhancer Is Located Upstream of an Immediate Early Gene of Human Cytomegalovirus", *Cell* 41(2):521–530.

Bradley, A. (1991) "Modifying the mammalian genome by genet targeting", *Current Opinion in Biotechnology* 2:832–829.

Bradley, A. (1992) "Modifying The Mouse: Design And Desire", *Biotechnology,* 10:534–539.

Brent, R. and M. Ptashne (1984) "A Bacterial Repressor Protein or a Yeast Transcriptonal Terminator Can Block Upstream Activation of A Yeast Gene" *Nature* 312:612–615.

Brent R. and M. Ptashne (1985) "A Eukaryotic Transcriptional Activator Bearing the DNA Specificity of a Prokaryotic Repressor" *Cell* 43:729–736.

Brown, M., et al. (1987) "lac Repressor Can Regulate Expression from a Hybrid SV40 Early Promoter Containing a lac Operator in Animal Cells", *Cell* 49:603–612.

Buckbinder L. et al. (1994) "Gene Regulation by Temperature–Sensitive p53 Mutants: Identification of p53 response genes" *Proc. Natl. Acad. Sci. USA* 91:10640–10644.

Capecchi, M.R. (1989) "Altering the Genome by Homologous Recombination", *Science* 244:1288–1292.

Cayrol, C. et al. (1995) "Identification of Cellular Target Genes of the Epstein–Barr Virus Transactivator Zta: Activation of Transforming Growth Factor $\beta$igh3 (TGF–$\beta$igh3) and TGF–$\beta$1", *Journal of Virology,* 69(7):4206–4212.

Chen, Y.Q. et al. (1995) "Tumor Suppression by p21$^{WAF11}$", *Cancer Research,* 55:4536–4539.

Coghlan, A. (1995) "Gene drream fades away" *New Scientist* 148:14–15.

Courey, A.J. and Tjian, R., (1988) "Analysis of Sp1 In Vivo Reveals Multiple Transcriptional Domains, Including a Novel Glutamine–Rich Activation Motif", *Cell* 55:887–898.

Cowell, (1994) "Repression versus activation in the control of gene transcription," *Trends in Biochemical Sciences,* 19:1, 38–42.

Crystal, R.G. (1995) "Transfer of Genes to Humans: Early Lessons and Obstacles to Success", *Science* 270:404–410.

Daddona et al. (1984) "Human Adenosine Deaminase." *J. Biol. Chem.* 259:12101–12106.

Damke, H. et al. (1994) "Induction of Mutant Dynamin Specifically Blocks Endocytic Coated Vesicle Formation," *The Journal of Cell Biology* 127(4):915–934.

Damke, H. et al. (1995) "Tightly Regulated and Inducible Expression of Dominany Intefering Dynamin Mutant in Stably Transformed HeLa Cells." *Methods in Enzymology* 257:209–220.

Degenkolb, J. et al. (1991) "Sructural Requirements of Tetracycline–Tet Repressor Interaction: Determination of Equilibrium Binding Constants for Tetracycline Analogs with the Tet Repressor" *Antimicrobial Agents and Chemotherapy* 35(8):1591–1595.

Deuschle, u., et al. (1989) "Regulated expression of foreign genes in mammalian cells under the control of coliphage T3 RNA polymerase and lac repressor", *Proceedings of the National Academy of Science USA* 86:5400–5404.

Deuschle et al. (1995) "Tetracycline–reversible silencing of eukaryotic promoters," *Mol. Cell. Biol.,* 15:4, 1907–1914.

Dhawan, J. et al. (1995) "Tetracyclin–Regulated Gene Expression Follwing Direct Gene Transfer into Mouse Skeletal Muscle", *Somatic Cell and Molecular Genetics,* 21(4):233–240.

Ebert, K.M. et al. (1988) "A Moloney MLV–Rat Somatotropin Fusion Gene Produces Biologically Active Somatotropin in a Transgenic Pig." *Molecular Endocrinology* 2(3):277–283.

Efrat, S. et al., (1995) "Conditional Transformation of a Pancreatic $\beta$–Cell Line Derived From Transgenic Mice Expressing A Tetracyclin–Regulated Oncogene" *PNAS. USA,* 92:3576–3580.

Englert, C. et al. (1995) "WT1 suppresses synthesis of the epidermal growth factor receptor and induces apoptosis," *EMBO journal,* 14(19):4662–4675.

Epstein–Baak, R. et al. (1992) "Inducible Transformation of Cells from Transgenic Mice Expressing SV40 under Lac Operon Control", *Cell Growth & Differentiation* 3:127–134.

Fieck, A. et al. (1992) "Modifications of the *E. Coli* Lac Repressor for Expression in Eukaryotic Cells: Effect of Nuclear Signal Sequence on Protein Activity and Nuclear Documentation", *Nucleic Acids Research* 20:1785–1791.

Fields, S. et al. (1989) "A novel genetic system to detect protein–protein interactions" *Nature* 340:245–246.

Figge, J., et al. (1988) "Stringent Regulation of Stably Integrated Chloramphenicol Acetyl Transferase Genes by *E. coli lac* Repressor in Monkey Cells", *Cell* 52:713–722.

Fishman G. et al. (1994) "Tetracycline–Regulated Cardiac Gene Expression in Vivo" *J. Clin. Invest.* 93:1864–1868.

Frankel, F.D. et al. (1988) "Tat Protein from Human Immunodeficiency Virus Forms a Metal–Linked Dimer" *Science* 240:70–3.

Früh, K. et al. (1994) "Displacement of Housekeeping Proteasome Subunits by MHC–encoded LMP's: a Newly Discovered Mechanism for Modulating the Multicatalytic Proteinase Complex." *EMBO Journal* 13(14):3236–3244.

Früh, K. et al., (1995) "A Viral Inhibitor of Peptide Transporters for Antigen Presentation." *Nature* 375:415–418.

Furth P. (1994) "Temporal Control of Gene Expression in Transgenic Mice by A Tetracycline–Responsive Promoter" *Proc. Natl. Acad. Sci. USA* 91:9302–9306.

Gatz et al. (1992) "Stringent repression and homogeneous de–repression by tetracycline of a modified CaMV 35S promoter in intact transgenic tobacco plants," *The Plant Journal,* 2(3):397–404.

Gatz, C. et al. (1991) "Regulation of a modified CaMV 35S Promoter by the Tn 10–encoder tet repressor in Transgenic Tobacco" *Mol. Gen. Genet.* 227(2):229–237.

Gatz, C. and P. Quail (1988) "Tn10–Encoded tet Repressor Can Regulate an Operator–Containing Plant Promoter" *Proc. Natl. Acad. Sci. USA* 85:1394–1397.

Gjetting, T. et al. (1995) "Regulated Expressin of the Retinoblastoma Susceptibility Gene in Mammary Carcinoma Cells Restores Cyclin D1 Expression and $G_1$–Phase Control", *Biol. Chem. Hoppe–Seyler,* 376:441–446.

Gossen M. and B. Hermann (1993) "Anhydrotetracycline, A Novel Effector of Tetracycline Controlled Gene Expression Systems In Eukaryotic Cells" *Nucleic Acids Research* 21(18):4411–4412.

Gossen, M., et al. (1993) "Control of gene activity in higher eukaryotic cells by prokaryotic regulator elements", *TIBS* 18(12):471–475.

Gossen et al. (1995) "Exploiting prokaryotic elements for the control of gene activity in higher eukaryotics," Keystone Symposium on Gene Therapy and Molecular Medicine, Steamboat Springs, Colorado, *Journal of Cellular Biochemistry,* Supplement 0 (21A), Abstract No. C6–220, 355.

Gossen et al. (1994) "Inducible Gene Expression Systems For Higher Eukaryotic Cells" *Current Opinion in Biotechnology 5:*516–520.

Gossen, M. and Bujard, H. (1992) "Tight control of gene expression in mammalian cells by tetracycline–responsive promoters", *Proceedings of the National Academy of Science USA 89:*5547–5551.

Gossen et al. (1995) "Transcriptional activation by tetracyclines in mammalian cells," *Science, 268:*5218, 1766–1769.

Gunzburg, W. H. and Salmons, B. (1995) "Virus vector design in gene therapy", *Molecular Medicine Today 1:*410–417.

Haase, S.B. et al. (1994) "Transcription Inhibits the Replication of Autonomously Replicating Plasmids in Human Cells", *Molecular and Cellular Biology, 14(4):*2516–2524.

Hammer, R.E. et al. (1986) "Genetic Engineering of Mammalian Embryos." *J. Anim. Sci. 63:*269–278.

Hecht, B. et al. (1993) "Noninducible Tet Represosr Mutations Map from the Operator Motif to the C Terminus", *Journal of Bacteriology 175(4):*1206–1210.

Hennighause, L. et al. (1995) "Conditional Gene Expression in Secretory Tissues and Skin of Transgenic Mice Using the MMTV–LTR and the Tetracycline Responsive System", *Journal of Cellular Biochemistry, 59:*463–472.

Herschbach B. and A. Johnson (1993) "Transcriptional Repression In Eukaryotes" *Annu. Rev. Cell Biol. 9:*479–509.

Hillen, W. and Schollmeier, K. (1983) "Nucleotide sequence of the TN10 encoded tetracycline resistance gene", *Nucleic Acids Research 11(2):*525–539.

Hinrichs, W. et al. (1994) "Structure of the Tet Repressor–Tetracycline Complex and Regulation of Antibiotic Resistance", *Science 264:*418–420.

Howe, J.R. et al., (1995) "The Responsiveness of a Tetracycline–Sensitive Expression System Differs in Different Cell Lines", *The Journal of Biological Chemistry 270,* No. 23, pp. 14168–14174.

Houdebine, L.–M. (1994) "Production fo Parmaceutical Proteins from Transgenic Animals", *Journal of Biotechnology 34:*269–287.

Hu, M.C–T and Davidson, N. (1987) "The Inducible lac Operator–Repressor System Is Functional in Mammalian Cells", *Cell 46:*555–566.

Kao, C.C. et al. (1990) "Cloning of a Transcriptionally Active Human TAT Binding Factor" *Science 248:* 1646–1650.

Kappel, C.A. et al. (1992) "Regulating Gene Expression In Transgenic Animals", *Current Opinion In Biotechnology 3:*548–553.

Krimpenfort, P. et al. (1991) "Generation of Transgenic Dairy Cattle Using 'in vitro' Embryo Procution." *BIO/Technology 9:*844–847.

Labow, M.A. et al. (1990) "Conversion of the lac Repressor into an Allosterically Regulated Transcriptional Activator for Mammalian Cells", *Molecular and Cellular Biology 10(7):*3343–3356.

Landschulz, W.H. et al. (1989) "The DNA Binding Domain of the Rat Liver Nuclear Protein C/EBP is Bipartite" *Science 243:*1681–1688.

Liang et al. (1995) "Enhanced and switchable expression systems for gene–transfer," Keystone Symposium on Gene Therapy and Molecular Medicine, Steamboat Springs, Colorado, *Journal of Cellular Biochemistry,* Supplement 0 (21A), Abstract No. C6–220, 379.

Licht, J. et al. (1990) "Drosophila Krüppel Protein is a Transcriptional Repressor" *Nature 346:*76–79.

Maheswaran, S. et al. (1995) "The WT1 Gene Product Stabilizes p53 and Inhibits p53–mediated Apoptosis." *Genes & Development 9:*2143–2156.

Mansour, S.L. et al. (1988) "Disruption of the Proto–Oncogene int–2 in Mouse Enbryo–Derived Stem Cells: A General Stragegy for Targeting Mutations to Non–Selectable Genes" *Nature 336:*348–352.

Marshall, E. (1995) "Gene Therapy's Growing Pains" *Science 269:*1050–1055.

Mastrelangelo et al. (1996) "Gene Terapy for Human Cancer: An Essay for Clinicians" *Seminars in Oncology 23:(1):*4–21.

McKnight, S.L. (1984) "The Distal Transcription Signals of the Herpesvirus tk Gene Share a Common Hexanucleotide Control Sequence" *Cell 37:*253–262.

Mendez, B. et al. (1980) "Heterogeneity of tetracycline resistance determinants" *Plasmid 3:*99–108.

Mermod N. et al. (1989) "The Proline–Rich Trancriptional Activator of CTF/NF–I Is Distinct fom the Replication and DNA Binding Domain" *Cell 58:*741–753.

Miller, K. et al. (1995) "The Function of Inducible Promoter Systems in F9 Embryonal Carcinoma Cells", *Experimental Cell Research, 218:*144–150.

Muller, G. et al. (1995) "Characterization Of Non–Inducible Tet Repressor Mutants Suggests Conformational Changes Necessary For Induction", *Nature Structural Biology,* 2 :693–703.

Mullins, L.J. and Mullins, J.J. (1996) "Transgenesis in the Rat and Larger Mammals." *J. Clin. Invest.* 98(11) Supplement 1996:S37–S40.

Murre, C. et al. (1989) "Interactions Between Heterologous Helix–Loop–Helix Proteins Generate Complexes That Bind Specifically to a Common DNA Sequence" *Cell 58:*537–544.

Notarianni, et al. (1994) "Production of pharmaceutical proteins from transgenic animals", *Journal of Reproduction and Facility, 41:*51–56.

Orkin, S. H. and Motulsky, A.G. (1995) "Report and recommendations of the panel to assess the NIH investment in research on gene therapy" http://www.nih.gov/news/panel-rep.html.

Passman, R.S. et al. (1994) "Regulated Expression of Foreign Genes In Vivo After Germline Transfer", *J. Clin. Invest., 94:*2421–2425.

Pescini R. et al. (1994) "Inducible Inhibition of Eukaryotic Gene Expression" *Biochemical and Biophysical Research Communications 202(3):*1664–1667.

Postle, K. et al., (1984) "Nucleotide sequence of the repressor gene of the TN10 tetracycline resistance determinant", *Nucleic Acids Research 12(12):*4849–4863.

Pursel et al. (1989) "Genetic engineerign of livestock" *Science 244:*1281–1288.

Renkawitz R. (1990) "Transcriptional Repression In Eukaryotes" *TIG 6(6):*192–193.

Resnitzky D. (1994) "Acceleration of the G1/S Phase Transition by Expression of Cyclins D1 and E with an Inducible System" *Molecular and Cellular Biology 14(3):*1669–1679.

Rubin, et al. (1990) "Interdomain hybrid Tet proteins confer tetracycline resistance only when they are derived from closely related members of the tet gene family." *J. Bacteriol.* 172:2303–12.

Salter, et al. (1987) "Transgenic chickens: insertion of retroviral genes into the chicken germ line" *Virology* 157:236–240.

Sato, K. et al., (1986) "A specific DNA Sequence Controls Termination of Transcription in the Gastrin Gene" *Molecular and Cellular Biology* 6(4): 1032–1043.

Sauer, F. and H. Jäckle (1993) "Dimerization and the Control of Transcription by Krüppel" *Nature 364:*454–457.

Seamark, R.F. (1994) "Progress and Emerging Problems in Livestock Transgenesis: a Summary Perspective." *Reprod. Fertil. Dev. 6:*653–657.

Seipel, K., et al. (1992) "Different activation domains stimulate transcription from remote ('enhancer') and proximal ('promoter') positions", *The EMBO Journal* 11(13):4961–4968.

Shan, B., et al. (1994) "Deregulated Expression of E2F–1 Induces S–Phase Entry and Leads to Apoptosis." *Molecular and Cellular Biology* 14(12):8166–8173.

Sizemore, C. et al. (1990) "Quantitative Analysis of Tn10 Tet Rpressor Binging To A Complete Set Of Tet Operator Mutants", *Nucleic Acids Research, 18(10)*:2875–2880.

Smithies, O. et al. (1985) "Insertion of DNA sequences into the human chromosomal β–globin locus by homologous recombination", *Nature 317:*230–234.

Sopher, B.L. et al. (1994) "Cytotoxicity Mediated By Conditional Expression of a Carboxyl–Terminal Derivative of the β–Amyloid Precursor Protein", *Molecular Brain Research, 26:*207–217.

Strojek, et al. (1988) "The Use Of Transgenic Animal Techniques For Livestock Improvement", *Genetic Engineering, Principles and Methods, 10:*221–246.

Tovar, K. et al. (1988) "Identification and nucleotide sequence of the class E tet regulatory elements and operator and inducer binding of the encoded purified Tet repressor", *Mol. Gen. Genet. 215:*76–80.

Triezenberg, S.J. et al. (1988) "Functional dissection of VP16, the trans–activator of herpes simplex virus immediate early gene expression", *Genes & Development 2:*718–729.

Unger, B. et al., (1984) "Nucleotide sequence of the gene, protein purification and characterization of the pSC101–encoded tetracycline resistance–gene–repressor", *Gene. 31:*103–108.

Unger, B. et al. (1984) "Nucleotide sequence of the repressor gene of the RA1 tetracycline resistance determinant: structureal and functional comparison with three related Tet repressor genes", *Nucleic Acids Research* 12(20):7693–7703.

Wall, R.J. (1996) "Transgenic Livestock:Progress and Prospects For The Future"*Theriogenology, 45:*57–68.

Waters, S.H. et al. (1983) "The tetracycline resistance determinants of RP1 and Tn1721: nucleotide sequence analysis", *Nucleic Acids Research 11(17)*:6089–6105.

Weinmann P. et al. (1994) "A Chimeric Transactivator Allows Tetracycline–Responsive Gene Expression in Whole Plants" *The Plant Journal 5(4)*:559–569.

Wimmel A. et al. (1994) "Inducible Acceleration of G1 Progression Through Tetracycline–Regulated Expression of Human Cyclin E" *Oncogene 9:*995–997.

Wissmann, A. et al. (1991) "Selection for Tn10 Tet Repressor Binding to tet Operator in *Escherichia coli:* Isolation of Temperature–Sensitive Mutants and and combinatorial Mutagenesis in the DNA Binding Motif" *Genetics 128:*225–232.

Wissman, A., et al. (1991) "Amino Acids Determining Operator Binding Specificity In The Helix–Turn–Helix Mofit Of Tn10 Tet Repressor", *The EMBO Journal, 10(13)*:4145–4152.

Wu, Z. et al., (1995) "Conditional Ectopic Expression of C/EBPβ in NIH–3T3 Cells Induces PPAR γ and Stimulates Adipogenesis", *Genes & Development, 9:*2350–2363.

Wyborski, D.L., and Short, J.M., (1991) "Analysis of Inducers of the *E. Coli* Lac Repressor System in Mammalian Cells and Whole Animals", *Nucleic Acids Research 19:*4647–4653.

Yarranton G. (1992) "Inducible Vectors For Expression In Mamalian Cells" *Current Opinion in Biotechnology 3:*506–511.

* cited by examiner

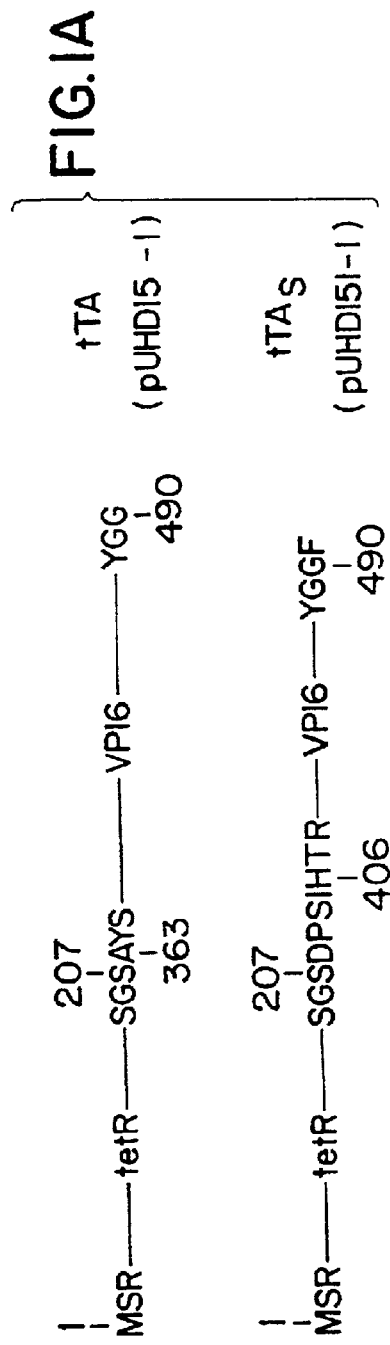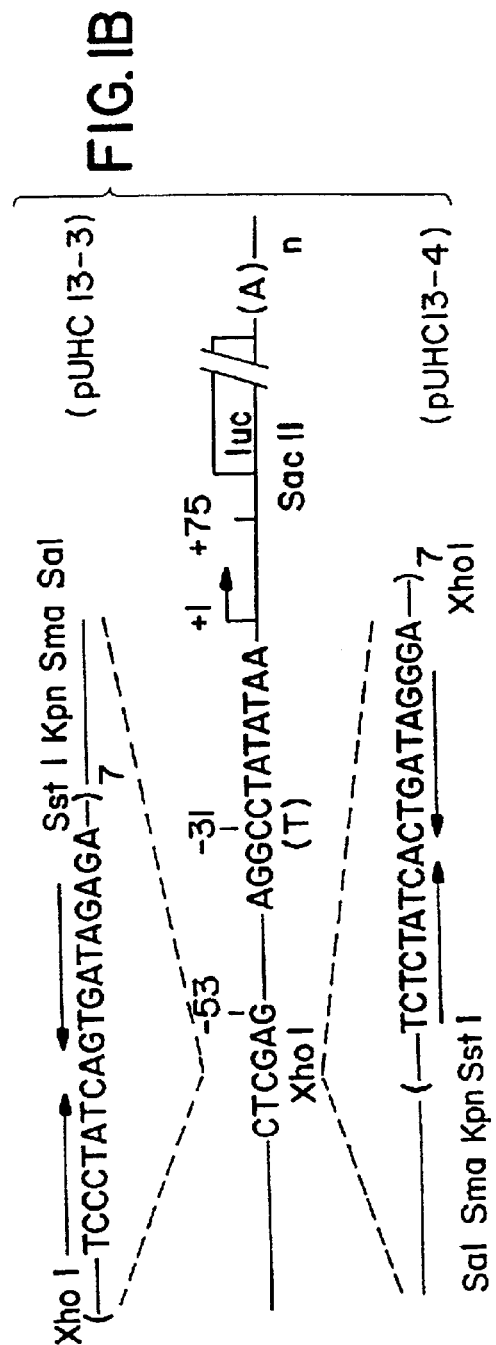

```
ATG TCT AGA TTA GAT AAA AGT AAA GTG ATT AAC AGC GCA TTA GAG CTG CTT AAT
Met Ser Arg Leu Asp Lys Ser Lys Val Ile Asn Ser Ala Leu Glu Leu Leu Asn

GAG GTC GGA ATC GAA GGT TTA ACA ACC CGT AAA CTC GCC CAG AAG CTA GGT GTA
Glu Val Gly Ile Glu Gly Leu Thr Thr Arg Lys Leu Ala Gln Lys Leu Gly Val

GAG CAG CCT ACA TTG TAT TGG CAT GTA AAA AAT AAG CGG GCT TTG CTC GAC GCC
Glu Gln Pro Thr Leu Tyr Trp His Val Lys Asn Lys Arg Ala Leu Leu Asp Ala

TTA GCC ATT GAG ATG TTA GAT AGG CAC CAT ACT CAC TTT TGC CCT TTA GAA GGG
Leu Ala Ile Glu Met Leu Asp Arg His His Thr His Phe Cys Pro Leu Glu Gly

GAA AGC TGG CAA GAT TTT TTA CGT AAT AAG GCT AAA AGT TTT AGA TGT GCT TTA
Glu Ser Trp Gln Asp Phe Leu Arg Asn Lys Ala Lys Ser Phe Arg Cys Ala Leu
```

*Fig. 4A*

```
CTA AGT CAT CGC GAT GGA GCA AAA GTA CAT TTA GGT ACA CGG CCT ACA GAA AAA
Leu Ser His Arg Asp Gly Ala Lys Val His Leu Gly Thr Arg Pro Thr Glu Lys

CAG TAT GAA ACT CTC GAA AAT CAA TTA GCC TTT TTA TGC CAA CAA GGT TTT TCA
Gln Tyr Glu Thr Leu Glu Asn Gln Leu Ala Phe Leu Cys Gln Gln Gly Phe Ser

CTA GAG AAT GCA TTA TAT GCA CTC AGC GCT GTG GGG CAT TTT ACT TTA GGT TGC
Leu Glu Asn Ala Leu Tyr Ala Leu Ser Ala Val Gly His Phe Thr Leu Gly Cys

GTA TTG GAA GAT CAA GAG CAT CAA GTC GCT AAA GAA GAA AGG GAA ACA CCT ACT
Val Leu Glu Asp Gln Glu His Gln Val Ala Lys Glu Glu Arg Glu Thr Pro Thr

ACT GAT AGT ATG CCG CCA TTA TTA CGA CAA GCT ATC GAA TTA TTT GAT CAC CAA
Thr Asp Ser Met Pro Pro Leu Leu Arg Gln Ala Ile Glu Leu Phe Asp His Gln
```

*Fig. 4B*

```
GGT GCA GAG CCA GCC TTC TTA TTC GGC CTT GAA TTG ATC ATA TGC GGA TTA GAA
Gly Ala Glu Pro Ala Phe Leu Phe Gly Leu Glu Leu Ile Ile Cys Gly Leu Glu

AAA CAA CTT AAA TGT GAA AGT GGG TCC GCG TAC AGC CGC GCG CGT ACG AAA AAC
Lys Gln Leu Lys Cys Glu Ser Gly Ser Ala Tyr Ser Arg Ala Arg Thr Lys Asn

AAT TAC GGG TCT ACC ATC GAG GGC CTG CTC GAT CTC CCG GAC GAC GAC GCC CCC
Asn Tyr Gly Ser Thr Ile Glu Gly Leu Leu Asp Leu Pro Asp Asp Asp Ala Pro

GAA GAG GCG GGG CTG GCG GCT CCG CGC CTG TCC TTT CTC CCC GCG GGA CAC ACG
Glu Glu Ala Gly Leu Ala Ala Pro Arg Leu Ser Phe Leu Pro Ala Gly His Thr

CGC AGA CTG TCG ACG GCC CCC CCG ACC GAT GTC AGC CTG GGG GAC GAG CTC CAC
Arg Arg Leu Ser Thr Ala Pro Pro Thr Asp Val Ser Leu Gly Asp Glu Leu His
```

*Fig. 4C*

TTA GAC GGC GAG GAC GTG GCG ATG GCG CAT GCC GAC GCG CTA GAC GAT TTC GAT
Leu Asp Gly Glu Asp Val Ala Met Ala His Ala Asp Ala Leu Asp Asp Phe Asp

CTG GAC ATG TTG GGG GAC GGG GAT TCC CCG GGT CCG GGA TTT ACC CCC CAC GAC
Leu Asp Met Leu Gly Asp Gly Asp Ser Pro Gly Pro Gly Phe Thr Pro His Asp

TCC GCC CCC TAC GGC GCT CTG GAT ATG GCC GAC TTC GAG TTT GAG CAG ATG TTT
Ser Ala Pro Tyr Gly Ala Leu Asp Met Ala Asp Phe Glu Phe Glu Gln Met Phe

ACC GAT CCC CTT GGA ATT GAC GAG TAC GGT GGG TAG
Thr Asp Pro Leu Gly Ile Asp Glu Tyr Gly Gly *

*Fig. 4D*

ATG TCT AGA TTA GAT AAA AGT AAA GTG ATT AAC AGC GCA TTA GAG CTG CTT AAT
Met Ser Arg Leu Asp Lys Ser Lys Val Ile Asn Ser Ala Leu Glu Leu Leu Asn

GAG GTC GGA ATC GAA GGT TTA ACA ACC CGT AAA CTC GCC CAG AAG CTA GGT GTA
Glu Val Gly Ile Glu Gly Leu Thr Thr Arg Lys Leu Ala Gln Lys Leu Gly Val

GAG CAG CCT ACA TTG TAT TGG CAT GTA AAA AAT AAG CGG GCT TTG CTC GAC GCC
Glu Gln Pro Thr Leu Tyr Trp His Val Lys Asn Lys Arg Ala Leu Leu Asp Ala

TTA GCC ATT GAG ATG TTA GAT AGG CAC CAT ACT CAC TTT TGC CCT TTA GAA GGG
Leu Ala Ile Glu Met Leu Asp Arg His His Thr His Phe Cys Pro Leu Glu Gly

GAA AGC TGG CAA GAT TTT TTA CGT AAT AAC GCT AAA AGT TTT AGA TGT GCT TTA
Glu Ser Trp Gln Asp Phe Leu Arg Asn Asn Ala Lys Ser Phe Arg Cys Ala Leu

*Fig. 5A*

CTA AGT CAT CGC GAT GGA GCA AAA GTA CAT TTA GGT ACA CGG CCT ACA GAA AAA
Leu Ser His Arg Asp Gly Ala Lys Val His Leu Gly Thr Arg Pro Thr Glu Lys

CAG TAT GAA ACT CTC GAA AAT CAA TTA GCC TTT TTA TGC CAA CAA GGT TTT TCA
Gln Tyr Glu Thr Leu Glu Asn Gln Leu Ala Phe Leu Cys Gln Gln Gly Phe Ser

CTA GAG AAT GCA TTA TAT GCA CTC AGC GCT GTG GGG CAT TTT ACT TTA GGT TGC
Leu Glu Asn Ala Leu Tyr Ala Leu Ser Ala Val Gly His Phe Thr Leu Gly Cys

GTA TTG GAA GAT CAA GAG CAT CAA GTC GCT AAA GAA AGG GAA ACA CCT ACT
Val Leu Glu Asp Gln Glu His Gln Val Ala Lys Glu Arg Glu Thr Pro Thr

ACT GAT AGT ATG CCG CCA TTA TTA CGA CAA GCT ATC GAA TTA TTT GAT CAC CAA
Thr Asp Ser Met Pro Pro Leu Leu Arg Gln Ala Ile Glu Leu Phe Asp His Gln

*Fig. 5B*

```
GGT GCA GAG CCA GCC TTC TTA TTC GGC CTT GAA TTG ATC ATA TGC GGA TTA GAA
Gly Ala Glu Pro Ala Phe Leu Phe Gly Leu Glu Leu Ile Ile Cys Gly Leu Glu

AAA CAA CTT AAA TGT GAA AGT GGG TCT GAT CCA TCG ATA CAC ACG CGC AGA CTG
Lys Gln Leu Lys Cys Glu Ser Gly Ser Asp Pro Ser Ile His Thr Arg Arg Leu

TCG ACG GCC CCC CCG ACC GAT GTC AGC CTG GGG GAC GAG CTC CAC TTA GAC GGC
Ser Thr Ala Pro Pro Thr Asp Val Ser Leu Gly Asp Glu Leu His Leu Asp Gly

GAG GAC GTG GCG ATG GCG CAT GCC GAC GCG CTA GAC GAT TTC GAT CTG GAC ATG
Glu Asp Val Ala Met Ala His Ala Asp Ala Leu Asp Asp Phe Asp Leu Asp Met

TTG GGG GAC GGG GAT TCC CCG GGT CCG GGA TTT ACC CCC CAC GAC TCC GCC CCC
Leu Gly Asp Gly Asp Ser Pro Gly Pro Gly Phe Thr Pro His Asp Ser Ala Pro
```

*Fig. 5C*

TAC GGC GCT CTG GAT ATG GCC GAC TTC GAG TTT GAG CAG ATG TTT ACC GAT GCC
Tyr Gly Ala Leu Asp Met Ala Asp Phe Glu Phe Glu Gln Met Phe Thr Asp Ala

CTT GGA ATT GAC GAG TAC GGT GGG TTC TAG
Leu Gly Ile Asp Glu Tyr Gly Gly Phe *

*Fig 5D*

GAATTCCTCGAGTTTACCACTCCCTATCAGTGATAGAGAAAAGTGAAAGTCGAGTTTACCACTC
CCTATCAGTGATAGAGAAAAGTGAAAGTCGAGTTTACCACTCCCTATCAGTGATAGAGAAAAGT
GAAAGTCGAGTTTACCACTCCCTATCAGTGATAGAGAAAAGTGAAAGTCGAGTTTACCACTCCC
TATCAGTGATAGAGAAAAGTGAAAGTCGAGTTTACCACTCCCTATCAGTGATAGAGAAAAGTGA
AAGTCGAGTTTACCACTCCCTATCAGTGATAGAGAAAAGTGAAAGTCGAGCTCGGTACCCGGGT
CGAGTAGGCGTGTACGGTGGGAGGCCTATATAAGCAGAGCTCGTTTAGTGAACCGTCAGATCGC
CTGGAGACGCCATCCAGCGCTGTTTTGACCTCCATAGAAGACACCGGGACCGATCCAGCCTCCGC
GG

*Fig. 6*

GAATTCCTCGACCCGGGTACCGAGCTCGACTTTCACTTTTCTCTATCACTGATAGGGAGTGGTA

AACTCGACTTTCACTTTTCTCTATCACTGATAGGGAGTGGTAAACTCGACTTTCACTTTTCTCT

ATCACTGATAGGGAGTGGTAAACTCGACTTTCACTTTTCTCTATCACTGATAGGGAGTGGTAAA

CTCGACTTTCACTTTTCTCTATCACTGATAGGGAGTGGTAAACTCGACTTTCACTTTTCTCTAT

CACTGATAGGGAGTGGTAAACTCGACTTTCACTTTTCTCTATCACTGATAGGGAGTGGTAAACT

CGAGTAGGCGTGTACGGTGGGAGGCCTATATAAGCAGAGCTCGTTTAGTGAACCGTCAGATCGC

CTGGAGACGCCATCCACGCTGTTTTGACCCTCCATAGAAGACACCGGGACCGATCCAGCCTCCGC

```
GAGCTCGACTTTCACTTTTCTCTATCACTGATAGGGAGTGGTAAACTCGACTTTCACTTTTCTC
TATCACTGATAGGGAGTGGTAAACTCGACTTTCACTTTTCTCTATCACTGATAGGGAGTGGTAA
ACTCGACTTTCACTTTTCTCTATCACTGATAGGGAGTGGTAAACTCGACTTTCACTTTTCTCTA
TCACTGATAGGGAGTGGTAAACTCGACTTTCACTTTTCTCTATCACTGATAGGGAGTGGTAAAC
TCGACTTTCACTTTTCTCTATCACTGATAGGGAGTGGTAAACTCGAGATCCCGGGAATTCGAAC
ACGCAGATGCAGTCGGGGGCGCGGTCCGAGGTCCACTTCGGCATATTAAGGTGACGCCGTGTGG
CCTCGAACACCGAG
```

Fig. 8

CTCGAGTTTACCACTCCCTATCAGTGATAGAGAAAAGTGAAGTCGAGTTTACCACTCCCTATC
AGTGATAGAGAAAAGTCGAGTTTACCACTCCCTATCAGTGATAGAGAAAAGTGAAAGT
CGAGTTTACCACTCCCTATCAGTGATAGAGAAAAGTCGAGTTTACCACTCCCTATCAG
TGATAGAGAAAAGTGAAGTCGAGTTTACCACTCCCTATCAGTGATAGAGAAAAGTCGAAAGTCG
AGTTTACCACTCCCTATCAGTGATAGAGAAAAGTCGAGCTCGGTACCCGGGTCGAGTA
GGCGTGTACGGTGGGAGGCCTATATAAGCAGAGCTCGTTTAGTGAACCGTCAGATCGCCTGGAG
ACGCCATCCACGCTGTTTGACCTCCATAGAAGACACGGGACCGATCCAGCCTCCGGGCCCC
GAATTCGAGCTCGGTACCGGGCCCCCCCTCGAGGTCGACGGTATCGATAAGCTTGATATCGAAT
TCCAGGAGGTGGAGATCCGCGGGTCCAGCCAAACCCCACACCCCATTTCTCCTCCCCTCTGCCCC
TATATCCCGGCACCCCCCTTCCCCTAGCCCTTTCCCCTGAGAGACGGGGAGGAGAAAAG
GGGAGTT''AGGTCGACATGACTGAGCTGAAGGCAAAGGAACCTCGGGCTCCCCACGTGGCGGGC
GGCGCGCCCTCCCCCGGACCCGCCCCGGACCCTGGCCCCTTCC
AGGGGAGCCCAGAGACCTCAGAGGCCTCGTCGTAGTCTCCGCCATCCCCATCTCCCTGACGGGTT

*Fig. 9A*

```
GCTCTTCCCCCGGCCCCTGTCAGGGCAGAACCCCCCAGACGGGAAGACGCAGAGACGCAGGACCCACCGTCG
TTGTCAGACGTGTGGAGGGGCGCATTTCCTGGAGTCGAAGCCCCGGAGGGGCAGGAGACAGCAGCT
CGAGACCTCCAGAAAAGGACAGCGGCCTGCTGGACAGTGTCCTGACACGCTCCTGGCCCCTC
GGGTCCCGGGCAGAGCCAGCCACGCCAGCCCTGCCACCTGCGAGGCCATCAGCCCGTGGTGCCTGTTT
GGCCCCGACCTTCCCGAAGACCCCGGCTGCCCCGGCTACCAAAGGGGTGTTGGCCCCGCTCA
TGAGCCGACCCGAGGACAAGGCAGGCGACAGCTCTGGGACGGCCCTCACTGGCCGGCA
CAGGGGACTGTCACCATCCCCGCAGCCCTGCGGTGCAGGTAGACGAGGAGACAGCTCCGAATCCGAGG
GTGAAGCCATCCCCCCGAGCCATCTCGGGCCAACCTCGGGCCAGAGGCAGGAGCACGGCCGGAGGAGG
GCACCGTGGCCCGCTCCTGAAGGCCTCCTGGAGCGGCGTCGCCCTTGTCCCCAAGGAAGATTCT
AGCTGCCCCCGTCGCTCGGCCCCAGGGTCTCCTTGGCGGTCAGGAGCAGGAGCGCCGGTGGCCTGGGCTCCC
CGCTTCTCGGCCCCAGGGTCGGTGGTGATTTCATCCACGTGCCCATCCTGCCTCTCAACCACGCTTTCCT
CGCTGGCCACCTCGGTGCTGTGGATCAGCTGCTGACGGGCAGCTACGAGAGCTACGACGGGAGGCTACGC
GGCCACCCGCACCAGGCAGCTGCTGAGGGGAGAGCTACGACGGGCGGGGCCGCCAGC
```

*Fig. 9B*

CCCTTCGTCCCGCAGCGGGGCTCCCCTCTGCCTCGTCCACCCCTGTGGCGGCGACTTCC
CCGACTGCACCTACCCGCCCGAGCCCGAAAGATGACGCGTTCCCCCTCTACGGGCGACTT
CCAGCCGCCCCGCCCTCAAGATAAAGGAGGAGAAGCCGGAGCCCGGCGCGCGCTCCCCG
CGTACGTACCTGGTGGCTGGTGTGCAAACCCGCGCCTTCCCGACTTCCAGCTGGCAGCGCCGC
CGCCACCCTCGCTGCCGCCCTCGAGTGCCCTCGTCCAGACCCGGGAAGCGGCGGTGGCGGCCTC
CCCAGGCAGTGCCTCCCGTCTCCTCCTCGTCGGGGTCGACCCTGGAGTGCATCCTGTAC
AAGGCAGAAGGCGCGCCCAGCAGGCCCCTTCGCGCGCCCTGCCCTGCAAGCCTCCGGGCG
CCGGGCGCCTGCTCCCGGGACGGCCTGCCCTCCACCTCCGCCTCGGGGCAGCCGCCGG
GGCCGCCCCTGCGCTCTACCCGACGCTCGGCCTCAACGGACTCCCGCAACTCGGCTACCAGGCC
GCCGTGCTCAAGGAGGCCTGCCGCAGGTCTACACGCCCCTATCTCAACTACCTGAGGCCGGATT
CAGAAGCCAGTCAGAGCCCACAGTACAGCTTCGAGTCACTACCTCAGAAGATTTGTTTGATCTG
TGGGGATGAAGCATCAGGCTGTCATTATGGTGTCCTCACCTGTGGGAGCTGTAAGGTCTTCTTT
AAAAGGGCAATGGAAGGGCAGCATAACTATTTATGTGCTGGAAGAAATGACTGCATTGTTGATA

*Fig. 9C*

```
AAATCCGCAGGAAAAACTGCCCGGCCGTGTCGCCTTAGAAAGTGCTGTCAAGCTGGCATGGTCCT
TGGAGGGCGAAAGTTTAAAAAGTTCAATAAAGTCAGAGTCATGAGAGCACTCGATGCTGTTGCT
CTCCCACAGCCAGTGGGCATTCCAAATGAAAGCCAACGAATCACTTTTCTCCAAGTCAAGAGA
TACAGTTAATTCCCCTCTAATCAACCTGTTAATGAGCATTGAACCAGATGTGATCTATGCAGG
ACATGACAACACAAAGCCTGATACCTCCAGTTCTTTGCTGACGAGTCTTAATCAACTAGGCGAG
CGGCAACTTCTTTCAGTGGTAAAATGGTCCAAATCTCTTCCAGGTTTTCGAAACTTACATATTG
ATGACCAGATAACTCTCATCCAGTATTCTTGGATGAGTTTAATGGTATTTGGACTAGGATGGAG
ATCCTACAAACATGTCAGTGGGCAGATGCTGTATTTGCACCTGATCTAATATTAAATGAACAG
CGGATGAAAGAATCATCATTCTATTCACTATGCCTTACCATGTGGCAGATACCGCAGGAGTTTG
TCAAGCTTCAAGTTAGCCAAGAAGAGTTCCTCTGCATGAAAGTATTACTACTTCTTAATACAAT
TCCTTTGGAAGGACTAAGAAGTCAAAGCCAGTTTGAAGAGATGAGATCAAGCTACATTAGAGAG
CTCATCAAGGCAATTGGTTTGAGGCAAAAAGGAGTTGTTTCCAGCTCACAGCGTTTCTATCAGC
TCACAAAACTTCTTGATAACTTGCATGATCTTGTCAAACAACTTCACCTGTACTGCCTGAATAC
```

*Fig. 9D*

ATTTATCCAGTCCCGGGGCGCTGAGTGTTGAATTTCCAGAAATGATGTCTGAAGTTATTGCTGCA

CAGTTACCCAAGATATTGGCAGGATGGTGAAACCACTTCTCTTTCATAAAAAGTGAATGTCAA

TTATTTTCAAAGAATTAAGTGTTGTGGTATGTCTTTCGTTTTGGTCAGGATTATGACGTCTCG

AGTTTTATAATATTCTGAAAGGGAATTCCTGCAGCCCGGGGATCCACTAGTTCTAGAGGATC

CAGACATGATAAGATACATTGATGAGTTTGGACAAACCACAACTAGAATGCAGTGAAAAAATG

CTTTATTGTGAAATTTGTGATGCTATTGCTTTATTGTAACCATTATAAGCTGCAATAAACAA

GTTAACAACAACAATTGCATTCATTTATGTTTCAGGTTCAGGGGAGGTGTGGGAGGTTTTTT

AAAGCAAGTAAAACCTCTACAAATGTGGTATGGCTGATTATGATCCTGCAAGCCTCGTCGTCTG

GCCGGACCACGCTATCTGTGCAAGGTCCCCGACGCGCTCCATGAGCAGAGCGCCCGCCGCC

GAGGCAAGACTCGGGCGGCCCTGCCCGTCCCACCAGGTCAACAGGCGGTAACCGGCCTCTTC

ATCGGGAATGCGCGACCTTCAGCATCGCCGGCATGTCCCCTGGCGACGGGAAGTATCAGCT

CGACCAAGCTTGGCGAGATTTTCAGGAGCTAAGGAAGCTAAAATGGAGAAAAAATCACTGGAT

ATACCACCGTTGATATATCCCAATGGCATCGTAAAGAACATTTGAGGCATTTCAGTTCAGTTGC

Fig. 9E

TCAATGTACCTATAACCAGACCGTTCAGCTGCATTAATGAATCGGCCAACGCGCGGGGAGAGGC
GGTTTGCCGTATTGGGCGCTCTTCCGCTTCCTCGCTCACTGACTCGCTGCGCTCGGTCGTTCGGC
TGCGGCGAGCGGTATCAGCTCACTCAAAGGCGGTAATACGGTTATCCACAGAATCAGGGGATAA
CGCAGGAAAGAACATGTGAGCAAAAGGCCAGCAAAAGGCCAGGAACCGTAAAAAGGCCGCGTTG
CTGGCGTTTTTCCATAGGCTCCGCCCCCCTGACGAGCATCACAAAAATCGACGCTCAAGTCAGA
GGTGGCGAAACCCGACAGGACTATAAAGATACCAGGCGTTTCCCCCTGGAAGCTCCCTCGTGCG
CTCTCCTGTTCCGACCCTGCCGCTTACCGGATACCTGTCCGCCTTTCTCCCTTCGGGAAGCGTG
GCGCTTTCTCAATGCTCACGCTGTAGGTATCTCAGTTCGGTGTAGGTCGTTCGCTCCAAGCTGG
GCTGTGTGCACGAACCCCCCGTTCAGCCCGACCGCTGCGCCTTATCCGGTAACTATCGTCTTGA
GTCCAACCCGGTAAGACACGACTTATCGCCACTGGCAGCAGCCACTGGTAACAGGATTAGCAGA
GCGAGGTATGTAGGCGGTGCTACAGAGTTCTTGAAGTGGTGGCCTAACTACGGCTACACTAGAA
GGACAGTATTTGGTATCTGCGCTCTGCTGAAGCCAGTTACCTTCGGAAAAAGAGTTGGTAGCTC
TTGATCCGGCAAACAAACCACCGCTGGTAGCGGTGGTTTTTTGTTTGCAAGCAGCAGATTACG

*Fig. 9F*

```
CGCAGAAAAAAGGATCTCAAGAAGATCCTTTGATCTTTTCTACGGGTCTGACGCTCAGTGGA
ACGAAAACTCACGTTAAGGGATTTTGGTCATGAGATTATCAAAAAGGATCTTCACCTAGATCCT
TTTAAATTAAAAATGAAGTTTTAAATCAATCTAAAGTATATATGAGTAAACTTGGTCTGACAGT
TACCAATGCTTAATCAGTGAGGCACCTATCTCAGCGATCTGTCTATTTCGTTCATCCATAGTTG
CCTGACTCCCCGTCGTGTAGATAACTACGATACGGGAGGGCTTACCATCTGGCCCCAGTGCTGC
AATGATACCGCGAGACCCACGCTCACCGGCTCCAGATTTATCAGCAATAAACCAGCCAGCCGGA
AGGGCCGAGCGCAGAAGTGGTCCTGCAACTTTATCCGCCTCCATCCAGTCTATTAATTGTGCC
GGGAAGCTAGAGTAAGTAGTTCGCCAGTTAATAGTTTGCGCAACGTTGTTGCCATTGCTACAGG
CATCGTGGTGTCACGCTCGTCGTTTGGTATGGCTTCATTCAGCTCCGGTTCCCAACGATCAAGG
CGAGTTACATGATCCCCCATGTTGTGCAAAAAGCGGTTAGCTCCTTCGGTCCTCCGATCGTTG
TCAGAAGTAAGTTGGCCGCAGTGTTATCACTCATGGTTATGGCAGCACTGCATAATTCTCTTAC
TGTCATGCCATCCGTAAGATGCTTTTCTGTGACTGGTGAGTACTCAACCAAGTCATTCTGAGAA
TAGTGTATGCGGCGACCGAGTTGCTCTTGCCCGGCGTCAATACGGGATAATACCGCGCCACATA
```

*Fig. 9G*

GCAGAACTTTAAAAGTGCTCATCATTGGAAAACGTTCTTCGGGGCGAAAACTCTCAAGGATCTT
ACCGCTGTTGAGATCCAGTTCGATGTAACCCACTCGTGCACCCAACTGATCTTCAGCATCTTTT
ACTTTCACCAGCGTTTCTGGGTGAGCAAAAACAGGAAGGCAAAATGCCGCAAAAAGGGAATAA
GGGCGACACGGAAATGTTGAATACTCATACTCTTCCTTTTCAATATTATTGAAGCATTTATCA
GGGTTATTGTCTCATGAGCGGATACATATTTGAATGTATTTAGAAAATAACAAATAGGGGTT
CCGCGCACATTCCCCGAAAAGTGCCACCTGACGTCTAAGAAACCATTATTATCATGACATTAA
CCTATAAAAATAGGCGTATCACGAGGCCCTTTCGTC

Fig. 9H

```
CTCGAGTTTACCACTCCCTATCAGTGATAGAGAAAAGTGAGTTTACCACTCCCTATC
AGTGATAGAGAAAAGTGAAAGTCGAGTTTACCACTCCCTATCAGTGATAGAGAAAAGTGAAAGT
CGAGTTTACCACTCCCTATCAGTGATAGAGAAAAGTGAGTTTACCACTCCCTATCAG
TGATAGAGAAAAGTGAAAGTCGAGTTTACCACTCCCTATCAGTGATAGAGAAAAGTGAAAGTCG
AGTTTACCACTCCCTATCAGTGATAGAGAAAAGTGAGCTCGGTACCCGGGTCGAGTA
GGCGTGTACGGTGGGAGGCCTATATAAGCAGAGCTCGTTTAGTGAACCGTCAGATCGCCTGGAG
ACGCCATCCACGCTGTTTGACCCTCCATAGAAGACACCCTCCACACCAAAGCCTCCGGCCCC
GAATTCCGCCCACGACCATGACCATGACCCTCCACACCAAAGCATCTGGATGGCCCTACTGCA
TCAGATCCAAGGGAACGAGCTGGAGCCCCTGAACCGTCCGCAGCTCAAGATCCCCTGGAGCGG
CCCCTGGGCGAGGTGTACCTGGACAGCAGCAAGCCCGCCGTGTACAACTACCCCGAGGGCCG
CCTACGAGTTCAACGCCGGCCGCCAACGCGCAGTCTACGGTCAGACCGGCCTCCCCTA
CGGCCCCGGGTCTGAGGCTGCGGGCGTTCGGCTCCAACGGCCTGGGGGTTTCCCCCACTCAAC
AGCGGTGTCTCCGAGCCCGCTGATGCTACTGCACCCGCCGCAGCTGTCGCCTTTCCTGCAGC
```

*Fig. 10A*

```
CCCACGGCCAGCAGTGCCCTACTACCTGGAGAACGAGCCCAGCGGCTACACGGTGCCGGAGGC
CGGCCCGCCGGCATTCTACAGGCCAAATTCAGATAATCGACGCCAGGGTGGCAGAGAAAGATTG
GCCAGTACCAATGACAAGGGAAGTATGGAATCTGCCAAGGAGACTCGCTACTGTGCAG
TGTGCAATGACTATGCTTCAGGCTACCATTATGGAGTCTGGTCTGTGAGGGCTGCAAGGCCTT
CTTCAAGAGAAGTATTCAAGGACATAACGACTATATGTGTCCAGCCACCAGTGCACCATT
GATAAAAACAGGAGGAAGAGCTGCCAGGCCTGCCGCAAATGCTACGAAGTGGGAATGA
TGAAAGGTGGGATACGAAAAGACCGAAGAGGGAGAATGTTGAAACACAAGCGCCAGAGAGA
TGATGGGGAGGGCAGGGGTGAAGTGGGGTCTGCTGGAGACATGAGAGCTGCCAACCTTTGGCCA
AGCCCGCTCATGATCAAACGCTCTAAGAAGAACAGCCTGGCCTTGTCCCTGACGGCCGACCAGA
TGGTCATGGCCTTGTGTTGGATGCTGAGCCCCATACTCTATTCCGAGTATGATCCTACCAGACC
CTTCAGTGAAGCTTCGATGATGATGGCTTACTGACCAACCTGGCAGACAGGAGCTGGTTCACATG
ATCAACTGGGCGAAGAGGTGCCAGGCTTTGTGATTTGACCCTCCATGATCAGGTCCACCTTC
TAGAATGTGCCTGGCTAGAGATCCTGATGATTGGTCTCGTCTGGCGCTCCATGAGCACCCAGT
```

*Fig. 10B*

```
GAAGCTACTGTTTGCTCCTAACTTGCTCTTGGACAGGAACCAGGGAAAATGTGTAGAGGGCATG
GTGGAGATCTTCGACATGCTGCTGGCTACATCATCTCGGTTCCGCATGATGAATCTGCAGGGAG
AGGAGTTTGTGTGCCTCAAATCTATTATTTGCTTAATTCTGGAGTGTACACATTTCTGTCCAG
CACCCTGAAGTCTCTGGAAGAGAAGGACCATATCCACCGAGTCCTGGACAAGATCACAGACACT
TTGATCCACCTGATGGCCAAGGCAGGCCCTGACCCTGCAGCAGCACCAGCGCTGGCCCAGC
TCCTCCTCATCCTCTCCCACATCAGGCACATGAGTAACAAAGGCATGGAGCATCTGTACAGCAT
GAAGTGCAAGAACGTGGTGCCCCTCTATGACCTGCTGCTGGAGATGCTGACGCCCACCGCCTA
CATGCGCCCACTAGCCGTGGAGGGCATCCGTGGAGGAGACGGACCAAAGCCACTTGGCCACTG
CGGGCTCTACTTCATCGCCATTCCTTGCAAAAGTATTACATCACGGGGAGGCAGAGGGTTTCCC
TGCCACAGTCTGAGAGCTCCCTGGCGAATTCGAGCTCGGTACCCGGGATCCTCTAGAGGATC
CAGACATGATAAGATACATTGATGAGTTTGGACAAACCACAACTAGAATGCAGTGAAAAAATG
CTTTATTGTGAAATTTGTGATGCTATTGCTTTATTTGTAACCATTATAAGCTGCAATAAACAA
GTTAACAACAATTGCATTCATTTTATGTTTCAGGTTCAGGGGGAGGTGTGGGAGGTTTTTT
```

*Fig. 10C*

```
AAAGCAAGTAAAACCTCTACAAATGTGGTATGGCTGATTATGATCCTGCAAGCCTCGTCTG
GCCGGACCACGCTATCTGTGCAAGGTCCCCGGACGCGCGCTCCATGAGCAGAGCCCGCCGCC
GAGGCAAGACTCGGGCGGCCCCTGCCCGTCCCACCAGTCAACAGGCGGTAACCGGCCTCTTC
ATCGGGAATGCGCGCGACCTTCAGCATCGCCCGGCATGTCCCCTGGCGACGGGAAGTATCAGCT
CGACCAAGCTTGGCGGAGATTTTCAGGAGCTAAGGAAGCTAAAATGGAGAAAAAATCACTGGAT
ATACCACCGTTGATATATCCCAATGGCATCGTAAAGAACATTTGAGGCATTTCAGTCAGTTGC
TCAATGTACCTATAACCAGACCGTTCAGCTGCATTAATGAATCGGCCAACGCGCGGGAGAGGC
GGTTTGCGTATTGGGCGCTCTTCCGCTTCACTGACTCGCTGCGCTCGGTCGTTCGGC
TGCGGGCGAGCCGGTATCAGCTCACTCAAAGGCGGTAATACGGTTATCCACAGAATCAGGGATAA
CGCAGGAAAGAACATGTGAGCAAAAGGCCAGCAACCGTAAAAAGGCCGCGTTG
CTGGCGTi.TTTCCATAGGCTCCGCCCCCCTGACGAGCATCACAAAAATCGACGCTCAAGTCAGA
GGTGGGCGAAACCCGACAGGACTATAAAGATACCAGGCGTTTCCCCCTGAAGCTCCCTGTGCG
CTCTCCTGTTCCGACCCTGCCGCTTACCGGATACCTGTCCGCCCTTTCTCCCTTCGGGAAGCGTG
```

Fig. 10D

GCGCTTTCTCAATGCTCTCACGCTGTAGGTATCTCAGTTCGGTGTGTAGGTCGTTCGCTCCAAGCTGG
GCTGTGTGCACGAACCCCCGTTCAGCCCGCTGCGCCTTATCCGGTAACTATCGTCTTGA
GTCCAACCCGGTAAGACACGACTTATCGCCACTGGCAGCAGCCACTGGTAACAGGATTAGCAGA
GCGAGGTATGTAGGCGGTGCTACAGAGTTCTTGAAGTGGTGGCCTAACTACGGCTACACTAGAA
GGACAGTATTTGGTATCTGCGCTCTGCTGAAGCCAGTTACCTTCGGAAAAAGAGTTGGTAGCTC
TTGATCCCGCAAACAAACCACCGCTGGTAGCGGTGGTTTTTTGTTTGCAAGCAGCAGATTACG
CGCAGAAAAAAGGATCTCAAGAAGATCCTTTGATCTTTTCTACGGGTCTGACGCTCAGTGGA
ACGAAAACTCACGTTAAGGGATTTTGGTCATGAGATTATCAAAAAGGATCTTCACCTAGATCCT
TTTAAATTAAAAATGAAGTTTTAAATCAATCTAAAGTATATATGAGTAAACTTGGTCTGACAGT
TACCAATGCTTAATCAGTGAGGCACCTATCTCAGCGATCTGTCTATTTCGTTCATCCATAGTTG
CCTGATCCCCGTCGTGTAGATAACTACGATACGGGAGGGCTTACCATCTGGCCCCAGTGCTGCA
ATGATACCGCGAGACCCACGCTCACCGGCTCCAGATTTATCAGCAATAAACCAGCCAGCCGGAA
GGGCCGAGCGCAGAAGTGGTCCTGCAACTTTATCCGCCTCCATCCAGTCTATTAATTGTTGCCG

*Fig. 10E*

GGAAGCTAGAGTAAGTAGTTCGCCAGTTAATAGTTTGCGCAACGTTGTTGCCATTGCTACAGGC
ATCGTGGTGTCACGCTCGTCGTTGGTATGGCTTCATTCAGCTCCGGTTCCCAACGATCAAGGC
GAGTTACATGATCCCCCATGTTGTGCAAAAAGCGGTTAGCTCCTTCGGTCCTCCGATCGTTGT
CAGAAGTAAGTTGGCCGCAGTGTTATCACTCATGGTTATGGCAGCACTGCATAATTCTCTTACT
GTCATGCCATCCGTAAGATGCTTTTCTGTGACTGGTGAGTACTCAACCAAGTCATTCTGAGAAT
AGTGTATGCGGCGACCGAGTTGCTCTTGCCCGGCGTCAATACGGGATAATACCGCGCCACATAG
CAGAACTTTAAAAGTGCTCATCATTGGAAAACGTTCTTCGGGGCGAAAACTCTCAAGGATCTTA
CCGCTGTTGAGATCCAGTTCGATGTAACCCACTCGTGCACCCAACTGATCTTCAGCATCTTTTA
CTTTCACCAGCGTTTCTGGGTGAGCAAAAACAGGAAGGCAAAATGCCGCAAAAAAGGGAATAAG
GGCGACACGGAAATGTTGAATACTCATACTCTTCCTTTTTCAATATTATTGAAGCATTATCAG
GGTTATTGTCTCATGAGCGGATACATATTTGAATGTATTTAGAAAAATAAACAAATAGGGGTTC
CGCGCACATTCCCGAAAAGTGCCACCTGACGTCTAAGAAACCATTATTATCATGACATTAAC
CTATAAAAATAGGCGTATCACGAGGCCCTTTCGTC

*Fig. 10F*

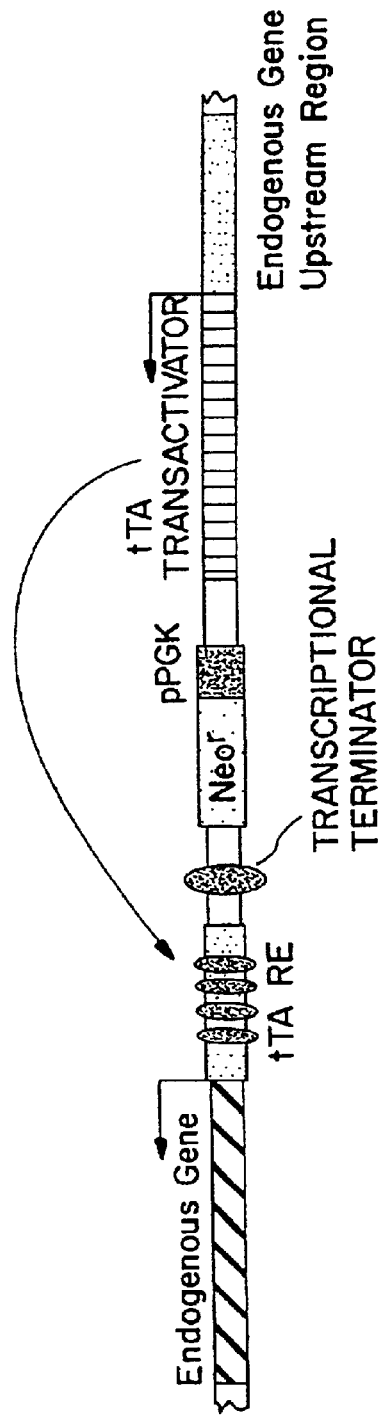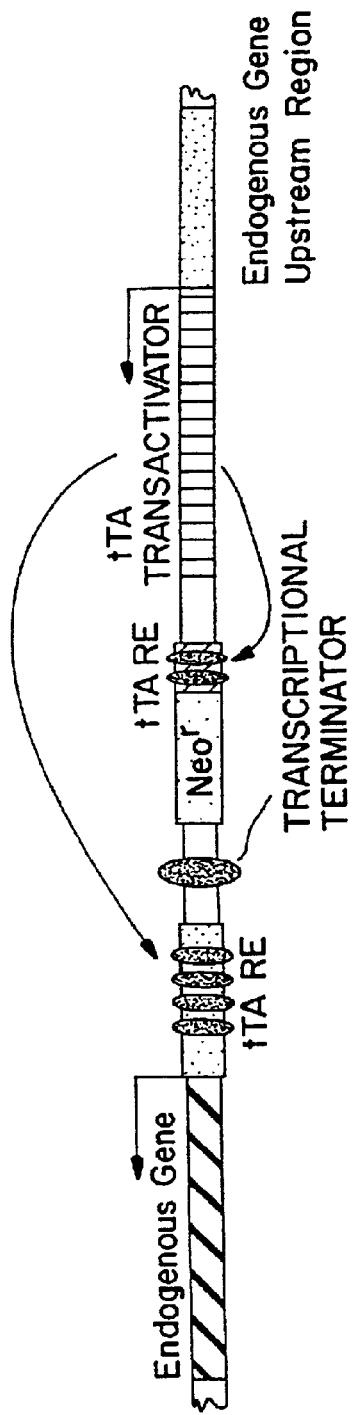

TETRACYCLINE-REGULATED TRANSCRIPTIONAL ACTIVATOR FUSION PROTEINS

RELATED APPLICATIONS

This application is a continuation of U.S. Ser. No. 09/163,276, filed Sep. 29, 1998, abandoned, which is a continuation of U.S. Ser. No. 08/479,306, filed Jun. 7, 1995, issued as U.S. Pat. No. 5,888,981, which is a continuation-in-part of U.S. Ser. No. 08/260,452, filed Jun. 14, 1994, now U.S. Pat. No. 5,650,298, which is a continuation-in-part of U.S. Ser. No. 08/076,327, filed Jun. 14, 1993, now abandoned. The entire contents of each of these applications are incorporated herein by reference.

BACKGROUND OF THE INVENTION

The study of gene function in complex genetic environments such as eucaryotic cells would greatly profit from systems that would allow stringent control of the expression of individual genes. Ideally, such systems would not only mediate an "on/off" status for gene expression but would also permit limited expression at a defined level.

Attempts to control gene activity by various inducible eucaryotic promoters responsive to, for example, heavy metal ions (Mayo et al., Cell 29:99–108 (1982); Brinster et al., Nature (London) 296:39–42 (1982); Searle et al., Nouer, L., CRC Boca Raton, Fla. (1991), pp. 167–220), or hormones (Lee et al., Nature (London) 294:228–232 (1981); Hynes et al., Proc. Natl. Acad. Sci. USA 78:2038–2042 (1981); Klock et al., Nature (London) 329:734–736 (1987); Israel & Kaufman, Nucleic Acids Res. 17:2589–2604 (1989)) have generally suffered from leakiness of the inactive state (e.g., the metallothionein promoter (Mayo et al., Cell 29:99–108 (1982)) or from pleiotropic effects caused by the inducing principles themselves, such as elevated temperature or glucocorticoid hormone action (Lee et al., Proc. Natl. Acad. Sci, USA 85:1204–1208 (1988)).

In search of regulatory systems that do not rely on endogenous control elements, several groups have demonstrated that the lac repressor/operator inducer system of *Escherichia coli* functions in eucaryotic cells. Three approaches have been described: (i) prevention of transcription initiation by properly placed lac operators at promoter sites (Hu & Davidson, Cell 48:555–566 (1987); Brown et al., Cell 49:603–612 (1987); Figge et al., Cell 52:713–722 (1988); Fuerst et al., Proc. Natl. Acad. Sci. USA 86:2549–2553 (1989); Deutschle et al., Proc. Natl. Acad. Sci. USA 86:5400–5405 (1989)), (ii) blockage of transcribing RNA polymerase II during elongation by a lac repressor/operator complex (lac R/O; Deutschle et al., Science 248:480–483 (1990)), and (iii) activation of a promoter responsive to a fusion between lacR and the activating domain of virion protein 16 (VP16) of herpes simplex virus (HSV) (Labow et al., Mol. Cell. Biol. 10:3343–3356 (1990); Baim et al., Proc. Natl. Acad. Sci. USA 88:5072–5076 (1991)).

At present, however, the utility of the lacR/O-based systems in eucaryotic cells is limited since the inducer isopropyl.β-thiogalactopyranoside (IPTG), despite its rapid uptake and intracellular stability (Wyborski & Short, Nucleic Acids Res. 19:4647–4653), acts rather slowly and inefficiently, resulting in only moderate induction. Nevertheless, an interesting conditional mutant of a lacR-VP16 fusion has been described (Baim et al., Proc. Natl. Acad. Sci. USA 88:5072–5076 (1991)). It activates a minimal promoter~1000-fold at elevated temperatures in the presence of IPTG. The temperature dependence and the inherent IPTG-related problems, however, may also limit this approach.

SUMMARY OF THE INVENTION

This invention features a system for regulating expression of eucaryotic genes using components of the Tet repressor/operator/inducer system of prokaryotes. In the system of the invention, transcription of a nucleotide sequence operably linked to at least one tet operator sequence is stimulated by a tetracycline (Tc)-controllable transcriptional activator fusion protein (referred to herein as tTA). The tTA is comprised of two polypeptides. The first polypeptide is a Tet repressor (TetR; e.g., a Tn10-derived TetR), which binds to tet operator sequences in the absence but not the presence of Tc. The second polypeptide directly or indirectly activates transcription in eucaryotic cells. For example, the second polypeptide can be a transcriptional activation domain from herpes simplex virus virion protein 16 or another transcriptional activating domain, e.g. acidic, proline-rich, serine/threonine-rich, glutamine-rich. Alternatively, the second polypeptide can be a domain (e.g., a dimerization domain) which recruits a transcriptional activator (e.g., an endogenous transcriptional activator) to interact with the tTA fusion protein by a protein—protein interaction (e.g., a non-covalent interaction). In the absence of Tc or a Tc analogue, transcription of a gene operably linked to a tTA-responsive promoter (typically comprising at least one tet operator sequence and a minimal promoter) is stimulated by a tTA of the invention, whereas in the presence of Tc or a Tc analogue, transcription of the gene linked to the tTA-responsive promoter is not stimulated by the tTA.

As described herein, this system functions effectively in transgenic animals. Accordingly, the invention provides a tetracycline-controllable regulatory system for modulating gene expression in transgenic animals. Additionally, the invention provides targeting vectors for homologous recombination that enable the components of the regulatory system to be integrated at a predetermined location in the genome of a host cell or animal. This embodiment of the invention is able to solve a longstanding problem in the field generally described as gene targeting or gene knock out. Constitutive disruption of certain genes has been found to produce lethal mutations resulting in death of homozygous embryos, e.g., as described for the knock out of the RB gene (lacks, T. et al. (1992) Nature 359:295–300). This problem precludes the development of "knock out" animals for many genes of interest. The regulatory system of the invention can be applied to overcome this problem. DNA encoding a tTA of the invention can be integrated within a gene of interest such that expression of the tTA is controlled by the endogenous regulatory elements of the gene of interest (e.g., the tTA is expressed spatially and temporally in a manner similar to the gene of interest). The gene of interest is then operably linked to at least one tet operator sequence (either at its endogenous site by homologous recombination or a second copy of the gene of interest, linked to tet operator(s), can be integrated at another site). Expression of the tet-operator linked gene is thus placed under the control of the tTA, whose pattern of expression mimics that of the gene of interest. In the absence of Tc, expression of the tet operator-linked gene of interest is stimulated by the tTA and the animal develops like a nonmutated wildtype animal. Then, at a particular stage of development, expression of the gene of interest can be switched off by raising the level of Tc (or a Tc analogue) in the circulation and the tissues of the animal by feeding or injecting Tc (or a Tc analogue) to the animal, thereby inhibiting the activity of the tTA and ascription of the gene of interest. This method is generally referred to herein as a "conditional knockout".

Accordingly, one aspect of the invention relates to targeting vectors for homologous recombination. In one embodiment, the invention provides an isolated DNA molecule for integrating a polynucleotide sequence encoding a tetracycline-controllable transactivator (tTA) at a predetermined location in a second target DNA molecule. In this DNA molecule, a polynucleotide sequence encoding a tTA is flanked at 5' and 3' ends by additional polynucleotide sequences of sufficient length for homologous recombination between the DNA molecule and the second target DNA molecule at a predetermined location. Typically, the target DNA molecule into which the tTA-coding sequences are integrated is a gene of interest, or regulatory region thereof, in a eucaryotic chromosome in a host cell. For example, tTA-coding sequences can be inserted into a gene within a yeast, fungal, insect or mammalian cell. Additionally, tTA-coding sequences can be inserted into a viral gene present within a host cell, e.g. a baculovirus gene present in insect host cell. In a preferred embodiment, integration of the tTA-encoding sequences into a predetermined location in a gene of interest (by homologous recombination) places the tTA-coding sequences under the control of regulatory elements of the gene of interest (e.g., 5' flanking regulatory elements), such that the tTA is expressed in a spatial and temporal manner similar to the gene of interest.

In another embodiment of the targeting vector for homologous recombination, the isolated DNA molecule permits integration of a polynucleotide sequence encoding both a tTA and a tTA-responsive promoter within a predetermined gene of interest in a second target DNA molecule (a "single hit vector", schematically illustrated in FIG. 13A–B). This molecule includes: 1) a first polynucleotide sequence comprising a 5' flanking regulatory region of the gene of interest, operably linked to 2) a second polynucleotide sequence encoding a tTA; and 3) a third polynucleotide sequence comprising a tTA-responsive promoter, operably linked to: 4) a fourth polynucleotide sequence comprising at least a portion of a coding region of the gene of interest. The first and fourth polynucleotide sequences are of sufficient length for homologous recombination between the DNA molecule and the gene of interest such that expression of the tTA is controlled by 5' regulatory elements of the gene of interest and expression of the gene of interest is controlled by the tTA-responsive promoter (i.e., upon binding of the tTA to the tTA-responsive promoter, expression of the gene of interest is stimulated). This targeting vector can also include a polynucleotide sequence encoding a selectable marker operably linked to a regulatory sequence. Typically, the selectable marker expression unit is located between the tTA-encoding sequence (i.e., the second polynucleotide sequence described above) and the tTA-responsive promoter (i.e., the third polynucleotide sequence described above). Additionally or alternatively, this targeting vector can also include a sequence, typically located upstream (i.e., 5') of the tTA-responsive promoter (e.g., between the selectable marker expression unit and the tTA responsive promoter) which terminates transcription or otherwise insulated downstream elements from the effects of upstream regulatory elements. The tTA-responsive promoter typically includes a minimal promoter operably linked to at least one tet operator sequence. The minimal promoter is derived, for example, from a *cytomegalovirus* immediate early gene promoter or a herpes simplex virus thymidine kinase gene promoter.

Another aspect of the invention relates to eucaryotic host cells containing a DNA molecule encoding a tTA integrated at a predetermined location in a second target DNA molecule (e.g., a gene of interest) in the host cell. Such a eucaryotic host cell can be created by introducing a targeting vector of the invention into a population of cells under conditions suitable for homologous recombination between the DNA encoding the tTA and the second target DNA molecule and selecting a cell in which the DNA encoding the tTA has integrated at a predetermined location within the second target DNA molecule. The host cell can be a mammalian cell (e.g., a human cell). Alternatively, the host cell can be a yeast, fungal or insect cell (e.g., the tTA-encoding DNA can be integrated into a baculovirus gene within an insect cell). A preferred host cell type for homologous recombination is an embryonic stem cell, which can then be used to create a non-human animal carrying tTA-coding sequences integrated at a predetermined location in a chromosome of the animal. A host cell can further contain a gene of interest operably linked to a tTA-responsive transcriptional promoter. The gene of interest operably linked to the tTA-responsive promoter can be integrated into DNA of the host cell either randomly (e.g., by introduction of an exogenous gene) or at a predetermined location (e.g., by targeting an endogenous gene for homologous recombination). The gene linked to the tTA-responsive promoter can be introduced into the host cell independently from the DNA encoding the tTA, or alternatively, a "single hit" targeting vector of the invention can be used to integrate both tTA-coding sequences and a tTA-responsive promoter into a predetermined location in DNA of the host cell. Expression of a gene of interest operably linked to a tTA-responsive promoter in a host cell of the invention can be inhibited by contacting the cell with tetracycline or a tetracycline analogue.

Another aspect of the invention relates to non-human transgenic animals having a transgene comprising a polynucleotide sequence encoding a tetracycline-controllable transactivator (tTA) of the invention or having a transgene encoding a gene of interest operably linked to a tTA-responsive promoter. Double transgenic animals having both transgenes (i.e., a tTA-coding transgene and a gene of interest linked to a tTA-responsive promoter) are also encompassed by the invention. In one embodiment, the transgenic animal is a mouse. In other embodiments, the transgenic animal is a cow, a goat, a sheep and a pig. Transgenic animals of the invention can be made, for example, by introducing a DNA molecule encoding the tTA or the gene of interest operably linked to a tTA responsive promoter into a fertilized oocyte, implanting the fertilized oocyte in a pseudopregnant foster mother, and allowing the fertilized oocyte to develop into the non-human transgenic animal to thereby produce the non-human transgenic animal. Double transgenic animals can be created by appropriate mating of single transgenic animals. Expression of a gene of interest operably linked to a tTA responsive promoter in a double transgenic animal of the invention can be inhibited by administering tetracycline or a tetracycline analogue to the animal.

Another aspect of the invention relates to non-human transgenic animals having a transgene encoding a tTA of the invention, wherein the transgene is integrated by homologous recombination at a predetermined location within a chromosome within cells of the animal (also referred to herein as a homologous recombinant animal). The homologous recombinant animal can also have a second transgene encoding a gene of interest operably linked to a tTA-responsive promoter. The second transgene can be introduced randomly or, alternatively, at a predetermined location within a chromosome (e.g., by homologous recombination. For example, a single hit vector of the invention can be used to create a homologous recombinant animal in which expression of the tTA is controlled by 5' regulatory elements of a gene of interest and expression of the gene of interest is controlled by the tTA-responsive promoter (such that in the absence of Tc, expression of the gene is stimulated by tTA binding to the tTA responsive promoter).

A non-human transgenic animal of the invention having tTA-coding sequences integrated at a predetermined location within chromosomal DNA of cells of the animal can be created by introducing a targeting vector of the invention into a population of embryonic stem cells under conditions suitable for homologous recombination between the DNA encoding the tTA and chromosomal DNA within the cell, selecting an embryonic stem cell in which DNA encoding the tTA has integrated at a predetermined location within the chromosomal DNA of the cell, implanting the embryonic stem cell into a blastocyst, implanting the blastocyst into a pseudopregnant foster mother and allowing the blastocyst to develop into the non-human transgenic animal to thereby produce the non-human transgenic animal.

Another aspect of the invention relates to a process for producing and isolating a gene product (e.g., protein) encoded by a gene of interest operably linked to a tTA-responsive transcriptional promoter in a host cell of the invention carrying tTA-coding sequences. In the process, a host cell is first grown in a culture medium in the presence of tetracycline or a tetracycline analogue (under these conditions, expression of the gene of interest is not stimulated). Next, the concentration of tetracycline or the tetracycline analogue in the culture medium is reduced to stimulate transcription of the gene of interest. The cells are further cultured until a desired amount of the gene product encoded by the gene of interest is produced by the cells. Finally, the gene product is isolated from harvested cells or from the culture medium. Preferred cells for use in the process include yeast or fungal cells.

Kits containing the components of the regulatory system of the invention described herein are also within the scope of the invention.

Various additional features, components and aspects of this invention are described in further detail below.

BRIEF DESCRIPTION OF THE FIGURES

FIG. 1A–1B. Schematic representation of tetR-VP16 fusion proteins (tTAs), encoded by plasmids pUHD15-1 and pUHD151-1, and a tTA-dependent transcription unit, encoded by plasmid pUHC13-3.

Panel a: Diagrammatic representation of two tTA proteins. In both fusion proteins, tTA and tTA$_S$, the original 207-amino-acid sequence of tetR is conserved. Two versions of VP 16 sequences encoding the activation domain were fused in frame to the 3' end of the tetR gene, resulting in tTA and tTAs. The bold letters indicate the original amino acids at the N terminal end, the junction (SEQ ID NOs: 11 and 12), and the C-terminal end of the fusion proteins (SEQ ID NO: 13); the other letters designate amino acids introduced due to sequence constraints of the particular system. The numbers delineate amino acid positions within tetR (Hillen and Wissman in Protein-Nucleic Acid Interaction, Topics in Molecular and Structural Biology, Saenger and Heinemann (eds.), Vol 10, pp. 143–162 (1989)) or VP16 (Treizenberg et al., Genes Dev. 2:718–729 (1988)), respectively.

Panel b: The tTA-dependent transcriptional unit consists of the simian virus 40 (SV40) poly(A) site (An), the luciferase gene (luc), the $P_{hCMV}$*-1 or $P_{hCMV}$*-2. The two promoters encompass the sequence between +75 and −53 of the $P_{hCMV}$*-2 with one base-pair exchange at −31, which creates a Stu I cleavage site (SEQ ID NO: 15). The Xho I site (SEQ ID NO: 16) introduced at −53 by PCR was utilized to insert the heptamerized tetO sequence (SEQ ID NOs: 14 and 17). This heptameric sequence is flanked at one side by an 18-nucleotide polylinker, which allows the insertion of the operators in both orientations as Sal 1/Xhol fragments. The position of the central G/C base pair of the promoter proximal operator to position +1 is −95 for $P_{hCMV}$*-1 (upper construct) and −76 for $P_{hCMV}$*-2 (lower construct). The plasmids that contain the four constructs are indicated on the far right.

Figures 2A, 2B:
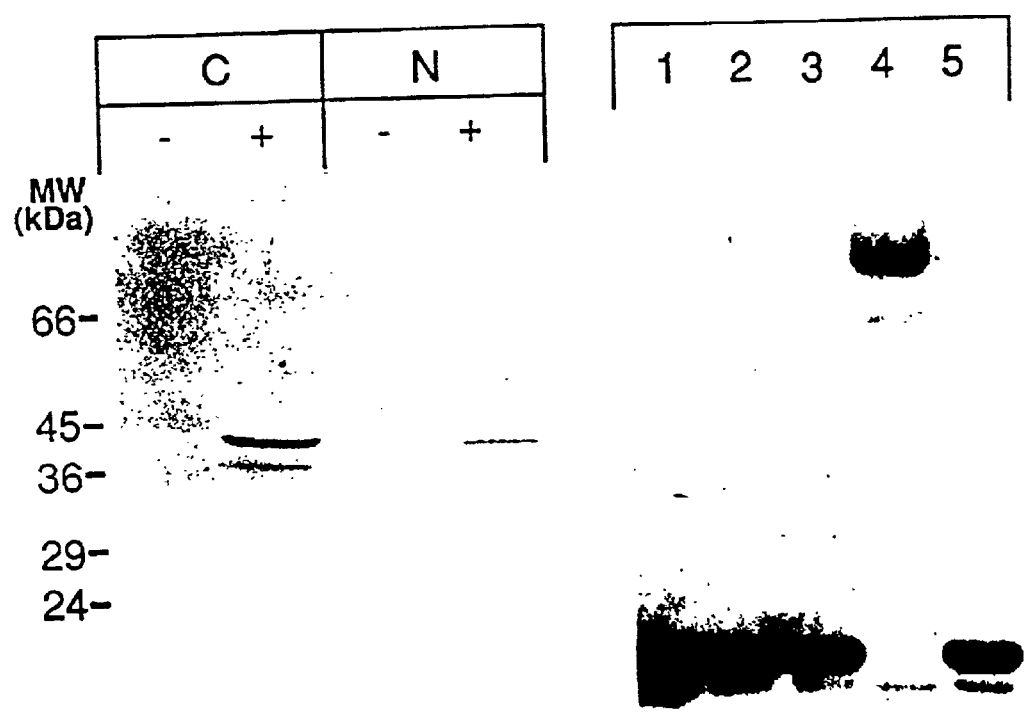

FIG. 2A–2B. Western blots showing the identification and characterization of tTA produced in HeLa cells. HeLa cells grown to 40% confluency were transiently transfected with pUHD15-1 by the calcium phosphate method. Nuclear and cytoplasmic extracts were prepared after 36 hr.

FIG. 2A; Western blot analysis of electrophoretically separated extracts (6% acrylamide/0.1% SDS gels) with tetR-specific antibodies reveals a protein of about 37 kDa (tTA) in cytoplasmic (C) and nuclear (N) extracts in pUHD15-1 transfected cells (+) that is not present in mock-transfected cells (−).

FIG. 2B; Mobility change of tetO DNA by tTA binding from HeLa cell nuclear extracts. Radioactively labeled tetO DNA was mixed with extracts from mock-transfected (lanes 2 and 3) and pUHD15-1-transfected (lanes 4 and 5) HeLa cells in the absence (lanes 2 and 4) and presence (lanes 3 and 5) of 1 µg of tetracycline per ml (added 2 min prior to the addition of the operator). Lane 1 contains labeled operator DNA only.

Figure 3B:
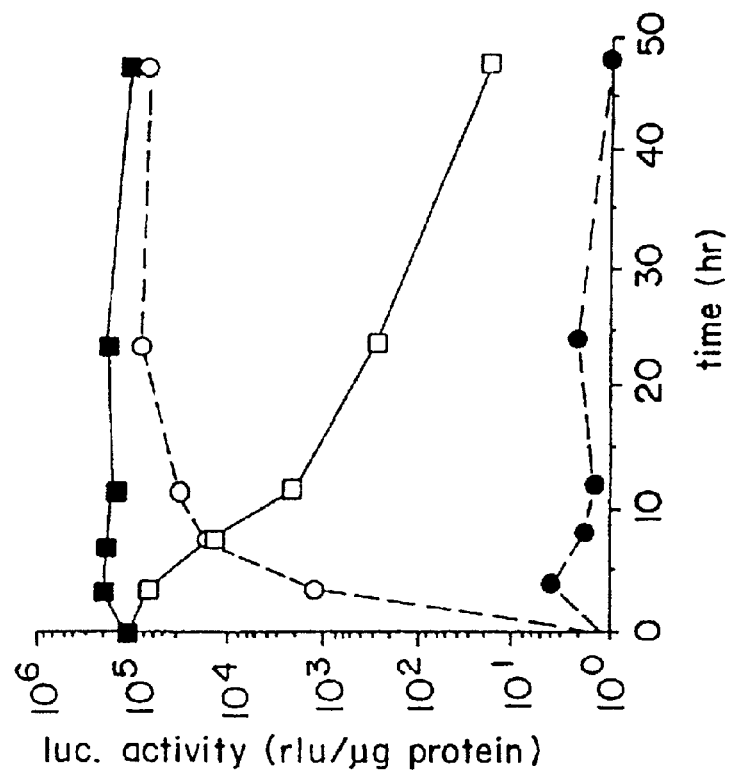
Figure 3A:
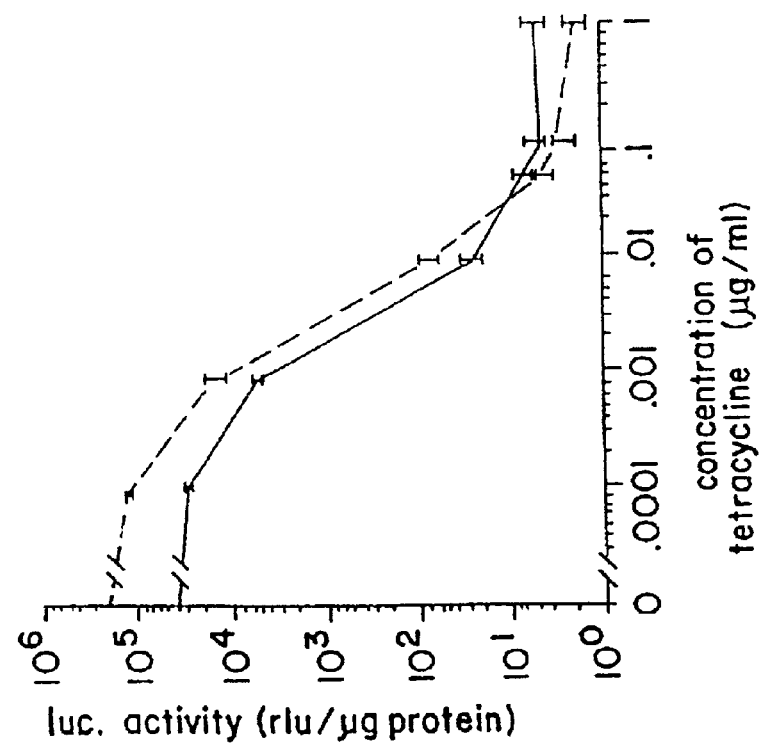

FIG. 3A–3B. Graphs showing the dependence of tTA function on tetracycline.

FIG. 3A; Dependence of luciferase (luc.) activity on tetracycline concentration. HeLa cell clones X1 (dashed line) and T12 previously grown in tetracycline-free medium were seeded with a density of 5000 cells per 35 mm dish and incubated at the tetracycline concentrations indicated. After reaching ~90% confluency, cells were harvested and assayed for luciferase activity. Data given are the means±SD of three independent experiments.

FIG. 3B; Kinetics of tetracycline action. X1 cells were grown in 100 mm dishes to ~80% confluency in the absence or presence (0.1 µg/ml) of tetracycline. At time 0, cells were washed with phosphate-buffered saline and split into smaller culture dishes (½₀th of the initial cultures per 35 mm dish). Half of the cultures remained in tetracycline-free medium (□) and the other half were incubated in the presence of tetracycline (1 µg/ml; ■). The X1 culture grown in tetracycline-containing medium was split in the same manner, one half was further incubated in the presence of tetracycline (○), whereas the other half was transferred to tetracycline-free medium (●). At the times indicated, aliquots were harvested and examined for luciferase activity. The slight increase in luciferase activity monitored at 4 hr in the culture containing tetracycline (○) is reproducible and reflects luciferase induction during the washing step.

FIG. 4A–4D. [SEQ ID NO: 1] The polynucleotide sequence coding for tTA transactivator.

FIG. 5A–5D. [SEQ ID NO: 3] The polynucleotide sequence coding for tTA$_S$ transactivator.

FIG. 6. [SEQ ID NO: 5] The polynucleotide sequence of $P_{hCMV}$*-1. The nucleotide sequence shown encompasses the tet operator sequences (italics) and the hCMV minimal promoter, of which position −53, the TATA box and position +75 (relative to the transcription start site) are underlined.

FIG. 7. [SEQ ID NO: 6] The polynucleotide sequence of $P_{hCMV}^*$-2. The nucleotide sequence shown encompasses the tet operator sequences (italics) and the hCMV minimal promoter, of which position −53, the TATA box and position +75 (relative to the transcription start site) are underlined.

FIG. 8. [SEQ ID NO: 7] The polynucleotide sequence of PTk*-1. The nucleotide sequence shown encompasses the tet operator sequences (italics) and the HSV-Tk minimal promoter, of which position −81, the TATA box and position +7 (relative to the transcription start site) are underlined.

FIG. 9A–9H. [SEQ ID NO: 8] The polynucleotide sequence of the cDNA coding for the rabbit progesterone receptor under control of $P_{hCMV}^*$-1

FIG. 10A–10F. [SEQ ID NO: 9] The polynucleotide sequence of the cDNA coding for the rabbit progesterone receptor under control of $P_{hCMV}^*$-1

Figure 11:
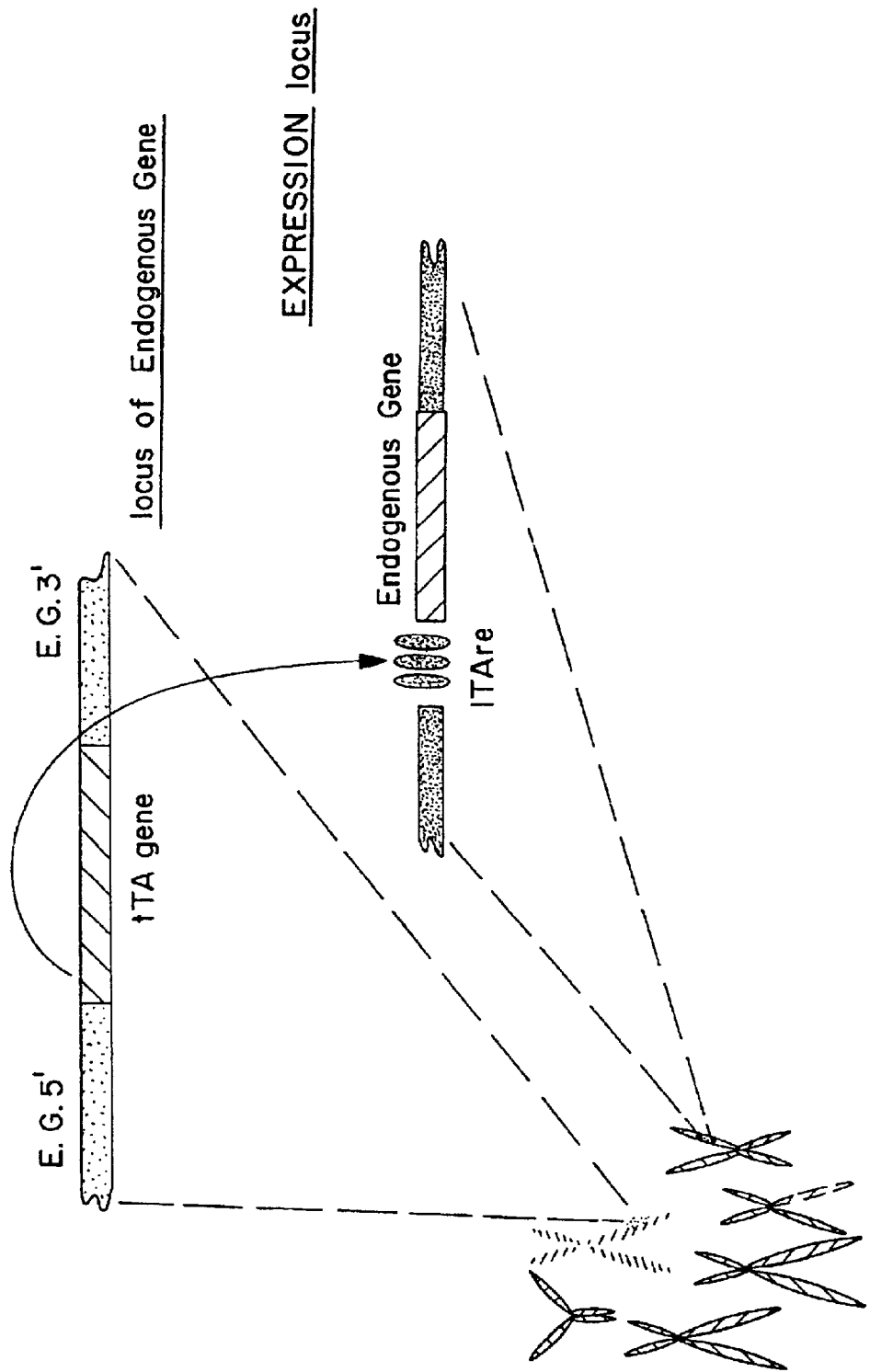

FIG. 11. A schematic representation of Conditional Knock Out Strategy 1 in which "E.G. 5'" represents flanking nucleotide sequence from 5' of the coding sequence for an Endogenous Gene; "E.G. 3'" represents flanking nucleotide sequence from 3' of the coding sequence for an Endogenous Gene; and "tTARE" represents a tTA responsive element inserted just upstream of a copy of the endogenous gene of interest. (In other embodiments the gene linked to the tTA is a heterologous gene.)

Figure 12:
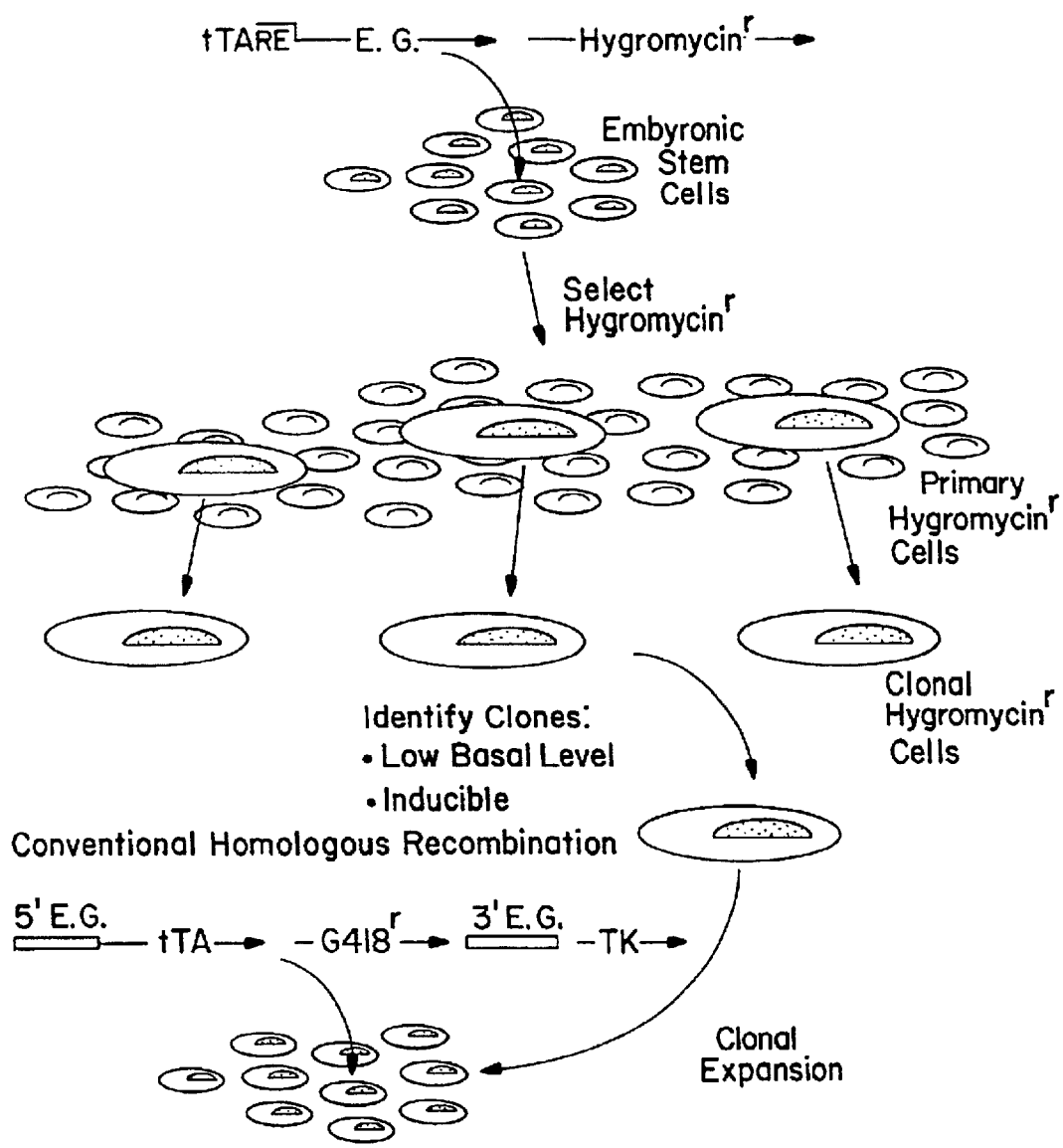

FIG. 12. A schematic representation of Conditional Knock Out Strategy 2 in which "tTARE" is a tTA responsive promoter element: "E.G". is an endogenous gene; "E.G. 5'" represents flanking nucleotide sequence from 5' of the coding sequence for an Endogenous Gene; "E.G. 3'" represents flanking nucleotide sequence from 3' of the coding sequence for an Endogenous Gene; and "TK" is a thymidine kinase gene.

FIG. 13A–B. A schematic representation of Conditional Knock Out Strategy 3 depicting vector designs in which abbreviations are as defined above, Neo$^r$ is a neomycin resistance gene and pPGK is phosphoglycerate kinase sequence.

Figure 14:
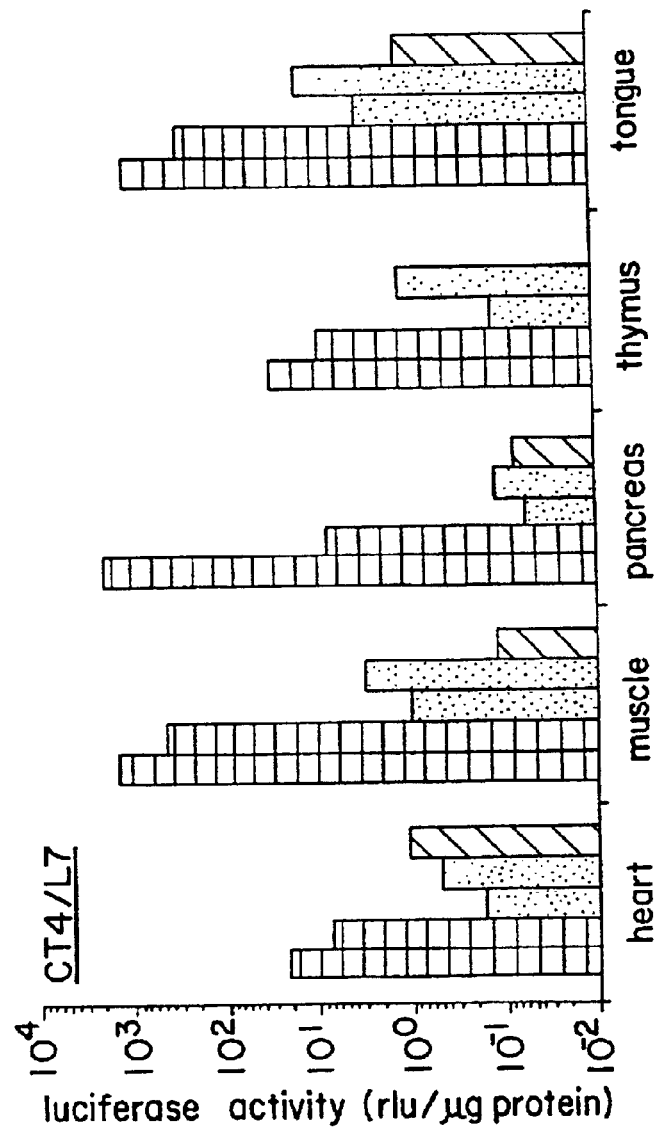

FIG. 14. A graphic representation of the doxycycline dependent luciferase activity in double transgenic mice carrying $P_{hCMV}$-tTA and $P_{hCMV}^*$-1-luc transgenes. Light bars show tTA-activated luciferase levels in different tissues from 2 individual mice. Dark bars show luciferase levels in different tissues from 2 individual mice that received doxycycline in the drinking water (200 mg/ml, 5% sucrose) for 7 days. Spotted bars (controls) represent the average luciferase background activity from 5 individuals from line L7, carrying only the $P_{hCMV}^*$-1-luc transgene.

DETAILED DESCRIPTION OF THE INVENTION

Definitions

The description that follows makes use of a number of terms used in recombinant DNA technology. In order to provide a clear and consistent understanding of the specification and claims, including the scope to be given such terms, the following definitions are provided.

Cloning Vector. A plasmid or phage DNA or other DNA sequence which is able to replicate autonomously in a host cell, and which is characterized by one or a small number of restriction endonuclease recognition sites at which such DNA sequences may be cut in a determinable fashion without loss of an essential biological function of the vector, and into which a DNA fragment may be spliced in order to bring about its replication and cloning. The cloning vector may further contain a marker suitable for use in the identification of cells transformed with the cloning vector.

Expression Vector. A vector similar to a cloning vector but which is capable of enhancing the expression of a gene which has been cloned into it, after transformation into a host. The cloned gene is usually placed under the control of (i.e., operably linked to) certain control sequences such as promoter sequences. Promoter sequences may be either constitutive or inducible.

Eucaryotic Host Cell. According to the invention, a eucaryotic host cell may be any such cell which include, but are not limited to, yeast cells, plant cells, fungal cells, insect cells, e.g. Schneider and sF9 cells, mammalian cells, e.g. HeLa cells (human), NIH3T3 (murine), RK 13 (rabbit) cells, embryonic stem cell lines, e.g, D3 and J1, and cell types such as hematopoietic stem cells, myoblasts, hepatocytes, lymphocytes, airway epithelium and skin epithelium.

Recombinant Eucaryotic Host. According to the invention, a recombinant eucaryotic host may be any eucaryotic cell which contains the polynucleotide molecules of the present invention on an expression vector or cloning vector. This term is also meant to include those eucaryotic cells that have been genetically engineered to contain the desired polynucleotide molecules in the chromosome, genome or episome of that organism. Thus, the recombinant eucaryotic host cells are capable of stably or transiently expressing the proteins.

Recombinant vector. Any cloning vector or expression vector which contains the polynucleotide molecules of the invention.

Host. Any prokaryotic or eucaryotic cell that is the recipient of a replicable vector. A "host" as the term is used herein, also includes prokaryotic or eucaryotic cells that can be genetically engineered by well known techniques to contain desired gene(s) on its chromosome or genome. For examples of such hosts, see Sambrook et al., Molecular Cloning: A Laboratory Manual, Second Edition, Cold Spring Harbor Laboratory, Cold Spring Harbor, N.Y. (1989).

Promoter. A DNA sequence generally described as the 5' region of a gene, located proximal to the start codon. The transcription of an adjacent gene(s) is initiated at the promoter region. If a promoter is an inducible promoter, then the rate of transcription increases in response to an inducing agent. In contrast, the rate of transcription is not regulated by an inducing agent if the promoter is a constitutive promoter.

Minimal Promoter. A partial promoter sequence which defines the transcription start site but which by itself is not capable, if at all, of initiating transcription efficiently. The activity of such minimal promotors depend on the binding of activators such as a tetracycline-controlled transactivator to operably linked binding sites.

Gene. A DNA sequence that contains information needed for expressing a polypeptide or protein.

Structural Gene. A DNA sequence that is transcribed into messenger RNA (mRNA) that is then translated into a sequence of amino acids characteristic of a specific polypeptide.

Polynucleotide molecules. A polynucleotide molecule may be a polydeoxyribonucleic acid molecule (DNA) or a polyribonucleic acid molecule (RNA).

Complementary DNA (cDNA). A "complementary DNA" or "cDNA" gene includes recombinant genes synthesized by reverse transcription of mRNA and from which intervening sequences (introns) have been removed.

Expression. "Expression" is the process by which a polypeptide is produced from a structural gene. The process involves transcription of the gene into mRNA and the translation of such mRNA into polypeptide(s).

Fragment. A "fragment" of a molecule is meant to refer to any polypeptide subset of that molecule.

Tet repressor. A "tet repressor" refers to a prokaryotic protein which binds to a tet operator sequence in the absence but not the presence of tetracycline. The term "tet repressor" is intended to include repressors of different class types, e.g., class A, B, C, D or E tet repressors.

Tetracycline Analogue. A "tetracycline analogue" is any one of a number of compounds that are closely related to tetracycline (Tc) and which bind to the tet repressor with a Ka of at least about $10^6$ M$^{-1}$. Preferably, the tetracycline analogue binds with an affinity of about $10^9$ M$^{-1}$ or greater, e.g. $10^9$M$^{-1}$. Examples of such tetracycline analogues include, but are not limited to those disclosed by Hlavka and Boothe, "The Tetracyclines," in Handbook of Experimental Pharmacology 78, R. K. Blackwood et al. (eds.), SpringerVerlag, Berlin-N.Y., 1985; L. A. Mitscher "The Chemistry of the Tetracycline Antibiotics, Medicinal Research 9, Dekker, New York, 1978; Noyee Development Corporation, "Tetracycline Manufacturing Processes," Chemical Process Reviews, Park Ridge, N.J., 2 volumes, 1969; R. C. Evans, "The Technology of the Tetracyclines," Biochemical Reference Series 1, Quadrangle Press, New York, 1968; and H. F. Dowling, "Tetracycline," Antibiotics Monographs, no. 3, Medical Encyclopedia, New York, 1955; the contents of each of which are fully incorporated by reference herein. Examples of tetracycline analogues include anhydrotetracycline, doxycycline, chlorotetracycline, epioxytetracycline, cyanotetracycline and the like. Certain Tc analogues, such as anhydrotetracycline and epioxytetracycline, have reduced antibiotic activity compared to Tc.

Transgenic Animal. A transgenic animal is an animal having cells that contain a transgene, wherein the transgene was introduced into the animal or an ancestor of the animal at a prenatal, e.g., an embryonic, stage. A transgene is a DNA which is integrated into the genome of a cell from which a transgenic animal develops and which remains in the genome of the mature animal, thereby directing the expression of an encoded gene product in one or more cell types or tissues of the transgenic animal. Non-human animals into which transgenes can be introduced by techniques known in the art include mice, goats, sheep, pigs, cows and other domestic farm animals.

A transgenic animal can be created, for example, by introducing a nucleic acid encoding a protein of interest (typically linked to appropriate regulatory elements, such as a constitutive or tissue-specific enhancer) into the male pronuclei of a fertilized oocyte, e.g., by microinjection, and allowing the oocyte to develop in a pseudopregnant female foster animal. Intronic sequences and polyadenylation signals can also be included in the transgene to increase the efficiency of expression of the transgene. Methods for generating transgenic animals, particularly animals such as mice, have become conventional in the art and are described, for example, in U.S. Pat. Nos. 4,736,866 and 4,870,009 and Hogan, B. et al., (1986) *A Laboratory Manual*, Cold Spring Harbor, N.Y., Cold Spring Harbor Laboratory. A transgenic founder animal can be used to breed additional animals carrying the transgene. A transgenic animal carrying one transgene can further be bred to another transgenic animal carrying a second transgenes to create a so-called "double transgenic" animal carrying two transgenes.

Homologous Recombinant Animal. The term "homologous recombinant animal" as used herein is intended to describe an animal containing a gene which has been modified by homologous recombination between the gene and a DNA molecule introduced into an embryonic cell of the animal, or ancestor thereof. Thus, a homologous recombinant animal is a type of transgenic animal in which the transgene is introduced into a predetermined chromosomal location in the genome of the animal by homologous recombination.

To create such a homologous recombinant animal, a vector is prepared which contains DNA of interest (e.g., encoding a tTA of the invention) flanked at its 5' and 3' ends by additional nucleic acid of a eucaryotic gene of interest at which homologous recombination is to occur. The flanking nucleic acid is of sufficient length for successful homologous recombination with the eucaryotic gene. Typically, several kilobases of flanking DNA (both at the 5' and 3' ends) are included in the vector (see e.g., Thomas, K. R. and Capecchi, M. R. (1987) *Cell* 51:503 for a description of homologous recombination vectors). The vector is introduced into an embryonic stem cell line (e.g., by electroporation) and cells in which the introduced DNA has homologously recombined with the endogenous DNA are selected (see e.g., Li, E. et al. (1992) *Cell* 62:915). The selected cells are then injected into a blastocyst of an animal (e.g., a mouse) to form aggregation chimeras (see e.g., Bradley, A. in *Teratocarcinomas and Embryonic Stem Cells: A Practical Approach*, E. J. Robertson, ed. (IRL, Oxford, 1987) pp. 113–152). A chimeric embryo can then be implanted into a suitable pseudopregnant female foster animal and the embryo brought to term. Progeny harbouring the homologously recombined DNA in their germ cells can be used to breed animals in which all cells of the animal contain the homologously recombined DNA by so-called "germline transmission". Animals carrying the recombined gene can be bred to homozygosity and/or bred with other animals carrying other transgenes.

Recombinant expression of proteins is commonly done using constitutive promoters like human CMV (Boshart, M. et al. 1985, Cell Vol. 41, 521–530) or the adenovirus major late promoter or SV40 early promoter as described below (see also, e.g., Kaufman, R. J. 1990 Meth Enzymol. Vol. 185: 537–566 and Benoist C. et al. (1981) Nature Vol. 290:304 ff). However, in the case of proteins such as certain proteases, cytotoxic or cytostatic proteins that interfere with the cell membranes or proteins like certain receptors, whose normal biological function triggers a response to the host cell environment (media components, temperature etc.) that is detrimental to the host cell, expression of the proteins may negatively effect the physiology of the host cell. In other cases overexpression of a desired gene may simply be unduly taxing for the producing cells. In such cases it is desirable to inhibit the expression of the desired gene until an optimal cell density has been achieved, and only then, after an optimal period of cell culture in vitro or cell growth and development in vivo (determined empirically), induce gene expression in the cells to produce sufficient quantities of the protein. While a number of systems have been proposed and tried (as generally reviewed by Yarranton, G. T. 1992 Current Opinion in Biotechnology Vol. 3:506–511) many such systems do not allow for tight repression and subsequent complete activation. Others employ impractical activation steps that are not expected to be useful in large scale fermentation or in whole animals. The current invention however fulfills all these criteria in eucaryotic expression systems using a transcriptional switch based on procaryotic control elements.

Aspects of the tightly regulatable genetic switch used in this invention for controlling gene transcription are described in Gossen & Bujard, 1992, Proc. Natl. Acad. Sci. USA 89:55475551 and in U.S. patent application Ser. No. 08/076,726, entitled "Tight Control of Gene Expression in Eucaryotic Cells by Tetracycline-responsive Promoters" filed 14 Jun. 1993, the full contents of both of which are incorporated herein by reference.

The genetic switch employed in this invention comprises two components: (i) a polynucleotide (e.g. DNA) moiety encoding a tetracycline-controllable transcriptional activator (also referred to herein as a "transactivator" or tTA) and (ii) a gene of interest operably linked to, i.e., under the transcriptional control of, a promoter responsive to the transcriptional activator.

The tetracycline-controllable transactivator (tTA) is composed of a procaryotic tet repressor (tetR) (also referred to as the first polypeptide) operably linked to a polypeptide which directly or indirectly activates transcription in eucaryotic cells (also referred to as the second polypeptide). Typically, nucleotide sequences encoding the first and second polypeptides are ligated to each other in-frame to create a chimeric gene encoding a fusion protein, although the first and second polypeptides can be operably linked by other means that preserve the function of each polypeptide (e.g., chemically crosslinked). In one embodiment, the second polypeptide is a transcriptional activating protein such as the acidic transactivating domain of virion protein 16 (VP 16) of herpes simplex virus (HSV) as in plasmids pUHD15-1 or pUHD151-1 (see FIG. 11). It should be appreciated that other transactivators, including acidic, proline- or serine/threonine- or glutamine-rich transactivating moieties as described below, may be substituted for the VP 16 transactivator in the tetracycline-controllable fusion transactivator. In this embodiment, the second polypeptide of the fusion protein is capable of directly activating transcription.

In another embodiment, the second polypeptide of the tTA fusion protein indirectly activates transcription by recruiting a transcriptional activator to interact with the tetR fusion protein. For example, tetR can be fused to a polypeptide domain (e.g., a dimerization domain) capable of mediating a protein—protein with a transcriptional activator protein, such as an endogenous activator present in a host cell. It has been demonstrated that functional associations between DNA binding domains and transactivation domains need not be covalent (see e.g., Fields and Song (1989) Nature 340:245–247; Chien et al. (1991) Proc. Natl. Acad. Sci. USA 88:9578–9582; Gyuris et al. (1993) Cell 75:791–803; and Zervos, A. S. (1993) Cell 72:223–232). Accordingly, the second polypeptide of the tTA fusion protein may not directly activate transcription but rather may form a stable interaction with an endogenous polypeptide bearing a compatible protein—protein interaction domain and transactivation domain. Examples of suitable interaction (or dimerization) domains include leucine zippers (Landschulz et al. (1989) Science 243:1681–1688), helix-loop-helix domains (Murre, C. et al. (1989) Cell 58:537–544) and zinc finger domains (Frankel, A. D. et al. (1988) Science 240:70–73). Interaction of a dimerization domain present in the tTA fusion protein with an endogenous nuclear factor results in recruitment of the transactivation domain of the nuclear factor to the tTA, and thereby to a tet operator sequence to which the tTA is bound.

A variation of this approach is to construct a fusion of the tetR DNA binding sequence to the non-DNA binding amino acid sequences of the TATA binding protein (TBP) (TBP is described in Kao, C. C. et al. (1990) Science 248:1646–1650). The DNA binding form of TBP is part of a protein complex designated TFIID. The function of TBP in the complex is to recruit other protein components of the TFIID complex to position near the transcription initiation site of eucaryotic genes containing a TATA box (i.e., TBP binding site). When bound to the TATA box, the TFIID complex subsequently mediates the sequential recruitment of other members of the basic transcriptional initiation complex, resulting in initiation of transcription (described in more detail in Buratowski, S. et al. (1989) Cell 56:549–561). Accordingly, when fused to tetR DNA binding sequences, TBP may recruit other members of the basic transcription initiation complex to DNA sequences containing a tet operator(s). Furthermore, by substituting a TATA sequence present in a eukaryotic gene of interest with a tet operator(s), the tetR/TBP fusion protein can be targeted to this site in a manner dependent on the presence or absence of Tc (or analogue thereof), resulting in Tc-dependent initiation of transcription. Since, in this approach, the gene of interest to be regulated by the tTA (i.e., tetR/TBP fusion protein) lacks a functional TATA element, the basal level of expression of the gene in the presence of Tc (or analogue) is expected to be very low. However, upon removal of Tc (or analogue), transcription initiation is restored via binding of tetR/TBP to the tet operator(s) and recruitment of other components of the transcription initiation complex.

The tTA may be expressed in a desired host cell using otherwise conventional methods and materials by transfecting or transforming the host cell with the tTA-encoding DNA operably linked to a conventional promoter (such as are mentioned elsewhere herein), e.g. for constitutive expression.

The second component of the genetic switch is the tTA-responsive transcriptional promoter to which the gene of interest is operably linked. The promoter may be a minimal promoter comprising, for example, a portion of the *cytomegalovirus* (CMV) IE promoter, operably linked to at least one tet operator sequence, derived for example from the tetracycline resistance operon encoded in Tn10 of *E. coli* (Hillen & Wissmann, "Topics in Molecular and Structural biology" in Protein-Nucleic Acid Interaction, Saeger & Heinemannn eds., Macmillan, London, 1989, Vol. 10, pp. 143–162), to serve as target sequences for a tTA.

Other suitable minimal promoters include PhCMV*-1, PhCMV*-2, and PtK*-1, described herein, or other minimal promoters derived from promoter elements typically used in the cell line employed as described in the references throughout this application.

Minimal promoter elements particularly useful for a given cell line may be selected from a series of deletion mutants of the original promoter nucleotide sequence, based on the ability of a given member of the series (for instance, placed as a XhoI/SacII fragment into the corresponding restriction sites of plasmid pUHC13-3) to be activated in transient transfection experiments using a cell line stably expressing the tetR-VP 16 fusion protein; as will be appreciated a cell line stably expressing any other fusion of tetR with a protein domain capable of activating transcription (see below) can be used. As will also be appreciated plasmid pUHC13-3 may be modified for the specific application by replacing genetic elements like poly-adenylation sites or splice sites with those functioning in the cell line in question. Specific details may be found in the references throughout this application or references cited therein, the full contents of which are incorporated herein by reference. A second criterion for the selection of the optimal minimal promoter is the degree of repression in the presence of tetracycline (see below). Typically the deletion mutant with the highest activation factor as described below is chosen.

Promoter deletion mutants may be prepared as generally described by Rosen, C. et al (1985) Cell Vol. 41, 813–823 or Nelson C. et al. (1986) Nature Vol. 322, 557–562. Other methods, including methods useful in the preparation of stable tetR-VP 16 cell lines, are essentially as described in "Current Protocols in Molecular Biology" Ausubel, F. M. et al (eds.) 1989 Vol. 1 and 2 and all supplements to date Greene Publishing Associates and Wiley-Interscience, John Wiley & Sons, New York, the full contents of which are incorporated herein by reference, or as described in the other references cited throughout this application.

The presence of tet operator element(s) renders such recombinant promoter moieties responsive to the tTA of the invention. In HeLa cells constitutively expressing the TetR-VP 16 tTA, high levels of luciferase expression have been achieved under the control of such a modified CMV promoter sequence. The incorporation of the tetR domain within the tTA renders this expression system sensitive to the presence of tetracycline. The binding of tetracycline to the tetR domain of the tTA prevents the tTA from exerting its transactivating effects. Depending on the concentration of tetracycline in the culture medium (0–1 $\mu$g/ml), the luciferase activity can be regulated up to five orders of magnitude in the previously mentioned example. This system provides both a reversible on/off switch and a differential control—as desired—for regulating gene expression in eucaryotic hosts. It should be appreciated that tetracycline analogs which are capable of specific functional interaction with tetR may be used in place of tetracycline, A eucaryotic production cell line of this invention is prepared according to the design described above. Assembly of the components and incorporation thereof into a eucaryotic host cell are conducted by otherwise conventional methods such as are described generally by Kriegler, M. (editor), 1990, Gene Transfer and Expression, A Laboratory Manual (Stockton Press). Care should to be taken to select for integration of the gene of interest into a chromosomal site that exhibits sufficiently low basal expression when, or to the extent, desired (see e.g. Table 1). The recombinant host cell obtained is grown in the presence of tetracycline or tetracycline analogues until an optimal density that has been determined empirically to allow for subsequent induction of gene expression. After the desired cell density has been reached gene expression is induced by dilution and/or removal of the tetracycline or analog thereof. The culture is then continuously grown until a optimal expression level has been reached. The recombinant protein is then harvested according to standard procedures.

The use of eucaryotic cells as host cells for expression of recombinant proteins is generally reviewed in M. Kriegler 1990 "Gene Transfer and Expression, A Laboratory Manual". Stockton Press., incorporated herein as reference, While CHO$^{dhfr-}$cells (Urlaub, G. and Chasin (1980) Proc. Natl. Acad. Sci. USA 77: 4216–4220), 293 cells (Graham, F. L. et al. (1977) J. Gen. Virol. 36: pp. 59) or myeloma cells like SP2 or NSO (Galfre, G. and Milstein, C. (1981) Meth Enzymol. 73 (B): 3–46) are commonly used it should be clear to those of ordinary skill in the art, that any eucaryotic cell line can be used in the practice of the subject invention, so long as the cell line is not incompatible with the protein to be expressed, the selection system chosen or the fermentation system employed. This invention is broadly applicable and encompasses non-mammalian eucaryotic cells as well, including insect (e.g. Sp. frugiperda), yeast (e.g. S. cerevisiae, S. pombe, H. polymorpha) and fungal cells, containing and capable of expressing the two components of the foregoing genetic switch.

The eucaryotic host cells used for regulated expression in this invention may thus be yeast cells including, but not limited to Saccharomyces cerevisiae, Pichia pastoris, Kluyveromyces lactis and Hansenula polymorpha, as generally reviewed by Fleer, R. (1992), Current Opinion in Biotechnology Vol. 3, No. 5: p. 486–496, the full contents thereof and of which the references cited therein are incorporated herein by reference.

In other embodiments the eucaryotic cells used for regulated expression are insect cells carrying in their chromosomes the heterologous DNA moiety encoding a transactivator fusion protein (tTA) comprising a tetracycline repressor and a protein capable of activating transcription in the host cell. A second recombinant DNA moiety encoding the gene of interest operably linked to a promoter responsive to the transcriptional activator is carried on the baculovirus genome. Suitable general methods which may be used in the practice of these aspects of the invention are reviewed by O'Reilly et al. (1992) "Baculovirus expression vectors, A Laboratory Manual" Stockton Press, the full contents of which are incorporated herein by reference.

While the gene of interest may be a heterologous gene, i.e. not otherwise present in the parental host cell genome, an important aspect of this invention relates to the regulation of an endogenous gene of interest. In such cases the host cell is genetically engineered to insert into the host cell genome the tTA-responsive promoter such that the desired endogenous gene is under the transcriptional control of the tTA-responsive promoter. This may be accomplished for example by linking a copy of the endogenous gene to the tTA-responsive promoter and transfecting or transforming the host cell with the recombinant construct. In one approach, the construct is introduced by homologous recombination into the loci of the endogenous gene. Briefly, the tTA responsive promoter is flanked on the 5' side by sufficient DNA sequences from the upstream region but excluding the actual promoter region of the endogenous gene and on the 3' end by sequences representing the coding region of the endogenous gene. The extent of DNA sequence homology necessary for homologous recombination is discussed below.

In other approaches that construct is inserted at another genetic locus, either predetermined or at random. In any case, the eucaryotic cell is also transformed or transfected with the DNA construct permitting expression of the tTA. Alternatively, the DNA construct encoding the tTA may itself be inserted at the locus of the endogenous gene of interest and the DNA moiety encoding the gene of interest operably linked to a tTA-responsive promoter may be introduced elsewhere in the genome. In that embodiment, the tTA vector contains the tTA-encoding DNA moiety flanked by DNA sequence of the locus of the endogenous gene permitting homologous recombination of the construct into that locus.

The use of flanking DNA sequence to permit homologous recombination into a desired genetic locus is known in the art. At present it is preferred that up to several kilobases or more of flanking DNA corresponding to the chromosomal insertion site be present in the vector on both sides of the tTA-encoding sequence (or any other sequence of this invention to be inserted into a chromosomal location by homologous recombination) to assure precise replacement of chromosomal sequences with the exogenous DNA. See e.g. Deng et al, 1993, Mol. Cell. Biol 13(4):2134–40; Deng et al, 1992, Mol Cell Biol 12(8):3365–71; and Thomas et al, 1992, Mol Cell Biol 12(7):2919–23. It should also be noted that the eucaryotic cell of this invention may contain multiple copies of the gene of interest, e.g. by conventional genetic amplification, each operably linked to the tTA-responsive promoter.

It should be clear from the preceding that to achieve the goals of introducing the DNA moiety encoding the tTA into the host cell genome and of introducing the tTA-responsive promoter construct in operable linkage to the desired gene, vectors based on the following principles are required. First, to introduce the tTA-encoding construct into the genome of the host cell such that its expression will follow the regulated pattern of expression observed in the unmodified host cell for the gene of interest, it is necessary to introduce the tTA-encoding construct such that its expression is made subject to the transcription control elements associated with the gene of interest. One way to do so is to introduce the tTA-encoding construct by homologous recombination into the genetic locus of the gene of interest. A vector for such introduction comprises the DNA sequence encoding the tTA flanked by sufficient DNA sequence from the locus of the gene of interest in the host genome to permit the desired homologous recombination event in which the tTA and flanking DNA is effectively swapped for the flanking DNA copy and the DNA included there between within the host cell genome. As will be appreciated an expression construct containing a tTA responsive promoter operably linked to the DNA sequence of the endogenous gene can be integrated at random sites without the help of flanking homologous sequences as described in references throughout this application. Alternatively, to insert a DNA sequence comprising a tTA-responsive promoter or tetO control element(s) upstream of a desired gene, a construct is assembled in which the DNA comprising the tTA-responsive promoter is ligated upstream of a copy of the desired gene between DNA sequences flanking the desired insertion site in the host genome. In either event the tTA construct can be introduced as mentioned previously.

Using the foregoing genetic constructs and engineered eucaryotic cells, this invention further provides a method for regulating the expression of a gene of interest. In one aspect of this method eucaryotic host cells engineered as described above are cultured under otherwise conventional conditions suitable for cell growth and proliferation, but in a culture medium containing a substance capable of binding to the tetracycline repressor moiety and of blocking or inhibiting transcriptional activation. Tetracycline is the archetypical such substance. However, tetracycline analogs which bind to tetR to form a complex which is not transcriptionally activating may of course be substituted for tetracycline. The precise concentration of tetracycline or other such substance will depend on the substance's affinity for the tetR domain and/or the substance's specific inhibitory activity, as well as the cell density and copy number of the tTA and the desired level of inhibition of gene expression. Nonetheless, appropriate levels of inhibitory substance for the desired level of inhibition are readily determinable empirically without undue effort.

Cell culture in accordance with the preceding method negatively regulates, i.e. inhibits expression of the gene of interest, completely or partially. Culturing of the cells thereafter in media with a lower concentration (relative to the initial concentration) of the tetR binding substance permits gene expression to begin or to ensue at a now higher level. If an initial concentration of binding substance (e.g. tetracycline) is selected which is sufficient to inhibit gene transcription substantially completely (e.g. transcription is not observed under conventional Northern blotting conditions), and in the following phase of cell culture the binding substance is substantially removed from the media, gene expression can be said to be regulated in an on/off manner. In some applications, intermediate levels of expression may be desired. To that end, concentrations of binding substance may be selected based on empirical data to provide predetermined intermediate level(s) of gene transcription. It should be understood that removal of the binding substance from the media may be effected by gradual, step-wise, continual or total replacement of culture media containing the binding substance with culture media lacking the binding substance or simply containing reduced levels of the binding substance.

Where the eucaryotic cells engineered in accordance with this invention are incorporated into the host organism, e.g. to create a transgenic organism, this invention provides a genetically engineered non-human animal capable of regulatably expressing a gene of interest. Such animal, in the broad sense, comprises cells containing and capable of expressing a heterologous DNA moiety encoding a tTA as previously defined and a DNA moiety comprising an gene of interest under the transcriptional control of a heterologous promoter responsive to the transcriptional activator.

Thus, this invention further relates to non-human animals derived by homologous recombination of one or more polynucleotide molecules of the invention into a specific target site within their genome, the offspring of such animals, as well as to a method to prevent or promote the expression of a targeted gene in a conditional manner.

This embodiment of the invention is able to solve a longstanding problem in the field generally described as gene targeting or gene knock out (Capecchi. M. R. (1989) Science Vol 244, p. 1288–1292, Bradley, A. (1991) Current opinion in Biotechnology Vol. 2, p. 823–829) pertaining to genes whose mutations results in death of the homozygous embryos, e.g., as described for the knock out of the RB gene (Jacks, T. et al. (1992) Nature 359:295–300). If the genetic switch subject of the current invention is applied as described below, expression of an endogenous gene of interest operably linked to a tet operator sequence(s) can be stimulated by a tetracycline-controllable transactivator (tTA) of the invention and the animal develops like a nonmutated wildtype animal. Then, at a particular stage of development, expression of the endogenous gene of interest can be switched off by raising the level of tetracycline or a tetracycline analogue in the circulation and the tissues of the animal by feeding or injecting the tetracycline or tetracycline analog to the animal, thereby inhibiting the activity of the tTA and transcription of the gene of interst. This method is generally referred to herein as a "conditional knockout".

As will be clear from the following, two principally different approaches have been devised to apply the genetic switch of this invention to the genome of the non-human animal in a way, that will allow for a temporally and spatially correct expression of the endogenous gene. In one approach, the two elements of the genetic switch are in separate locations in the chromosome and require two integration steps, another one achieves the desired result in one step.

In the first step of one embodiment of the invention non-human animals are derived by homologous recombination of the DNA sequences of the tTA into a specific DNA site containing the nucleotide sequences of an endogenous gene of interest in such a way that part or all of the coding sequence of the endogenous gene is replaced with the tTA gene. This can be accomplished (see FIG. 11) in the following steps:

(1) assembling a chimeric gene in which the sequence of the first (i.e. tTA) polynucleotide molecule of the invention is flanked by DNA sequences from the gene of interest such that upon incorporation of the chimeric gene into the host genome, the DNA sequences that normally control the expression of the target gene are fused to and control expression of the DNA sequences for the tTA.

(2) introducing this chimeric gene into an embryonic stem cell line from a species of interest and screening resultant candidate embryonic cell clones to identify and recover those cells in which homologous recombination has taken place at the locus of interest.

(3) introducing those recombinant cells so identified and recovered into a blastocyst from the species of interest to yield a chimeric embryo.

(4) implanting the chimeric embryo into the uteri of pseudopregnant recipient mothers to facilitate development and birth of a homologous recombinant offspring.

This process results in offspring whose genome contains the DNA sequence encoding the tTA inserted in place of the gene of interest such that the tTA DNA is expressed in a pattern similar or identical to that of the gene of interest. These processes and their results are collectively and commonly referred to as "gene knock-out". These techniques are well established and described in: Wood et al. Proc. Natl. Acad. Sci. 90:4582–4585, Simon et al. Nature Genetics 1:92–97 & Soriano et al. Cell 64:693–702 and references therein, the full content of which are in their entirety incorporated herein by reference.

The second step in this embodiment of the invention relates to the preparation of a second transgenic animal which contains in it's genome the gene of interest under transcriptional control of the tetracycline (Tc) responsive promoter element. This can be accomplished using the following method:

(1) A chimeric DNA sequence is prepared where a Tc responsive promoter element, (comprising at least one tet operator and a minimal promoter) is cloned 5' of the DNA sequences encoding the endogenous gene of interest. One way to accomplish this is to replace the luciferase coding sequence and all polyadenylation elements in the plasmids pUHC13-3 or pUHC13-4 with the DNA sequence containing the complete genomic coding sequence of the endogenous gene and sufficient 3' non coding sequence to allow for proper polyadenylation. As will be appreciated the DNA sequence encoding the endogenous gene can also be cDNA (cloned as an example in such a way that it replaces exactly the luciferase gene in pUHC13-3 or pUHC13-4) or any combination of genomic DNA and cDNA designed to provide the complete coding sequence, any regulatory elements that may reside in intron sequences or is not contained in it's entirety in the cDNA and a polyadenylation signal or other elements typically associated with the endogenous gene. General cloning and DNA manipulation methods are described in references cited throughout this application.

(2) The chimeric DNA sequence (called also "the chimeric transgene") is injected into a fertilized egg which is implanted into a pseudopregnant recipient mother and allowed to develop into an adult animal. In particular, a few hundred DNA molecules are injected into the pro-nucleus of a fertilized one cell egg. The microinjected eggs are then transferred into the oviducts of pseudopregnant foster mothers and allowed to develop. It has been reported by Brinster et al. (1986) Proc. Natl. Acad. Sci. USA Vol. 83:9065–9069, the full contents of which are incorporated by reference herein, that about 25% of mice which develop will inherit one or more copies of the microinjected DNA. A protocol for constructing such transgenic animals (Brinster et al. Proc. Natl. Acad. Sci. 83:4432–4445, Crenshaw et al. Genes 3: Dev 9:959–972 and references cited therein) is a well established technique as is the breeding of recombinant and hybrid animals.

Breeding of animals resulting from the first and the second step of this embodiment of the invention produces offspring containing both the replaced gene of interest and the chimeric transgene. In a preferred embodiment, animals heterozygous for the knockout of the endogenous gene resulting from the first step of this embodiment of the invention (and instead expressing a tTA gene) are used for breeding with animals that are homozygous for the chimeric transgene resulting from the second step of this embodiment of the invention. The resulting offspring are analyzed by standard techniques, including tail-blot analysis described in references throughout this application, and animals homozygous for both traits are selected. Typically about 50% of the offspring should carry both traits. In these animals, replacement of the coding sequences of the gene of interest with those of the DNA sequences of the tTA is such that the tTA is expressed in a temporal and spatial pattern similar or identical to that of the gene of interest and regulates in trans expression of the gene of interest now under transcriptional control of (i.e., operably linked to) the DNA sequences of the Tet operator and minimal promoter inserted at it's 5' end.

As will be appreciated, the particular breeding strategy depends on the nature of the gene of interest. If the "knock out" of the endogenous gene with the tTA coding sequence is not lethal and the overall plan is to create animals where the functions of the gene of interest in the adult can be studied in the "on" or "off" state, the animals from the first step of this embodiment of the invention can be bred to homozygosity and then bred with the homozygous mice from the second step.

In this combination, the gene of interest is regulated by the addition or subtraction of tetracycline or its analogs from the food or water supply of the animal as discussed below.

In another embodiment of the invention, embryonic stem (ES) cell technology is used to prevent or promote expression of a gene interest in a conditional manner (FIG. 12). In the first step of this embodiment of the invention, a chimeric DNA sequence (commonly referred to as a chimeric transgene) consisting of the DNA sequences of the tet operator(s) and a suitable minimal promoter inserted 5' of the DNA sequences encoding a gene of interest is introduced by stable, non-homologous recombination into random sites in the ES cell genome. Co-introduced with this chimeric construct is a selectable marker that enables the selection of cell clones that have integrated DNA constructs from cells that have not. As will be appreciated, the feeder cells supporting the growth of the ES cells have to express the same resistance gene used for the selection step. As an example, if the selection marker chosen is the hygromycin resistance gene, the primary feeder layer cells used for the ES cell culture can be derived from an animal transgenic for the hygromycin resistance gene prepared according to standard procedures for the preparation of transgenic animals, as cited throughout this application. ES cell clones are selected for low basal expression of the chimeric transgene using customary detection methods, such as evaluating the mRNA levels of the transgene as described in "Current Protocols in Molecular Biology" Ausubel, F. M. et al (eds.) 1989 Vol. 1 and 2 and all supplements to date, Greene Publishing Associates and Wiley-Interscience, John Wiley & Sons, New York, the full contents of which are incorporated herein by reference, or as described in the other references cited throughout this application. Other methods to detect expression of the transgene may include activity assays or assays designed to detect protein expression. Low basal expression of the transgene is determined relative to untransfected cells. Alternatively, low basal expression of the tet operator-linked transgene can be evaluated in different tissues of animals derived from the embryonic stem cells. For example, ES cells can be transfected with the transgene in culture, and the clones expanded, selected and injected into blastocysts to create transgenic animals. After standard identification and breeding to create animals carrying the transgene in all tissues, the baseline expression of the tet-operator linked transgene can be examined in various tissues of interest (e.g., by conventional techniques for analyzing mRNA expression, such as Northern blotting, S1 nuclease mapping or reverse transcriptase-polymerase chain reaction). Additionally, basal expression of the transgene can be examined in primary cultures of cells derived from various tissues of the animal (e.g, skin cells in culture).

A second criterion for the selection of the stable clone is the ability of the tet operator-linked transgene to respond to transient or stable expression of tTA upon transfection of a tTA expression plasmid like pUHD15-1 or pUHD151-1. As will be appreciated, these plasmids are cited as examples only and others can be devised that expressed sufficient quantities of tTA in ES cells. The ability of tTA to induce expression of a tet-operator linked transgene stably transfected into an ES cell clone can be examined by supertransfecting the ES cell clone with a tTA expression plasmid and assaying expression of the transgene. Alternatively, inducibility of a tet-operator linked transgene can be examined in cells derived from various tissues of a transgenic animal carrying the transgene by preparing primary cultures of cells from the animal (e.g., skin cell cultures), transfecting the cells with a tTA expression plasmid and assaying expression of the transgene in the cells by standard techniques.

A clone fulfilling the criteria discussed above is selected and expanded in number. This clone is then used as a recipient of a gene knock-out procedure consisting of the following steps:

(1) flanking the sequences of a polynucleotide molecule encoding a tTA of the invention by DNA sequences from a second gene of interest such that the DNA sequences that normally control the expression of the second target gene of interest are fused to and control expression of the DNA sequences of encoding the tTA;

(2) introducing this chimeric gene into an embryonic cell line from a species of interest and modified as described above and screening candidate embryonic cell clones for those in which homologous recombination has taken place at the locus of interest;

(3) introducing those recombinant cells into blastocysts from the species of interest; and (4) implanting the chimeric embryo into the uteri of pseudopregnant recipient mothers to facilitate development and birth of a homologous recombinant animal.

This process results in offspring containing a replacement of the amino acid coding sequences of the second gene of interest with those of the DNA sequences of the tTA such that the tTA encoding sequence is expressed in a temporal and spatial pattern similar to that of the endogenous second gene of interest. In this case, it is necessary to self cross the recombinant animals (or breed to homozygosity) so that both copies of the target sequence into which the tTA coding sequences have been integrated are interrupted. This procedure also leads to homozygosity of the tet-operator linked transgene (i.e., animals homozygous for both components of the genetic switch described herein can be produced). These techniques are well established and described in: Wood et al., Proc. Natl. Acad. Sci. 90:45824585, Simon et al. Nature Genetics 1:92–97; and Soriano et al. Cell 64:693–702 and references therein.

In yet another embodiment of the invention, embryonic stem (ES) cell technology can again be used to prevent or promote expression of a gene interest in a conditional manner using a single homologous recombination step that will result in the integrated copy shown in FIG. 13. In this method, a DNA construct containing a fusion of the sequences that normally flank the endogenous gene of interest at the 5' end (and contain sequences commonly referred to as promoter sequences) are fused to the DNA sequences encoding the tTA molecule. At the 3' end of the tTA coding sequence, DNA sequences encoding resistance to a selectable marker are typically included. For example, a neomycin resistance gene, which may be fused to either a constitutive regulatory element (e.g., a pPGK promoter as depicted in FIG. 13A) or to a tet operator sequence(s) (as depicted in FIG. 13B) can be inserted at the 3' end of the tTA encoding sequence. When the selectable marker is operably linked to a tet operator sequence(s), its expression is regulated by the tTA (e.g., a resistance phenotype will be expressed in the absence but not the presence of Tc). Finally, 3' of the selectable marker sequences in this DNA construct are inserted the DNA sequences encoding the endogenous gene of interest, which are also fused to at least one tet operator sequence and a minimal promoter.

Because in this configuration of the DNA molecule, conventionally called the targeting vector, the coding sequences of the tTA, the selectable marker and the endogenous gene of interest are all flanked by the sequences normally flanking the endogenous gene of interest, this DNA construct has the potential for homologous recombination with the locus of the endogenous gene of interest upon its introduction into cells such as, but not limited to ES cells. Homologous recombination of this type alters the natural locus such that the gene of interest falls under the control of the tTA and consequently under regulation by the presence or absence of tetracycline or derivative thereof. The expression of the tTA protein, on the other hand, follows the normal pattern of expression of the gene of interest. Recombinant ES cells of this type are then used to generate intact organisms as has been described (Wood et al. Proc. Natl. Acad. Sci. 90:4582–4585, Simon et al. Nature Genetics 1:92–97; and Soriano et al. Cell 64:693–702) which can in turn be breed to homozygosity.

As will be appreciated, the close proximity of the promoter elements in this particular configuration of the DNA construct used for homologous recombination may require special consideration to insulate the downstream tet operator/minimal promoter operably linked to the endogenous gene from long range effects of the endogenous promoter operably linked to the tTA coding sequence to achieve the required low basal level expression of the endogenous gene. Some possible solutions are strong transcriptional terminators known to those of ordinary skill in the art, DNA elements that increase the distance between the elements or others that limit the effect of enhancer sequences (e.g., transcriptional insulators, including matrix attachment regions), all of which are to be cloned alone or in combination in between the selectable marker expression unit (e.g., neomycin resistance gene with linked promoter) and the tTA-responsive transcriptional promoter sequence (see FIG. 13). Examples of suitable transcriptional terminators, transcriptional insulators, matrix attachment regions and/or other sequences which can be included in the "single hit" targeting vector to inhibit basal transcription of the tet operator-linked endogenous gene are described in Sato, K. et al. (1986) Mol. Cell. Biol. 6:1032–1043; Michel, D. et al. (1993) Cell. Mol. Biol. Res. 39:131–140; Chung, J. H. et al. (1993) Cell 74:505–514; Nezanov, N. et al. (1993) Mol. Cell. Biol. 13:2214–2223; and Thorey, I. S. et al. (1993) Mol. Cell. Biol. 13:6742–6751.

The different animals resulting from any of the above mentioned embodiments can be studied either in the absence (endogenous gene switched "on") or presence (endogenous gene switched "off") of tetracycline or tetracycline analogues as described for other transgenic animals below. Such animals can be used to identify, compare and characterize the activity of substances which interact with, upon or through the action of the gene product of interest.

The present invention relates to a control system that in eucaryotic cells allows regulation of expression of an individual gene over up to five orders of magnitude. This system is based on regulatory elements of a tetracycline resistance operon, e.g. Tn10 of *E. coli* (Hillen & Wissmann, "Topics in Molecular and Structural Biology," in Protein-Nucleic Acid Interaction, Saeger & Heinemann, eds., Macmillan, London, 1989, Vol. 10, pp. 143–162), in which transcription of resistance-mediating genes is negatively regulated by the tetracycline repressor (tetR). In the presence of tetracycline or a tetracycline analogue, tetR does not bind to its operators located within the promoter region of the operon and allows transcription. By combining tetR with a protein capable of activating transcription in eucaryotes, e.g. the C-terminal domain of VP16 from HSV (known to be essential for the transcription of the immediate early viral genes (Triezenberg et al., (1988) Genes Dev. 2:718–729), a hybrid transactivator is generated that stimulates minimal promoters fused to tetracycline operator (tetO) sequences. These promoters are virtually silent in the presence of low concentrations of tetracycline, which prevents the tetracycline-controlled transactivator (tTA) from binding to tetO sequences.

The specificity of the tetR for its operator sequence (Hillen & Wissmann, "Topics in Molecular and Structural Biology," in Protein-Nucleic Acid Interaction, Saeger & Heinemann, eds., Macmillan, London, 1989, Vol. 10, pp. 143–162) as well as the high affinity of tetracycline for tetR (Takahashi et al., J. Mol. Biol. 187:341–348 (1986)) and the well-studied chemical and physiological properties of tetracyclines constitute a basis for an inducible expression system in eucaryotic cells far superior to the lacR/O/IPTG system. This has already been demonstrated in plant cells, in which direct repressor action at promoter sites is efficiently reversed by the antibiotic (Gatz & Quail, (1988) Proc. Natl. Acad. Sci. USA 85:1394–1397, Gatz et al., (1991) Mol. Gen. Genet. 227:229–237). However, these previous systems used a tet repressor alone to inhibit gene expression, which may be inefficient or require high concentrations of the repressor intracellularly to function effectively. In contrast, the tTA of the present invention functions as a transcriptional activator to stimulate expression of a tet operator-linked gene.

In particular, the invention relates to a polynucleotide molecule coding for a transactivator fusion protein comprising the tet repressor (tetR) and a protein capable of directly or indirectly activating transcription in eucaryotes. The portion of the polynucleotide molecule coding for tetR may be obtained according to Altschmied et al., EMBO J. 7:4011–4017 (1988), the contents of which are fully incorporated by reference herein. Other tetR sequences are available from Genbank and/or are disclosed in Waters, S. H. et al. (1983) Nucl. Acids Res. 11:6089–6105; Unger, B. et al. (1984) Gene 31:103–108, Unger, B. et al. (1984) Nucl. Acids Res. 12:7693–7703; Iovar, K. et al. (1988) Mol. Gen. Genet. 215:76–80; Hillen, W. and Schollmeier, K. (1983) Nucl. Acids Res. 11:525–539 and Postle, K. et al. (1984) Nucl. Acids Res. 12:4849–4863, the contents of each of which are fully incorporated herein by reference.

The portion of the polynucleotide molecule coding for the negatively charged C-terminal domain of HSV-16, a protein known to be essential for transactivation in eucaryotes, may be obtained according to Triezenberg et al., Genes Dev. 2:718–729 (1988), the contents of which are fully incorporated by reference herein. Preferably, the activating domain comprises the C-terminal 130 amino acids of the virion protein 16. Alternatively, other polypeptides with transcriptional activation ability in eucaryotic cells can be used in the tTA of the invention. Transcriptional activation domains found within various proteins have been grouped into categories based upon similar structural features. Types of transcriptional activation domains include acidic transcription activation domains, proline-rich transcription activation domains, serine/threonine-rich transcription activation domains and glutamine-rich transcription activation domains. Examples of acidic transcriptional activation domains include the VP16 regions already described and amino acid residues 753–881 of GAL4. Examples of proline-rich activation domains include amino acid residues 399–499 of CTF/NF1 and amino acid residues 31–76 of AP2. Examples of serine/threonine-rich transcription activation domains include amino acid residues 1–427 of ITF1 and amino acid residues 2–451 of ITF2. Examples of glutamine-rich activation domains include amino acid residues 175–269 of Oct1 and amino acid residues 132–243 of Sp1. The amino acid sequences of each of the above described regions, and of other useful transcriptional activation domains, are disclosed in Seipel, K. et al. (EMBO J. (1992) 13:4961–4968).

The polynucleotide molecule coding for tetR may be linked to a polynucleotide molecule coding for the activating domain (e.g., of HSV VP16) and recombined with vector DNA in accordance with conventional recombinant DNA techniques, including blunt-ended or stagger-ended termini for ligation, restriction enzyme digestion to provide appropriate termini, filling in of cohesive ends as appropriate, alkaline phosphatase treatment to avoid undesirable joining, and ligation with appropriate ligases. Alternatively, nucleic acid fragments encoding the repressor and the activating domain can be obtained by polymerase chain reaction amplification of appropriate nucleotide sequences using template DNA encoding either the repressor or the activating domain (e.g., encoding VP16). The amplified DNA fragments can then be ligated such that the protein coding sequences remain in-frame and the chimeric gene so produced can be cloned into a suitable expression vector.

Preferably, the polynucleotide molecule coding for the transactivator fusion protein further comprises an operably linked promoter. The promoter may be an inducible promoter or a constitutive promoter. Examples of such promoters include the human *cytomegalovirus* promoter IE as taught by Boshart et al., Cell 41:521–530 (1985), ubiquitously expressing promoter such as HSV-Th (McKnight et al., Cell 37:253–262 (1984)) and β-actin promoters (e.g. the human β-actin promoter as described by Ng et al., Mol. Cell. Biol. 5:2720–2732 (1985)), as well as promoters in combination with control regions allowing integration site independent expression of the transgene (Grosveld et al., Cell 51:975–985 (1987)), as well as tissue specific promoters such as albumin (liver specific, Pinkert et al., Genes Dev. 1:268–277 (1987)), lymphoid specific promoters (Calame and Eaton, Adv. Immunol. 43:235–275 (1988)), in particular promoters of T-cell receptors (Winoto and Baltimore, EMBO J. 8:729–733 (1989)) and immunoglobulins; Banerji et al., Cell 33:729–740 (1983); Queen and Baltimore, ibid. 741–748), neuron specific promoters (e.g. the neurofilament promoter; Byrne and Ruddle, Proc. Natl. Acad. Sci. USA 86:5473–5477 (1989)), pancreas specific promoters (Edlund et al., Science 230:912–916 (1985)) or mammary gland specific promoters (milk whey promoter, U.S. Pat. No. 4,873,316 and European Application Publication No. 264, 166) as well as developmentally regulated promoters such as the murine hox promoters (Kessel and Cruss, Science 249:374–379 (1990)) or the α-fetoprotein promoter (Campes and Tilghman, Genes Dev. 3:537–546 (1989)), the contents of each of which are fully incorporated by reference herein. Preferably, the promoter is constitutive in the respective cell types. In one embodiment of the invention, the polynucleotide molecule encoding the transactivator is integrated at a predetermined location within a second target DNA molecule (e.g., a gene of interest within a chromosome) such that the tTA-coding sequences are placed under the control of endogenous regulatory elements (e.g., a 5' regulatory region of a target gene of interest into which the tTA-coding sequence is integrated). Depending upon which gene the tTA-coding sequences are integrated into, the endogenous regulatory elements may provide constitutive expression of the tTA in many cell types or may limit expression of the tTA to a particular cell or tissue type.

The invention also relates to another polynucleotide molecule coding for a protein, wherein said polynucleotide is operably linked to a tTA-responsive promoter. Typically, this tTA-responsive promoter comprises a minimal promoter operatively linked to at least one tet operator (tetO) sequence. The tetO sequence may be obtained, for example, according to Hillen & Wissmann, "Topics in Molecular and Structural Biology," in Protein-Nucleic Acid Interaction, Saeger & Heinemann, eds., Macmillan, London, 1989, Vol. 10, pp. 143–162, the contents of which are fully incorporated by reference herein. Other tetO sequences which may be used in the practice of the invention may be obtained from Genbank and/or are disclosed in Waters, S. H. et al. (1983) Nucl. Acids Res. 11:6089–6105; Hillen, W. and Schollmeier, K. (1983) Nucl. Acids Res. 11:525–539; St über, D. and Bujard, H. (1981) Proc. Natl. Acad. Sci. USA 78:167–171; Unger, B. et al. (1984) Nucl Acids Res. 12:7693–7703; and Tovar, K. et al. (1988) Mol. Gen. Genet. 215:76_14 80, which are fully incorporated by reference herein in their entirety. One, two, three, four, five, six, seven, eight, nine or ten or more copies of the tet operator sequence may be employed, with a greater number of such sequences allowing an enhanced range of regulation. As shown in the Examples, multiple copies of the tet operator sequence provides a synergistic effect on the ability to control expression of the heterologous protein.

The polynucleotide sequence specifying the cytomegalovirus promoter may be obtained according to Boshart et al., Cell 41:521–530 (1985), the contents of which are fully incorporated by reference herein. Preferably, positions +75 to −53 to +75 to −31 of the promoter-enhancer are employed as a minimal promoter. The promoter may be followed by a polylinker and then by the gene coding for the protein of interest. While the luciferase gene or other reporter gene, e.g. the gene coding for chloramphenicol acetyltransferase or β-galactosidase, may be used to demonstrate the operability of the regulatory system, the invention is not intended to be so limited. Examples of such genes include, but are not limited to the estrogen receptor, the GABA receptor, the progesterone receptor and the X-protein of HBV.

The present invention also relates to eucaryotic cells transfected with the polynucleotide molecules of the present invention. In particular, the invention relates to eucaryotic cells transfected with (a) a first polynucleotide molecule coding for a transactivator fusion protein comprising a prokaryotic tet repressor and a protein capable of activation transcription in eucaryotes; and (b) a second polynucleotide molecule coding for a protein, wherein said second polynucleotide molecule is operably linked to a minimal promoter and at least one tet operator sequence.

The two polynucleotide molecules may reside on the same or separate vectors. In a preferred embodiment, the first polynucleotide is integrated into the chromosome of a eucaryotic cell or transgenic animal and the second polynucleotide is introduced as part of a vector. Integration may be achieved where there is crossover at regions of homology shared between the incoming polynucleotide molecule and the particular genome.

The expression of the heterologous protein from such transfected eucaryotic cells may be tightly regulated. Unexpectedly, it has been determined that the expression system of the present invention may be used to regulate expression by about 5 orders of magnitude. In addition, it has been discovered that the expression system of the present invention allows one to rapidly turn "on" and "off" the expression of the heterologous gene in a reversible way. Moreover, it has been discovered that the expression system of the invention allows one to achieve a desired level of expression according to how much tetracycline or tetracycline analogue is employed (see FIG. 3). Thus, the expression system of the present invention is a great advance in the art.

The invention also relates to transgenic animals comprising at least a first polynucleotide molecule of the present invention encoding a tTA. Such transgenic animals may be obtained, for example, by injecting the polynucleotide into a fertilized egg which is allowed to develop into an adult animal. In particular, a few hundred DNA molecules are injected into the pro-nucleus of a fertilized one cell egg. The microinjected eggs are then transferred into the oviducts of pseudopregnant foster mothers and allowed to develop. It has been reported by Brinster et al., Proc. Natl. Acad. Sci. USA 82:4438–4442 (1985), the contents of which are fully incorporated by reference herein, that about 25% of mice which develop will inherit one or more copies of the microinjected DNA. It is also possible to prepare a polynucleotide molecule comprising a milk protein promotor and microinject the DNA into the fertilized egg to give, upon development, a transgenic mammal which is capable of producing the heterologous protein in its milk, when in the absence of tetracycline or a tetracycline analog. See International Application Publication No. WO 88/00239 and European Application Publication No. 0264,166, the contents of which are fully incorporated by reference herein.

The invention also relates to non-human animals and their offspring derived by homologous recombination of the DNA sequences of the first polynucleotide molecules of the invention into a specific DNA site containing the nucleotide sequences of a gene referred to as the target gene. This would be accomplished in the following steps: 1) flanking the sequences of the first polynucleotide molecule of the invention encoding a tTA by DNA sequences from the target site such that the DNA sequences that normally control the expression of the target gene are fused to and control the expression of the DNA sequences of the first polynucleotide molecules of the invention, 2) introducing this chimeric gene into an embryonic cell line from the species of interest and screening candidate embryonic cell clones for those in which homologous recombination has taken place at the target gene locus, 3) introducing those recombinant cells into a blastocysts from the species of interest, 4) implanting the chimeric embryo into the uteri of pseudopregnant recipient mothers to facilitate development and birth. This process will result in offspring containing a replacement of the amino acid coding sequences of the target gene with those of the DNA sequences of the first polynucleotide molecule of the invention such that this corresponding amino acid sequence will be expressed in a pattern similar to that of the target gene. These processes and their results are collectively and commonly referred to as "gene knock-out". These techniques are well established and described in: Wood et al. Proc. Natl. Acad. Sci. 90:4582–4585, Simon et al. Nature Genetics 1:92–97 & Soriano et al. Cell 64:693–702 and references therein.

The invention also relates to a method to prevent or promote the expression of the target gene in a conditional manner. This may be accomplished by breeding an animal containing the target gene knock-out (as outlined in the preceding paragraph) with a transgenic animal derived by the following method. The transgenic animal would be constructed by inserting, by micro-injection, a chimeric DNA sequence (commonly referred to as a chimeric transgene) consisting of the DNA sequences of the second polynucleotide molecule of the invention inserted 5' of the DNA sequences encoding the amino acid sequence of the target gene into the genome of a fertilized egg which is allowed to develop into an adult animal. The protocol for the construction of such transgenic animals is a well established technique (Brinster et al. Proc. Natl. Acad. Sci. 83:4432–4445, Crenshaw et al. Genes & Dev 3:959–972 and references therein) as is the breeding of animals. From the breeding will result offspring containing both the gene knock-out and the chimeric transgene. That is, replacement of the amino acid coding sequences of the target gene with those of the DNA sequences of the first polynucleotide molecule of the invention such that this corresponding amino acid sequence will be expressed in a pattern similar to that of the target gene and, the DNA sequences of the second polynucleotide molecule of the invention inserted 5' of the DNA sequences encoding the amino acid sequence of the target gene. In this combination the target gene can be regulated by the addition or subtraction of tetracycline or its analogs from the food or water supply of the animal.

Thus, the invention also relates to a method to down regulate the expression of a protein coded for by a polynucleotide, comprising cultivating the transfected eucaryotic cells of the present invention in a medium comprising tetracycline or a tetracycline analogue. As described in the Examples, it is possible to closely control the extent of expression by carefully controlling the concentration of tetracycline or tetracycline analogue in the culture media. As shown in FIG. 3, panel A, as little as 0.0001 $\mu$g/ml of tetracycline will begin to result in a decrease of polypeptide (luciferase) expression. At about 0.1 $\mu$g/ml, the expression is essentially shut off. The concentration of tetracycline or tetracycline analogue which can be used to regulate the expression level may range from about 0.001 to about 1 $\mu$g/ml.

The invention also relates to a method to up regulate the expression of a protein coded for by a polynucleotide, comprising cultivating the eucaryotic cells of the present invention in a medium lacking tetracycline or a tetracycline analogue.

The invention also relates to a method to use regulated gene expression in the production of recombinant proteins as generally reviewed by Yarranton, G. T 1992, the whole article incorporated as reference herein. Expression of recombinant proteins that are cytotoxic or otherwise infer with physiological processes in cells has been hampered by the lack of suitable methods to tightly regulate gene expression. In contrast, a production cell line according to the current invention is grown in the presence of tetracycline or tetracycline analogues until an optimal density (assessed empirically to allow for subsequent induction of gene expression) and expression is induced by dilution of the regulating compound. The culture is continuously grown until an optimal expression level has been reached. The recombinant protein is then harvested according to standard procedures.

As a preferred embodiment, eucaryotic cells are used for expression of recombinant proteins as generally reviewed in "Gene Transfer and Expression" (M. Kriegler 1990) incorporated herein as reference. While $CHO^{dhfr-}$ cells (Urlaub, G. and Chasin, L. 1980), 293 cells (Graham, F. L. et al. 1977) or myeloma cells like SP2 or NSO (Galfre, C. and Milstein, C. 1981) are commonly used it should be clear to the skilled in the art, that any eucaryotic cell line can be used that is suitable for the protein to be expressed, the selection system chosen and the fermentation system employed.

In another preferred embodiment, the cells used for regulated expression are yeast cells including, but not limited to Saccharomyces cerevisiae, Pichia pastoris, Kluyveromyces lactis and Hansenula polymorpha as generally reviewed by Fleer, R. 1992, the whole article incorporated as referenced herein.

In another preferred embodiment, the cells used for regulated expression are insect cells with the gene and promoter region carried on the baculovirus genome as generally reviewed in "Baculovirus expression vectors" (O'Reilly et al. 1992), the whole document incorporated as referenced herein.

As can be appreciated, the tissue specificity of some promoters dictate that the tet operator sequence/promoter sequence fusion has to be designed with the particular application and cell line in mind following the teachings in this application using the promoters customarily used for the cell line in question; examples for those promoters are given in the relevant references mentioned above.

It should be clear from the foregoing that it is critical in the current invention that the production cell line is selected for a very low basal expression of the gene under control of the Tet operator/CMV promoter sequence. There are numerous methods currently available employing enzymatically assisted or unassisted homologous recombination to target repeatedly a chromosomal location found empirically to be suited for the integration of the gene encoding the recombinant protein. In addition to the homologous recombination approaches already described herein, enzyme-assisted site-specific integration systems are known in the art and can be applied to the components of the regulatory system of the invention to integrate a DNA molecule at a predetermined location in a second target DNA molecule. Examples of such enzyme-assisted integration systems include the Cre recombinase-lox target system (e.g., as described in Baubonis, W. and Sauer, B. (1993) Nucl. Acids Res. 21:2025–2029; and Fukushige, S. and Sauer, B. (1992) Proc. Natl. Acad. Sci. USA 89:7905–7909) and the FLP recombinase-FRT target system (e.g., as described in Dang, D. T. and Perrimon, N. (1992) Dev. Genet. 13:367–375; and Fiering, S. et al. (1993) *Proc. Natl. Acad. Sci. USA* 90:8469–8473).

Media which may be used in the practice of the invention include any media which are compatible with the transfected eucaryotic cells of the present invention. Such media are commercially available (e.g. from Gibco/BRL).

Alternatively, it is possible to down regulate the expression of a protein in a transgenic animal of the present invention by administering to the animal tetracycline or tetracycline analogue. The tetracycline or tetracycline may be administered by any means that achieves its intended purpose, e.g. by parenteral, subcutaneous, intravenous, intramuscular, intraperitoneal, transdermal, or buccal routes. Alternatively, or concurrently, administration may be by the oral route (see e.g., Example 2). The dosage administered will be dependent upon the age, health, and weight of the animal, kind of concurrent treatment, if any, and frequency of treatment. To up regulate the expression of the protein, the administration of tetracycline or tetracycline analogue may then be interrupted.

The invention also relates to a kit comprising a carrier means having in close confinement therein at least two container means such as tubes, vials, bottles and the like, each of which containing a polynucleotide molecule which can be used in the practice of the invention. In particular, the invention relates to a kit comprising a carrier means having in close confinement therein at least two container means, wherein a first container means contains a first polynucleotide molecule coding for a transactivator fusion protein comprising a prokaryotic tet repressor and a protein capable of activation transcription in eucaryotes in a form suitable for homologous recombination; and a second container means contains a second polynucleotide molecule comprising a minimal promoter operably linked to at least one tet operator sequence, wherein the second polynucleotide molecule is capable of being ligated to a heterologous gene sequence coding for a polypeptide and activating the expression of the heterologous protein.

The invention also relates to kits comprising a carrier means having in close confinement therein at least two container means, wherein a first container means contains a eucaryotic cell transfected with a first polynucleotide molecule coding for a transactivator fusion protein comprising a prokaryotic tet repressor and a protein capable of activation transcription in eucaryotes in a form suitable for homologous recombination; and a second container means contains a second polynucleotide molecule comprising a minimal promoter operably linked to at least one tet operator sequence, wherein the second polynucleotide molecule is capable of being ligated to a heterologous gene sequence coding for a polypeptide and activating expression of the polypeptide.

The invention is widely applicable to a variety of situations where it is desirable to be able to turn gene expression "on" and "off", or regulate the level of gene expression, in a rapid, efficient and controlled manner without causing pleiotropic effects or cytotoxicity. The invention may be particularly useful for gene therapy purposes in humans, in treatments for either genetic or acquired diseases. The general approach of gene therapy involves the introduction of one or more nucleic acid molecules into cells such that one or more gene products encoded by the introduced genetic material are produced in the cells to restore or enhance a functional activity. For reviews on gene therapy approaches see Anderson, W. F. (1992) *Science* 256:808–813; Miller, A. D. (1992) *Nature* 357:455–460; Friedmann, T. (1989) *Science* 244:1275–1281; and Cournoyer, D., et al. (1990) *Curr. Opin. Biotech.* 1:196–208. However, current gene therapy vectors typically utilize constitutive regulatory elements which are responsive to endogenous transcriptions factors. These vector systems do not allow for the ability to modulate the level of gene expression in a subject. In contrast, the regulatory system of the invention provides this ability.

To use the system of the invention for gene therapy purposes, at least one DNA molecule is introduced into cells of a subject in need of gene therapy (e.g., a human subject suffering from a genetic or acquired disease) to modify the cells. The cells are modified to contains 1) nucleic acid encoding a tTA of the invention in a form suitable for expression of the tTA in the host cells and 2) a gene of interest (e.g., for therapeutic purposes) operatively linked to a tTA-responsive promoter (e.g., a tet operator sequence(s) and minimal promoter). Preferably, one or both of these DNA molecules is integrated into a predetermined location within a chromosome of the human cells by homologous recombination. A single DNA molecule encoding both components of the regulatory system of the invention can be used, or alternatively, separate DNA molecules encoding each component can be used. The cells of the subject can be modified ex vivo and then introduced into the subject or the cells can be directly modified in vivo by conventional techniques for introducing nucleic acid into cells. Expression of the gene of interest in the cells of the subject is stimulated in the absence of Tc or a Tc analogue, whereas expression is then inhibited by administering Tc or a Tc analogue to the patient. The level of gene expression can be varied depending upon which particular Tc analogue is used as the inducing agent. Additionally, expression of the gene of interest can be adjusted according to the medical needs of the individual, which may vary throughout the lifetime of the individual. Thus, the regulatory system of the invention offers the advantage over constitutive regulatory systems of allowing for modulation of the level of gene expression depending upon the requirements of the therapeutic situation.

Genes of particular interest to be expressed in cells of a subject for treatment of genetic or acquired diseases include those encoding adenosine deaminase, Factor VIII, Factor IX, dystrophin, $\beta$-globin, LDL receptor, CFTR, insulin, erythropoietin, anti-angiogenesis factors, growth hormone, glucocerebrosidase, $\beta$-glucouronidase, $\alpha$1-antitrypsin, phenylalanine hydroxylase, tyrosine hydroxylase, ornithine transcarbamylase, arginosuccinate synthetase, UDP-glucuronysyl transferase, apoA1, MDR1 and MRP multi-drug resistance genes, TNF, soluble TNF receptor, interleukins (e.g., IL-2), interferons (e.g., $\alpha$- or $\gamma$-IFN) and other cytokines and growth factors.

Gene therapy applications of particular interest in cancer treatment include overexpression of a cytokine gene (e.g., TNF-$\alpha$) in tumor infiltrating lymphocytes or ectopic expression of cytokines in tumor cells to induce an anti-tumor immune response at the tumor site), expression of an enzyme in tumor cells which can convert a non-toxic agent into a toxic agent, expression of tumor specific antigens to induce an anti-tumor immune response, expression of tumor suppressor genes (e.g., p53 or Rb) in tumor cells, expression of a multidrug resistance gene (e.g., MDR1 and/or MRP) in bone marrow cells to protect them from the toxicity of chemotherapy.

Gene therapy applications of particular interest in treatment of viral diseases include expression of trans-dominant negative viral transactivation proteins, such as trans-dominant negative tat and rev mutants for HIV or trans-dominant ICp4 mutants for HSV (see e.g., Balboni, P. G. et al. (1993) J. Med. Virol. 41:289–295; Liem, S. E. et al. (1993) Hum. Gene Ther. 4:625–634; Malim, M. H. et al. (1992) J. Exp. Med. 176:1197–1201; Daly, T. J. et al. (1993) Biochemistry 32:8945–8954; and Smith, C. A. et al. (1992) Virology 191:581–588), expression of trans-dominant negative envelope proteins, such as env mutants for HIV (see e.g., Steffy, K. R. et al. (1993) J. Virol. 67:1854–1859), intracellular expression of antibodies, or fragments thereof, directed to viral products ("internal immunization", see e.g., Marasco, W. A. et al. (1993) Proc. Natl. Acad. Sci. USA 90:7889–7893) and expression of soluble viral receptors, such as soluble CD4.

The regulatory system of the invention can also be used to express a suicide gene (such as a ricin or HSV tk gene) in cells in a conditional manner to allow for destruction of the cells (e.g., in vivo) following a particular therapy. For example, a suicide gene can be introduced into tumor cells to be used for anti-cancer immunization or into the viral genome of a live attenuated viral to be used as a vaccine. The tumor cells or viral vaccine carrying the suicide gene are administered to a subject in the presence of Tc (or analogue thereof). Following immunization, the drug is withdrawn (e.g., administration is stopped), thereby inducing expression of the suicide gene to destroy the tumor cells or cells carrying the live virus.

Cells types which can be modified for gene therapy purposes include hematopoietic stem cells, myoblasts, hepatocytes, lymphocytes, airway epithelium and skin epithelium. For further descriptions of cell types, genes and methods for gene therapy see e.g., Wilson, J. M. et al. (1988) Proc. Natl. Acad. Sci. USA 85:3014–3018; Armentano, D. et al. (1990) Proc. Natl. Acad Sc. USA 87:6141–6145; Wolff, J. A. et al. (1990) Science 247:1465–1468; Chowdhury, J. R. et al. (1991) Science 254:1802–1805; Ferry, N. et al. (1991) Proc. Natl. Acad. Sci. USA 88:8377–8381; Wilson, J. M. et al. (1992) J. Biol. Chem. 267:963–967; Quantin, B. et al. (1992) Proc. Natl. Acad. Sci. USA 89:2581–2584; Dai, Y. et al. (1992) Proc. Natl. Acad. Sci. USA 89:10892–10895; van Beusechem, V. W. et al. (1992) Proc. Natl. Acad. Sci. USA 89:7640–7644; Rosenfeld, M. A. et al. (1992) Cell 68:143–155; Kay, M. A. et al. (1992) Human Gene Therapy 3:641–647; Cristiano, R. J. et al. (1993) Proc. Natl. Acad. Sci. USA 90:2122–2126; Hwu, P. et al. (1993) J. Immunol. 150:4104–4115; and Herz, J. and Gerard, R. D. (1993) Proc. Natl. Acad. Sci. USA 90:2812–2816.

The Tc-controlled regulatory system of the invention has numerous advantages properties that it particularly suitable for application to gene therapy. For example, the system provides an "on"/"off" switch for gene expression that allows for regulated dosaging a gene product in a subject. There are several situations in which it may be desirable to be able to provide a gene product at specific levels and/or times in a regulated manner, rather than simply expressing the gene product constitutively at a set level. For example, a gene of interest can be switched "on" at fixed intervals (e.g., daily, alternate days, weekly, etc.) to provide the most effective level of a gene product of interest at the most effective time. The level of gene product produced in a subject can be monitored by standard methods (e.g., direct monitoring using an immunological assay such as ELISA or RIA or indirectly by monitoring of a laboratory parameter dependent upon the function of the gene product of interest, e.g., blood glucose levels and the like). This ability to turn "on" expression of a gene at discrete time intervals in a subject while also allowing for the gene to be kept "off" at other times avoids the need for continued administration of a gene product of interest at intermittent intervals. This approach avoids the need for repeated injections of a gene product, which may be painful and/or cause side effects and would likely require continuous visits to a physician. In contrast, the system of the invention avoids these drawbacks. Moreover, the ability to turn "on" expression of a gene at discrete time intervals in a subject allows for focused treatment of diseases which involve "flare ups" of activity (e.g., many autoimmune diseases) only at times when treatment is necessary during the acute phase when pain and symptoms are evident. At times when such diseases are in remission, the expression system can be kept in the "off" state.

Gene therapy applications that may particularly benefit from this ability to modulate gene expression during discrete time intervals include the following non-limiting examples:

Rheumatoid arthritis—genes which encode gene products that inhibit the production of inflammatory cytokines (e.g., TNF, IL-1 and IL-12). can be expressed in subjects. Examples of such inhibitors include soluble forms of a receptor for the cytokine. Additionally or alternatively, the cytokines IL-10 and/or IL-4 (which stimulate a protective Th2-type response) can be expressed. Moreover, a glucocorticomimetic receptor (GCMR) can be expressed.

Hypopituitarism—the gene for human growth hormone can be expressed in such subjects only in early childhood, when gene expression is necessary, until normal stature is achieved, at which time gene expression can be downregulated.

Wound healing/Tissue regeneration—Factors (e.g., growth factors, angiogenic factors, etc.) necessary for the healing process can be expressed only when needed and then downregulated.

Anti-Cancer Treatments—Expression of gene products useful in anti-cancer treatment can be limited to a therapeutic phase until retardation of tumor growth is achieved, at which time expression of the gene product can be downregulated. Possible systemic anti-cancer treatments include use of tumor infiltrating lymphocytes which express immunostimulatory molecules (e.g., IL-2, IL-12 and the like), angiogenesis inhibitors (PF4, IL-12, etc.), Herregulin, Leukoregulin (see PCT Publication No. WO 85/04662), and growth factors for bone marrow support therapy, such as G-CSF, GM-CSF and M-CSF. Regarding the latter, use of the regulatory system of the invention to express factors for bone marrow support therapy allows for simplified therapeutic switching at regular intervals from chemotherapy to bone marrow support therapy (similarly, such an approach can also be applied to AIDS treatment, e.g., simplified switching from anti-viral treatments to bone marrow support treatment). Furthermore, controlled local targeting of anti-cancer treatments are also possible. For example, expression of a suicide gene by a regulator of the invention, wherein the regulator itself is controlled by, for example, a tumor-specific promoter or a radiation-induced promoter.

In another embodiment, the regulatory system of the invention is used to express angiogenesis inhibitor(s) from within a tumor via a transgene regulated by the system of the invention. Expression of angiogenesis inhibitors in this manner may be more efficient than systemic administration of the inhibitor and would avoid any deleterious side effects that might accompany systemic administration. In particular, restricting angiogenesis inhibitor expression to within tumors could be particularly useful in treating cancer in children still undergoing angiogenesis associated with normal cell growth.

In another embodiment, high level regulated expression of cytokines may represent a method for focusing a patients own immune response on tumor cells. Tumor cells can be traduced to express chemoattractant and growth promoting cytokines important in increasing an individual's natural immune response. Because the highest concentrations of cytokines will be in the proximity of the tumor, the likelihood of eliciting an immunological response to tumor antigens is increased. A potential problem with this type of therapy is that those tumor cells producing the cytokines will also be targets of the immune response and therefor the source of the cytokines will be eliminated before eradication of all tumor cells can be certain. To combat this, expression of viral proteins known to mask infected cells from the immune system can be placed under regulation, along with the cytokine gene(s), in the same cells. One such protein is the E19 protein from adenovirus (see e.g., Cox, Science 247:715). This protein prevents transport of class I HLA antigens to the surface of the cell and hence prevents recognition and lysis of the cell by the host's cytotoxic T cells. Accordingly, regulated expression of E19 in tumor cells could shield cytokine producer cells from cytotoxic T cells during the onset of an immune response provoked by cytokine expression. After a sufficient period of time has elapsed to eradicate all tumor cells but those expressing E19, E19 expression can be turned off, causing these cells then to fall victim to the provoked anti-tumor immune response.

Benign prostatic hypertrophy—Similar to the above, a suicide gene can be regulated by a regulator of the invention, wherein the regulator itself is controlled by, for example, a prostate-specific promoter.

The ability to express a suicide gene (e.g., an apoptosis gene, TK gene, etc) in a controlled manner using the regulatory system of the invention adds to the general safety and usefulness of the system. For example, at the end of a desired therapy, expression of a suicide gene can be triggered to eliminate cells carrying the gene therapy vector, such as cells in a bioinert implant, cells that have disseminated beyond the intended original location, etc. Moreover, if a transplant becomes tumorous or has side effects, the cells can be rapidly eliminated by induction of the suicide gene.

The regulatory system of the invention further offers the ability to establish a therapeutically relevant expression level for a gene product of interest in a subject, in contrast to unregulated constitutive expression which offers no flexibility in the level of gene product expression that can be achieved. A physiologically relevant level of gene product expression can be established based on the particular medical need of the subject, e.g., based on laboratory tests that monitor relevant gene product levels (using methods as described above). In addition to the clinical examples and gene products already discussed above with gene to dosaging of the gene product, other therapeutically relevant gene products which can be expressed at a desired level at a desired time include: Factor XIII and IX in hemophiliacs (e.g., expression can be elevated during times of risk of injury, such as during sports); insulin or amylin in diabetics (as needed, depending on the state of disease in the subject, diet, etc.); erythropoietin to treat erythrocytopenia (as needed, e.g., at end-stage renal failure); low-density lipoprotein receptor (LDLr) or very low-density lipoprotein receptor (VLDLr) for artherosclerosis or gene therapy in liver (e.g, using ex vivo implants). Applications to treatment of central nervous system disorders are also encompassed. For example, in Alzheimer's disease, "fine tuned" expression of choline acetyl transferase (ChAT) to restore acetylcholine levels, neurotrophic factors (e.g., NGF, BDNGF and the like) and/or complement inhibitors (e.g., sCR1, sMCP, sDAF, sCD59 etc.) can be accomplished. Such gene products can be provided, for example, by transplanted cells expressing the gene products in a regulated manner using the system of the invention. Moreover, Parkinson's disease can be treated by "fine tuned" expression of tyrosine hydroxylase (TH) to increase levodopa and dopamine levels.

In addition to the proteinaceous gene products discussed above, gene products that are functional RNA molecules (such as anti-sense RNAs and ribozymes) can be expressed in a controlled manner in a subject for therapeutic purposes. For example, a ribozyme can be designed which discriminates between a mutated form of a gene and a wild-type gene. Accordingly, a "correct" gene (e.g., a wild-type p53 gene) can be introduced into a cell in parallel with introduction of a regulated ribozyme specific for the mutated form of the gene (e.g., a mutated endogenous p53 gene) to remove the defective mRNA expressed from the endogenous gene. This approach is particularly advantageous in situations in which a gene product from the defective gene would interfere with the action of the exogenous wild-type gene.

Expression of a gene product in a subject using the regulatory system of the invention is modulated using tetracycline or analogues thereof. Such drugs can be administered by any route appropriate for delivery of the drug to its desired site of action (e.g., delivery to cells containing a gene whose expression is to be regulated). Depending on the particular cell types involved, preferred routes of administration may include oral administration, intravenous administration and topical administration (e.g., using a transdermal patch to reach cells of a localized transplant under the skin, such as keratinocytes, while avoiding any possible side effects from systemic treatment).

In certain gene therapy situations, it may be necessary or desirable to take steps to avoid or inhibit unwanted immune reactions in a subject receiving treatment. To avoid a reaction against the cells expressing the therapeutic gene product, a subject's own cells are generally used, when possible, to express the therapeutic gene product, either by in vivo modification of the subject's cells or by obtaining cells from the subject, modifying them ex vivo and returning them to the subject. In situations where allogeneic or xenogeneic cells are used to express a gene product of interest, the regulatory system of the invention, in addition to regulating a therapeutic gene, can also be used to regulate one or more genes involved in the immune recognition of the cells to inhibit an immune reaction against the foreign cells. For example, cell-surface molecules involved in recognition of a foreign cell by T lymphocytes can be downmodulated on the surface of a foreign cell used for delivery of a therapeutic gene product, such as by regulated expression in the foreign cell of a ribozyme which cleaves the mRNA encoding the cell-surface molecule. Particularly preferred cell surface molecules which can be downmodulated in this manner to inhibit an unwanted immune response include class I and/or class II major histocompatibility complex (MHC) molecules, costimulatory molecules (e.g., B7-1 and/or B7-2), CD40, and various "adhesion" molecules, such as ICAM-1 or ICAM-2. Furthermore, as described above regarding anti-cancer treatments, a viral protein (e.g., adenovirus E19 protein) that downmodulates expression of MHC antigens can be regulated in host cells using the system of the invention as a means of avoiding unwanted immunological reactions.

In addition to avoiding or inhibiting an immune response against a foreign cell delivering a therapeutic gene product, it may also be necessary, in certain situations, to avoid or inhibit an immune response against certain components of the regulatory system of the invention (e.g., the regulator fusion proteins described herein) that are expressed in a subject, since these fusion proteins contain non-mammalian polypeptides that may stimulate an unwanted immune reaction. In this regard, regulator fusion proteins can be designed and/or selected for a decreased ability to stimulate an immune response in a host. For example, a transcriptional activator domain for use in the regulator fusion protein can be chosen which has minimal immunogenicity. In this regard, a wild-type transcriptional activation domain of the herpes simplex virus protein VP16 may not be a preferred transcriptional activation domain for use in vivo, since it may stimulate an immune response in mammals. Alternative transcriptional activation domains can be used, as described herein, based on their reduced immunogenicity in a subject. For example, a transcriptional activation domain of a protein of the same species as the host may be preferred (e.g., a transcriptional activation domain from a human protein for use of a regulatory fusion protein in humans). Alternatively, a regulatory fusion protein of the invention can be modified to reduce its immunogenicity in subjects, e.g., by identifying and modifying one or more dominant T cell epitopes within a polypeptide of the fusion protein (e.g., either the Tet repressor moiety or the transcriptional modulator moiety, such as a VP16 polypeptide). Such T cell epitopes can be identified by standard methods and altered by mutagenesis, again by standard methods. A modified form of a regulator fusion protein can then be selected which retains its original transcriptional regulatory ability yet which exhibits reduced immunogenicity in a subject as compared to an unmodified fusion protein.

In addition to the foregoing, all conventional methods for generally or specifically downmodulating immune responses in subjects can be combined with the use of the regulatory system of the invention in situations where inhibition of immune responses is desired. General immunosuppressive agents, such as cyclosporin A and/or FK506, can be administered to the subject. Alternatively, immunomodulatory agents which may allow for more specific immunosuppression can be used. Such agents may include inhibitors of costimulatory molecules (e.g., a CTLA4Ig fusion protein, soluble CD4, anti-CD4 antibodies, anti-B7-1 and/or anti-B7-2 antibodies or anti-gp39 antibodies).

Finally, in certain situations, a delivery vehicle for cells expressing a therapeutic gene can be chosen which minimizes exposure of transplanted cells to the immune system. For example, cells can be implanted into bioinert capsules/biocompatible membranes with pores which allow for diffusion of proteins (e.g., a therapeutic gene product of interest) out of the implant and diffusion of nutrients and oxygen into the implant but which prevent entry of immune cells, thereby avoiding exposure of the transplanted cells to the immune system (as has been applied to islet cell transplantation).

Use of Conditional Knockout Animals as Models for Human Disease

The transgenic and conditional knockout animals of the invention are also useful for creating animal models of human disease, in particular for determining the role of a gene of interest in the progression of a disease state. Conventional knockout technology, in which a gene is disrupted at an embryonic stage to produce an animal in which the gene product is never expressed, only allows one to evaluate the role of the gene product in the initiation of a disease condition (e.g., the disease condition never develops in the animals). This system suffers from the limitation of yielding information valid only for evaluating the possible prophylactic effect of inhibiting the gene product. However, the conditional knockout system of the invention allows one to evaluate the effect of inhibiting the expression of a particular gene product on disease progression even after the disease state has been initiated. For example, a homologous recombinant animal can be created in which an endogenous gene thought to be involved in the progression of a disease state is operatively linked to at least one tet operator sequence to confer tTA-mediated regulation on the gene. Thus, the gene is only expressed when tTA binds to the tet operator sequences, which occurs only in the absence of tetracycline. This animal can then be crossbred to a second animal transgenic for the tTA gene to create double transgenic animals in which, in the absence of tetracycline, tTA binds to the tet operator-linked gene of interest to thereby keep the gene of interest turned "on" in the animals until it is desirable to turn the gene "off". A disease state can then be induced in the double transgenic animals. After progression of the disease state for an interval of time, expression of the tet operator linked gene of interest can be turned "off" by administering tetracycline (or analogue) to the animal. The effect of ablating expression of the gene product of interest after initiation of the disease state can thus be evaluated. This approach has the advantage that it yields valid information regarding the value of inhibiting a gene product after the onset of a disease, a situation more closely resembling the typical therapeutic regimen in human disease.

In a non-limiting example of this approach of applying the conditional knockout system to the study of models of human disease states, a double transgenic animal as described above is created in which the gene for an interleukin-1-β converting enzyme (ICE), which cleaves interleukin-1β(IL-1β) to its active form, is operatively linked to at least one tet operator sequence. IL-1β is thought to be involved in the progression of diseases such as septic shock, inflammatory diseases and autoimmune diseases. Since ICE is necessary for the production of active IL-1β, one strategy for controlling IL-1β-mediated disease states is to inhibit ICE activity. Accordingly, the effect of inhibiting ICE on the progression of a disease state can be evaluated in the double transgenic animals as follows. In the absence of tetracycline, expression of ICE in the double transgenic animals is kept "on" by the tTA. Thus, in the absence of Tc, a disease condition can be induced while ICE is still being expressed. For example, sepsis can be induced in the animals by injection of lipopolysaccharide (LPS). After induction of sepsis, tetracycline (or an analogue thereof) can be administered to the animal to remove the tTA bound to the tet operator-linked ICE gene, thereby inhibiting the expression of the ICE gene. The effect of inhibiting ICE expression after initiation of sepsis can thus be evaluated. Additional suitable applications of this approach to the regulation of other gene products thought to be involved in the progression of a various disease states will be readily apparent to the skilled artisan.

Additional examples of genes which may be of particular interest for regulation using the conditional knockout system of the invention include cell cycle regulators. For example, the system can be used to evaluate the role of genes in regulating the progression of cells through the cell cycle. Typically, aberrant or ectopic expression of cell cycle regulators in cells is expected to lead to cell cycle arrest and, consequently, results in an inability to isolate cells expressing such cell cycle regulators. Accordingly, experimental expression of cell cycle regulators has been hindered by the lack of suitable methods for tightly regulating the expression of cell cycle regulators. In contrast, an experimental cell line in which a gene encoding a cell cycle regulator is controlled using the regulatory system of the invention can be grown in the presence of tetracycline (or analogue) until induction of gene expression is desired. More specifically, this regulated expression of cell cycle regulators may be useful in identifying genes and gene products important in enabling natural anti-cancer processes to occur.

The regulatory system of the invention can also be used to produce and isolate a gene product (e.g., protein) of interest. Large scale production of a protein of interest can be accomplished using cultured cells in vitro which have been modified to contain 1) nucleic acid encoding a tTA of the invention in a form suitable for expression of the tTA in the host cells and 2) a gene of interest (e.g., encoding a protein of interest) operatively linked to a tTA-responsive promoter (e.g., a tet operator sequence(s) and minimal promoter). For example, mammalian, yeast or fungal cells can be modified to contain these nucleic acid components as described herein. Alternatively, an insect cell/baculovirus expression system can be used. To produce and isolate a gene product of interest, a host cell (e.g., mammalian, yeast or fungal cell) carrying the two components of the regulatory system of the invention (e.g., nucleic acid encoding a tTA and a gene of interest, encoding the gene product of interest, linked to a tTA-responsive promoter) are first grown in a culture medium in the presence of tetracycline or a tetracycline analogue. Under these conditions, expression of the gene of interest is repressed. Next, the concentration of tetracycline or the tetracycline analogue in the culture medium is reduced to stimulate transcription of the gene of interest. The cells are then further cultured in the absence of Tc (or analogue thereof) until a desired amount of the gene product encoded by the gene of interest is produced by the cells. The gene product can then be isolated from harvested cells or from the culture medium by standard techniques.

The invention also provides for large scale production of a protein of interest in animals, such as in transgenic farm animals. Advances in transgenic technology have made it possible to produce transgenic livestock, such as cattle, goats, pigs and sheep (reviewed in Wall, R. J. et al. (1992) *J. Cell. Biochem.* 42:113–120; and Clark, A. J. et al. (1987) *Trends in Biotechnology* 5:20–24). Accordingly, transgenic livestock carrying in their genome the components of the regulatory system of the invention can be constructed. Thus, by appropriate mating, double transgenic animals carrying a transgene encoding a tTA of the invention and a transgene comprising a tTA-responsive promoter linked to a gene of interest (the gene of interest may be either an exogenous or an endogenous gene) can be obtained. In the absence of Tc (or analogue), expression of the gene of interest is stimulated in the transgenic animals. By administering Tc (or analogue) to the animal, expression of the gene of interest can be inhibited. Protein production can be targeted to a particular tissue by linking the nucleic acid encoding the tTA to an appropriate tissue-specific regulatory element(s) which limits expression of the transactivator to certain cells. For example, a mammary gland-specific regulatory element, such as the milk whey promoter (U.S. Pat. No. 4,873,316 and European Application Publication No. 264,166), can be linked to the tTA-encoding transgene to limit expression of the transactivator to mammary tissue. Thus, in the absence of Tc (or analogue), the protein of interest will be produced in the mammary tissue of the transgenic animal, whereas protein expression can be downmodulated by administering Tc or a Tc analogue. The protein can be designed to be secreted into the milk of the transgenic animal, and if desired, the protein can then be isolated from the milk.

Having now generally described this invention, the same will be understood by reference to the following examples which are provided herein for purposes of illustration only and are not intended to be limiting unless otherwise specified. The contents of all publications, references, patents and published patent applications cited throughout the application are hereby incorporated by reference.

EXAMPLE 1

Regulation of Gene Expression in Cells by tTA
Materials and Methods

Construction of the transactivators tTA and tTA$_S$. The tetR sequence was originally recovered from pWH510 (Altschmied et al., EMBO J. 7:4011–4017 (1988), the disclosure of which is fully incorporated by reference herein) by PCR and inserted into pUHD10-1 (Deustchle et al., Proc. Natl. Acad. Sci. USA 86:5400–5404 (1989)), resulting in pUHD14-1 (see, the Dissertation of Manfred Gossen, "Prokaryotic Repressor Operator Systems in the Control of Eucaryotic Gene Expression, Heidelberg University, 1993, the contents of which are fully incorporated by reference herein). A unique AflII cleavage site, overlapping the tetR stop codon in this plasmid construct, allows for the in-frame insertion of coding sequences. To generate tTA, a 397-basepair (bp) MluI/FokI fragment of pMSVP16 (Triezenberg et al., Genes Dev. 2:718–729 (1988), the disclosure of which is fully incorporated by reference herein), coding for the C-terminal 130 amino acids of VP16 of HSV, was blunted by filling in the protruding ends with T4 DNA polymerase. This DNA was inserted in pUHD14-1, previously cleaved with AflII, and blunted by mung bean nuclease. The resulting plasmid, pUHD15-1, encodes the tTA sequence (FIG. 1, panel a) under the control of the P$_{hCMV}$ (human cytomegalovirus promoter IE; see below). In a homologous approach, a DNA fragment coding for the 97-amino acid C-terminal portion of VP 16 was fused to tetR by PCR-mediated cloning. The resulting plasmid, pUHD15-1, encodes the smaller version of the trans-activator, tTA$_S$ (FIG. 1, panel a).

Construction of P$_{hCMV}$* and the Luciferase Reporter Plasmid.

Plasmid pUHC13-1 is a derivative of pUHD10-1 (Deuschle et al., Proc. Natl. Acad. Sci. USA 86:5400–5404 (1989)). It contains the promoter-enhancer sequence of PhCMV, spanning position +75 to position −675 (Boshart et al., Cell 41:521–530 (1985)). This promoter is followed by a polylinker and the luciferase gene of *Photinus pyralis* fused to the SV40 small-t intron and poly(A) signal. The latter elements and the luciferase gene were transferred from pSV2L,AΔ5' (DeWit et al., Mol. Cell. Biol. 7:725–737 (1987)). By this transfer, the N-terminus of luciferase has been modified as described (Deuschle et al., Proc. Natl. Acad. Sci. USA 86:5400–5404 (1989)). The enhancer region of P$_{hCMV}$ was removed by PCR-mediated cloning, whereby a Xho I site was introduced adjacent to position −53. The resulting minimal promoter, P$_{hCMV}$* (FIG. 1, panel b) is part of the reporter plasmid pUHC13-2.

Construction of P$_{hCMV}$*-1 and P$_{hCMV}$*-2

To combine P$_{hCMV}$* with tet operators, the 19-bp inverted repeat sequence of operator 02 of Tn10 (Triezenberg et al., Genes Dev. 2:718–729 (1988)) was synthesized as part of a 42-bp DNA fragment [SEQ ID NO: 10]:

(upper strand: 5' TCGAGTTTACCACTCCCTATCAGT-GATAGAGAAAAGTGAAAG 3'). Upon annealing, the two complementary strands exposed the compatible protruding ends of a Xho I and a Sal I cleavage site at the 5 and 3' ends, respectively. Ligation of this fragment into the Xho I site of the polylinker of pT81-luc (Nordeen, S. K., BioTechniques 6:454–457 (1988)) created, upon cloning, single as well as multiple inserts of operator sequences upstream of a thymidine kinase (tk) minimal promoter from HSV contained in pT81-luc. The tk promoters containing one, two, and seven operator sequences were examined for their ability to be activated in transient expression experiments using the HeLa cell line HtTa-1 (see below). All constructs were active in tTA producing cells in a tetracycline-dependent manner. The heptameric version of the tetO sequences caused by far the highest activation of all Ptk-tetO constructs. It therefore was removed as a XhoI/Sal fragment and transferred into pUHC13-2. Due to the asymmetric location of the tetO within the polylinker of pT81-luc, the resulting plasmids pUHC13-3 and pUHC13-4 contain the heptameric tetOs in two orientations differing in the distance between the operators and position +1 of $P_{hCMV}$ by 19 bp. The two tetO-containing promoters were designated $P_{hCMV}^*$-1 and $P_{hCMV}^*$-2 (FIG. 1, panel b).

Band-Shift Assay

Cytoplasmic and nuclear cell extracts from~$2\times10^6$ cells were prepared as described by Andrews and Faller, Nucl. Acids Res. 19:2499 (1991), except that the cytoplasmic protein fraction was centrifuged once more (1 hr, 100,000× g). Nuclear proteins were extracted by a buffer containing 20 mM Hepes-KOH (pH 7.9), 25% glycerol, 420 mM NaCL, 1.5 mM $MgCl_2$, 0.2 mM EDTA, 0.5 mM dithiothreitol, and 0.5 mM phenylmethylsulfonyl fluoride. Aliquots (5 µl) of nuclear extracts were mixed with 15 µl of binding buffer (10 mM Tris HCl, pH 7.5/10 mM MgCl2) containing 20 µg of calf thymus DNA, 5 µg of bovine serum albumin, and 2 fmol of $^{32}$P-labeled tetO DNA. The tetO DNA was isolated from pUHC13-3 as a 42-bp Taq I fragment whose protruding ends were filled in by Klenow enzyme in the presence of [α-$^{32}$P] dCTP. After 20 min. at room temperature, aliquots of the binding reaction mixture were loaded onto a 5% polyacrylamide/0.07% bisacrylamide gel. Electrophoresis was carried out in 90 mM Tris base/90 mM boric acid/3 mM EDTA at 5 V/cm.

Luciferase Assays.

Cell grown to ~80% confluency in 35-mm dishes in Eagle's minimum essential medium were washed with 2 ml of phosphate-buffered saline before they were lysed in 25 mM Tris phosphate, pH 7.8/2 mM dithiothreitol/2 mM diaminocyclohexanetetraacetic acid/10% glycerol/1% Triton X-100 for 10 min at room temperature. The lysate was scraped off the culture dishes and centrifuged for 10 sec in an Eppendorf centrifuge. Next, aliquots (10 µl) of the supernatant were mixed with 250 µl of 25 mM glycylglycine/15 mM $MgSO_4$/5 mM ATP and assayed for luciferase activity in a Lumat LB9501 (Berthold, Wildbad, F.R.G.) using the integral mode (10 sec). D-Luciferin (L6882, Sigma) was used at 0.5 mM. The background signal measured in extracts of HeLa cells that did not contain a luciferase gene was indistinguishable from the instrumental background [80–120 relative light units (rlu)/10 sec). Protein content of the lysates was determined according to Bradford (Bradford, M. M., Anal. Biochem. 72:248–254 (1976)).

RESULTS

Construction and Characterization of the tTA.

To convert the prokaryotic tet repressor into a eucaryotic transactivator, it was fused to the negatively charged C-terminal domain of HSV-VP16, known to be essential for transactivation. (Triezenberg et al., Genes Dev. 2:718–729 (1988)). Sequences coding for either a 97- or a 127-amino acid C-terminal portion of VP 16 were fused to the tetR gene, resulting in the coding sequences of tTAS and tTA, respectively (FIG. 1, panel a). In plasmids coding for tTA (pUHD 15-tTAs (pUHD 151-1), the transactivator sequences are flanked upstream by $P_{hCMV}$ and downstream by the SV40 poly(A) site. The two fusion proteins did not differ in their functional in vivo properties.

HeLa cells transiently transfected with pUHD15-1 produced a fusion protein of the expected molecular mass (37 kDa), as demonstrated in immunoblots of the electrophoretically separated cytoplasmic and nuclear extracts (FIG. 2, panel a). When nuclear extracts were mixed with the tetO DNA, the electrophoretic mobility of the DNA was diminished. The specificity of the interaction between tTA and operator DNA was confirmed by the finding that no mobility change for tetO DNA was detectable in the presence of the specific inducer tetracycline (FIG. 2, panel b).

Construction of a tTA-Dependent Promoter.

To generate promoters activatable by tTA, tetOs were inserted upstream of minimal promoter sequences. For $P_{hCMV}$, the upstream enhancer region was removed by PCR and a Xho I cleavage site was introduced adjacent to position −53. This minimal promoter, designated $P_{hCMV}^*$, spans the original $P_{hCMV}$ sequence from +75 to −53 (+1 being the first nucleotide transcribed) and, in addition, contains a Stu I site around −31 (FIG. 1, panel b). tetO sequences were fused to this core promoter by insertions at the Xho I site (FIG. 1).

The tetO sequence 02 of Tn10 is a 19-bp inverted repeat to which tetR binds as a 46-kDa dimer (Hillen & Wissmann, "Topics in Molecular and Structural Biology," in Protein-Nucleic Acid Interaction, Saeger & Heinemann, eds., Macmillan, London, 1989, Vol. 10, pp. 143–162). It was chemically synthesized and ligated into the Xho I cleavage site of the polylinker located upstream of the minimal tk promoter in plasmid pT81-luc (Nordeen, S. K., BioTechniques 6:454–457 (1988)). Multiple insertions of tetOs created a set of promoters that contained between 1 and 7 tetO sequences upstream from position −81 of the tk promoter. A Xho I/Sal I fragment containing 7 tetOs, fused head to tail, was recovered from one of the constructs and transferred into the Xho I site upstream of $P_{hCMV}^*$. Due to the asymmetry of the Xho I/Sal I fragment, two $P_{hCMV}^*$-tetO constructs were obtained that differ in the distance between the operators and position +1 of $P_{hCMV}$, which is 95 bp for $P_{hCMV}^*$-1 and 76 bp for $P_{hCMV}^*$-2. The plasmids containing these promoters are designated pUHC13-3 and pUHC13-4, respectively (FIG. 1, panel b). When HeLa cells were transiently transfected with these plasmids, high levels of luciferase activity were monitored whenever the cells were cotransfected with pUHD15-1, which provided the coding sequence of tTA. Little activity was observed with cultures grown in the presence of tetracycline (1.0 µg/ml) or with plasmids containing $P_{hCMV}^*$ only. Since $P_{hCMV}^*$-1 and $P_{hCMV}^*$-2 were activated by tTA to a significantly higher degree than any of the Ptk constructs, the latter ones were not investigated further.

Quantitation of $P_{hCMV}^*$-1 and $P_{hCMV}^*$-2 Activation by tTA.

To quantify the stimulation of $P_{hCMV}^*$-tetO constructs by tTA, HeLa cell lines were established that contained the $P_{hCMV}^*$-1—or the $P_{hCMV}^*$-2-luciferase, as well as the $P_{hCMV}$-tTA expression units stably integrated. Conditions for culturing and selecting cells have been described (Deuschle et al., Proc. Natl. Acad. Sci. USA 86:5400–5405 (1989)). In a first step, cells were cotransfected with pUHD15-1 and pSV2neo (Southern &: Berg, J. Mol. Appl. Genet. 1:327–341 (1982)). Clones resistant to G418 were assayed for transactivation of $P_{hCMV}$*-1 by transient transfection with pUHC13-3. In all HeLa cell clones in which the tetracycline-responsive promoters were active, tTA was not detectable by Western blots or by immunofluorescence. Its presence was just barely visible in electrophoretic mobility shift experiments of highly labeled tetO DNA. This indicates very low intracellular concentrations of tTA and may reflect a selection against squelching effects caused by higher concentrations of VP16-activating domains (Gill & Ptashne, Nature (London) 334:721–724 (1988)).

One of the positive clones, HtTA-1, was then cotransfected with a plasmid carrying the hygromycin-resistance gene (pHMR272; Bernard et al., Exp. Cell Res. 158:237–243 (1985)) and either pUHC13-3 or pUHC13-4, resulting in the X and T series of clones, respectively. Clones resistant to hygromycin and G418 were assayed for luciferase activity. As shown in Table 1 below, in the absence of tetracycline, this activity differed in individual clones by almost four orders of magnitude. However, in all cases, the luciferase activity was sensitive to tetracycline in the culture. This demonstrates that the expression of luciferase is dependent on the function of tTA, which obviously is capable of activating promoter constructs $P_{hCMV}$*-1 and $P_{hCMV}$*-2.

TABLE 1

Tetracycline-dependent Luciferase Activity of Different HeLa Cell Clones
Luciferase activity, rlu/$\mu$ of protein

| Clone | With Tc | Without Tc | Activation Factor |
|---|---|---|---|
| T7  | 1074 ± 75 | 79,197 ± 2,119 | 7.3 × $10^1$ |
| T11 | 2.5 ± 0.4 | 34,695 ± 1,127 | 1.3 × $10^4$ |
| T12 | 3.5 ± 0.9 | 35,298 ± 5,009 | 1 × $10^4$ |
| T14 | ≤2 | 33 ± 4 | ≥1.5 × $10^1$ |
| T15 | 286 ± 47 | 49,070 ± 2,784 | 1.7 × $10^2$ |
| T16 | ≤2 | 541 ± 133 | ≥2.7 × $10^2$ |
| X1  | ≤2 | 257,081 ± 40,137 | ≥2.7 × $10^5$ |
| X2  | ≤2 | 104,840 ± 20,833 | ≥5 × $10^4$ |
| X7  | 75 ± 7 | 125,745 ± 18,204 | 1.6 × $10^3$ |

The HeLa cell clone HtTA-1, which constitutively expresses tTA, was cotransfected with pUHC13-3 or pUHC13-4 and pHMR272. Hygromycin-resistant clones were examined for luciferase activity. Nine clones identified were subcloned and luciferase activity was quantified in the presence (1 $\mu$/ml) and absence of tetracycline (Tc). Values are arithmetic means of three independent luciferase determinations (from three independently grown cultures). Luciferase activities of <2 rlu/$\mu$g of protein are too close to the instrumental background to be quantified.

When the luciferase activity within various clones was monitored in the presence and absence of tetracycline hydrochloride (Sigma), two remarkable results emerged. (i) In all clones tested, tTA greatly stimulated promoter activity, even up to five orders of magnitude in clone X1. (ii) In clones T14, T16, X1 and X2 (Table 1), tetracycline reduced luciferase activity to values that cannot be quantified even at high protein concentration of extracts due to instrumental limitations (i.e., rlu/$\mu$g of protein>2). This demonstrates that $P_{hCMV}$*-1 and $P_{hCMV}$*-2 are virtually silent when integrated in the proper genomic environment and that their activity depends exclusively on the action of tTA.

The tTA inactivation studies were carried out with 1 $\mu$g of tetracycline per ml in the culture medium. A partial inactivation of tTA is, however, readily achieved with tetracycline concentrations below 0.1 $\mu$g/ml, as shown in FIG. 3, panel a. In the two clones analyzed (T12 and X1), a stepwise reduction of the tetracycline concentration in the medium gradually increased the luciferase activity. These results again demonstrate that, in the case of clone X1, tTA can regulate transcriptional activity, as monitored by luciferase activity, by over five orders of magnitude. Moreover, at tetracycline concentrations sufficient for full inactivation of tTA (0.1 $\mu$g/ml), no change in growth behavior or morphology of HeLa cells occurs. Only at tetracycline concentrations well above 10 $\mu$g/ml were such changes observed upon prolonged incubation.

Kinetics of Tetracycline Action.

The time course of tetracycline action was analyzed in cultures grown in the absence or presence of tetracycline. At time 0, the antibiotic was added to the tetracycline-free cultures (final concentration, 1 $\mu$g/ml), whereas the tetracycline-containing cultures were rinsed and incubated in fresh antibiotic-free medium (FIG. 3 panel b). At various times, cells were harvested and analyzed for luciferase activity. As shown in FIG. 3 panel b, the depletion of tetracycline leads to a rapid induction of luciferase activity reaching>20% of the fully induced level within 12 hr. A similarly rapid reduction of luciferase activity was observed when tetracycline was added to the fully active tetracycline-free system: within 8 hr activity dropped to about 10% and reached<2% of its original value after 12 hr.

The fusion of the Tn10-derived *E. coli* tetR with the activation domain of VP16 from HSV has generated a transactivator exhibiting all of the properties required for the specific and stringent regulation of an individual gene in a eucaryotic cell. The transactivator tTA produced in HeLa cells binds specifically to tetO sequences in vitro. This association is prevented by tetracycline. When bound to tetOs placed upstream of minimal promoters, tTA efficiently activates transcription from such promoters in vivo in a tetracycline-dependent manner. The transactivator is produced in HeLa cells in amounts sufficiently high for strong activation of transcription though low enough to avoid any detectable squelching effects (Gill & Ptashne Nature (London) 334:721–724 (1988)).

The usefulness of heterologous regulatory systems as the one described here depends decisively on quantitative parameters such as the extent of inactivation and the efficiency of activation of gene expression as well as the kinetics of transition from one state to the other. For the tet system, these parameters were measured in HeLa cell lines that constitutively express tTA and that also contain the luciferase gene stably integrated and under the control of tTA-dependent promoters. The clones characterized thus far express the luciferase gene to various extents. This is not surprising since differences in the integration sites and in the number of integrated transcription units would be expected. However, in all cases, the expression of luciferase is sensitive to tetracycline. In some clones, tetracycline has the most dramatic effect of reducing the luciferase activity from high levels over several orders of magnitude to background. This demonstrates that in HeLa cells, the two promoters $P_{hCMV}$*-1 and $P_{hCMV}$*-2, have no measurable intrinsic activity. Their function strictly depends on tTA. The residual luciferase activity observed in some clones in the presence of tetracycline must therefore be due to position effects.

The tTA-dependent promoters can be kept in a partially activated state by low concentrations of tetracycline. As shown in FIG. 3 panel a, varying the tetracycline concentration between 0 and 0.1 $\mu$g/ml allows adjustment of promoter activity within a range of several orders of magnitude. This may allow assessment also of quantitative parameters of gene function in vivo.

The activation and inactivation of tTA by the antibiotic appears to be not only an efficient but also a rapid process. When cells from tetracycline containing medium are shifted to tetracycline-free medium, significant luciferase activity is induced within 4 hr and >20% of the steady-state level is reached within 12 hr after the shift. Interestingly, even the cultures that were only exposed to tetracycline-free medium during the washing procedure before reincubation in tetracycline-containing medium show a small but reproducible increase in luclferase activity that is still detectable after 4 hr (FIG. 3b).

When tetracycline is added to a culture of X1 cells, luciferase activity is reduced ~10-fold within 8 hr and >50 fold within 12 hr. This decrease is remarkably fast if one takes into account the half-life of luciferase of around 3 hr reported for eucaryotic cells (measured by cycloheximide inhibition: Ilguyen et al., J. Biol. Chem. 264:10487–10492 (1989); Thompson et al., Gene 103:171–177 (1991)) and indicates a rapid uptake of tetracycline by HeLa cells followed by a fast and efficient shutdown of transcription. Although the half-life of luciferase and its mRNA remains to be determined in this system, these conclusions are supported by observations in plant cells, where tetracycline inactivates tetR within <30 min (Gatz et al., Mol. Gen. Genet 227:229–237 (1991)).

Taken together, these data show that tetracycline, unlike IPTG in a eucaryotic lacR/O-based system, is able to act fast in cultures of eucaryotic cells. The possibility of rapidly switching the activity of a tTA-dependent promoter not only is of interest in studying gene function itself but also should allow analysis of mRNA decay rates of individual genes under physiological conditions.

In clone X1, tetracycline reduces luciferase activity reproducibly by five orders of magnitude. This suggests that binding of tetracycline to tTA may lower the association constant between the transactivator and its operator to a much greater extent than that measured for tetR (Takahasi et al., J. Mol. Biol. 187:341–348 (1986)) and as described for IPTG in the lacR/O system, where the binding constant $k_{RO}$ is reduced only 1000-fold by the inducer (Barkley and Bourgeois in The Operon, Miller and Reznikoff(eds.), Cold Spring Harbor Laboratory, Cold Spring Harbor, N.Y., 1980; pp. 177–220.)

On the other hand, the results obtained in transient experiments with minimal tk promoters fused to single, dimeric, and heptameric tetO sequences strongly suggest a synergistic effect of multiple tTA binding sites. The efficient inactivation of tTA by tetracycline is therefore most likely due to a large difference in the binding constants of tTA and tTA/tetracycline for the tetO and the nonlinear effect of tetracycline interfering with a cooperative process.

In conclusion, the results indicate that promoter-activating systems as described here are most promising for regulating individual genes in higher eucaryotic cells for several reasons. (i) For activators, in particular when acting through a cooperative mechanism, intracellular concentrations can be kept low, ensuring an efficient inactivation by the effector—in this case, tetracycline. By contrast, repressors in general complete directly with transcription factors and/or RNA polymerases for binding within a promoter region. In the absence of cooperativity, however, the window at which the repressor concentration is sufficiently high for tight expression but still low enough for efficient induction may be narrow and not easily adjustable in different systems. (ii) In an activating system, as described here, the synthesis of tTA can be driven by a tissue-specific promoter, whereas the tTA dependent promoters are expected to function tissue independently, since they may require only general transcription factors in addition to tTA. By contrast, in a repressor-based system in which operators have to be placed within the context of a promoter sequence, an influence on promoter specificity cannot be excluded. (iii) The tet system offers specific advantages when compared to the intensely studied lac system. For example, tetR binds tetracycline much tighter (ka~$10^9$ M$^{-1}$; Takahashi et al., J. Mol. Biol. 187:341–348 (1986)) than lacR complexes IPTG (ka $10^6$ M$^{-1}$; Barkley & Bourgeois in The Operon, Miller & Rezinkoff, eds., Cold Spring Harbor Lab., Cold Spring Harbor, N.Y., 1980, pp. 177–220). Thus, very low, nontoxic concentrations of tetracycline function effectively. Moreover, a large number of tetracycline analogues are known, of which some appear to have far superior properties as effectors than tetracycline itself. In this context, it is interesting to note that detailed information on the pharmacological properties of tetracycline, in particular pharmacokinetic parameters, is available, which will facilitate application of this system in transgenic animals.

EXAMPLE 2

Regulation of Gene Expression in Transgenic Animals by tTA

To examine the ability of tTA to regulate gene expression in vivo, transgenic strains of mice were constructed which contained heterologous chromosomal insertions of either a tTA expression unit or a tTA-responsive promoter operably linked to a reporter gene. Single transgenic strains containing either the tTA expression unit or the tTA-responsive reporter unit were then cross bred and double transgenic progeny were identified. The double transgenic animals were then characterized as to the ability of tTA, in a tetracycline dependent manner, to regulate expression of the reporter gene. This example demonstrates that tTA effectively stimulates the expression of a gene operably linked to a tTA responsive promoter in multiple tissues of the animals in vivo in the absence of tetracycline (or analogue), whereas expression of the tTA-responsive gene is effectively inhibited in multiple tissues of the animals when tetracycline or an analogue thereof is administered to the animals. These results demonstrate that the tetracycline-controlled transcriptional regulatory system described herein functions effectively in animals, in addition to cell lines in vitro.

Generation of Mice Transgenic for a $P_{hCMV}$-tTA Expression Unit

Mice expressing tTA protein were obtained by pronuclear injection into fertilized oocytes of a 2.7 kb XhoI-PfmI fragment excised from plasmid pUHG15-1. This DNA fragment contained the tTA gene (shown in SEQ ID NO: 1) under the transcriptional control of the human CMV IE promoter (position +75 to –675) together with a rabbit β-globin polyadenylation site including an intron. The human CMV IE promoter is a constitutive promoter that allows expression of the tetR-VP16 fusion protein in many cell lines where chromosomal integration of the DNA sequence encoding tTA has occurred and is known to be functional in a variety of tissues in transgenic mice. DNA was injected into fertilized oocytes at a concentration of approximately 5 ng per μl by standard techniques. Transgenic mice were generated from the injected fertilized oocytes according to standard procedures. Transgenic founder mice were analyzed using polymerase chain reaction (PCR) and Southern hybridization to detect the presence of the tTA transgene in chromosomal DNA of the mice.

Generation of Mice Transgenic for the $P_{hCMV}*$-1 Luciferase Reporter Unit

Mice carrying a $P_{hCMV}*$-1 luc reporter gene expression unit were generated by pronuclear injection into fertilized oocytes of a 3.1 kb XhoI-EaeI fragment excised from plasmid pUHC13-3. This DNA-fragment contains the luciferase gene under transcriptional control of the tetracycline-responsive $P_{hCMV*-1}$ promoter (SEQ ID NO: 5), together with a SV40 t early polyadenylation site including an intron. DNA was injected into oocytes at a concentration of approximately 5 ng per μl and transgenic mice were generated according to standard procedures. Transgenic founder mice were analyzed using Southern hybridization to detect the presence of the $P_{hCMV*-1}$ luc transgene in chromosomal DNA of the mice.

Generation of Mice Transgenic for the $P_{hCMV*-1}$ luc and $P_{hCMV}$-tTa

Having constructed single transgenic mice expressing tTA or carrying $P_{hCMV*-1}$ luc, double transgenic mice carrying both the tTA expression vector and the luciferase reporter-units were obtained through cross breeding of heterozygous mice transgenic for one of the two transgenes. Double transgenic animals were identified by standard screenings (e.g., PCR and/or Southern hybridization) to detect the presence of both the tTA transgene and the $P_{hCMV*-1}$ luc transgene in chromosomal DNA of the mice.

Induction and Analysis of Luciferase Activity in Tissue Samples from Mice

For oral administration, tetracycline or its derivative doxycycline were given in the drinking water at a concentration of 200 μg per ml with 5% sucrose to hide the bitter taste of the antibiotics. For lactating mice, the concentration was 2 mg per ml with 10% sucrose to ensure a sufficient uptake via the milk by the young.

To analyze luciferase activity, mice were killed by cervical dislocation and tissue samples were homogenized in 2 ml tubes containing 500 μl lysis-buffer (25 mM Tris phosphate, pH 7.8/2 mM DTT/2 mM EDTA/10% glycerol/1% Triton X100) using a Ultra-Turrax. The homogenate was frozen in liquid nitrogen and centrifuged after thawing for 5 min at 15,000 g. 2–20 μl of the supernatant were mixed with 250 μl luciferase assay buffer (25 mM glycylglycine, pH 7.5/ 15 mM MgSO4/ 5 mM ATP) and luciferase activity was measured for 10 sec after the injection of 100 μl of a 125 μM luciferin solution using Berthold Lumat LB 9501. The protein concentration of the homogenate was determined using Bradford assay and luciferase activity was calculated as relative light units (rlu) per μg of total protein.

Results

Mice from 4 lines carrying the $P_{hCMV}$-tTA transgene (CT1 through CT4) were mated with mice from line L7, transgenic for $P_{hCMV*-1}$ luc. This line shows a very low but significant background of luciferase activity in different organs that is probably due to position effects at the integration side. The luciferase activity in different tissues of the double transgenic mice, either in the presence or absence of the tetracycline analogue doxycycline, is illustrated graphically in FIG. 14. High luciferase activity was detectable in five tissues of the double transgenic mice examined: heart, muscle, pancreas, thymus and tongue. The tissue pattern of activated luciferase levels (i.e., in the absence of doxycycline) in the double transgenic mice was similar to expression patterns of the hCMV IE promoter reported in the literature. This is consistent with expression of the luc reporter gene being regulated by tTA (which is expressed in the mice under the control of the hCMV IE promoter). After administration of doxycycline to the mice for 7 days, luciferase activity was reduced close to background levels observed in single transgenic mice carrying only the $P_{hCMV*-1}$ luc reporter unit (i.e., the L7 line). Depending on the individual animals used for comparison of induced and non-induced luciferase level, regulation factors up to 10,000 fold can be estimated e.g. in the pancreas. These results indicate that the tetracycline-controlled transcriptional regulatory system described herein can be used to efficiently regulate expression of genes in transgenic animals.

Equivalents

Those skilled in the art will recognize, or be able to ascertain using no more than routine experimentation, many equivalents to the specific embodiments of the invention described herein. Such equivalents are intended to be encompassed by the following claims.

What is claimed is:

1. A fusion protein which activates transcription comprising a first polypeptide which is a Tet repressor operatively linked to a second polypeptide which activates transcription in eukaryotic cells.

2. The protein of claim 1, wherein the Tet repressor is a Tn10-derived Tet repressor.

3. The protein of claim 1, wherein the second polypeptide comprises a transcription activation domain of herpes simplex virion protein 16.

4. The protein of claim 2, wherein the second polypeptide comprises the C-terminal 130 amino acids of herpes simplex virion protein 16.

5. The protein of claim 1, wherein the second polypeptide comprises a transcription activation domain selected from the group consisting of an acidic transcription activation domain, a proline-rich transcription activation domain, a serine/threonine-rich transcription activation domain and a glutamine-rich transcription activation domain.

* * * * *

SEQUENCE LISTING

```
<160> NUMBER OF SEQ ID NOS: 17

<210> SEQ ID NO 1
<211> LENGTH: 1008
<212> TYPE: DNA
<213> ORGANISM: Herpes Simplex Virus
<220> FEATURE:
<221> NAME/KEY: CDS
<222> LOCATION: (1)...(1005)
<220> FEATURE:
<221> NAME/KEY: exon
<222> LOCATION: (1)...(1008)
<220> FEATURE:
<221> NAME/KEY: mRNA
<222> LOCATION: (1)...(1008)
<220> FEATURE:
<221> NAME/KEY: misc_binding
<222> LOCATION: (1)...(207)
<220> FEATURE:
<221> NAME/KEY: misc_binding
<222> LOCATION: (208)...(335)

<400> SEQUENCE: 1
```

-continued

| | |
|---|---|
| atg tct aga tta gat aaa agt aaa gtg att aac agc gca tta gag ctg<br>Met Ser Arg Leu Asp Lys Ser Lys Val Ile Asn Ser Ala Leu Glu Leu<br>1                   5                   10                  15 | 48 |
| ctt aat gag gtc gga atc gaa ggt tta aca acc cgt aaa ctc gcc cag<br>Leu Asn Glu Val Gly Ile Glu Gly Leu Thr Thr Arg Lys Leu Ala Gln<br>                   20                   25                   30 | 96 |
| aag cta ggt gta gag cag cct aca ttg tat tgg cat gta aaa aat aag<br>Lys Leu Gly Val Glu Gln Pro Thr Leu Tyr Trp His Val Lys Asn Lys<br>              35                    40                    45 | 144 |
| cgg gct ttg ctc gac gcc tta gcc att gag atg tta gat agg cac cat<br>Arg Ala Leu Leu Asp Ala Leu Ala Ile Glu Met Leu Asp Arg His His<br>50                    55                   60 | 192 |
| act cac ttt tgc cct tta gaa ggg gaa agc tgg caa gat ttt tta cgt<br>Thr His Phe Cys Pro Leu Glu Gly Glu Ser Trp Gln Asp Phe Leu Arg<br>65                    70                   75                   80 | 240 |
| aat aag gct aaa agt ttt aga tgt gct tta cta agt cat cgc gat gga<br>Asn Lys Ala Lys Ser Phe Arg Cys Ala Leu Leu Ser His Arg Asp Gly<br>                   85                   90                   95 | 288 |
| gca aaa gta cat tta ggt aca cgg cct aca gaa aaa cag tat gaa act<br>Ala Lys Val His Leu Gly Thr Arg Pro Thr Glu Lys Gln Tyr Glu Thr<br>                  100                  105                110 | 336 |
| ctc gaa aat caa tta gcc ttt tta tgc caa caa ggt ttt tca cta gag<br>Leu Glu Asn Gln Leu Ala Phe Leu Cys Gln Gln Gly Phe Ser Leu Glu<br>                  115                  120                125 | 384 |
| aat gca tta tat gca ctc agc gct gtg ggg cat ttt act tta ggt tgc<br>Asn Ala Leu Tyr Ala Leu Ser Ala Val Gly His Phe Thr Leu Gly Cys<br>130                   135                  140 | 432 |
| gta ttg gaa gat caa gag cat caa gtc gct aaa gaa gaa agg gaa aca<br>Val Leu Glu Asp Gln Glu His Gln Val Ala Lys Glu Glu Arg Glu Thr<br>145                  150                 155                160 | 480 |
| cct act act gat agt atg ccg cca tta tta cga caa gct atc gaa tta<br>Pro Thr Thr Asp Ser Met Pro Pro Leu Leu Arg Gln Ala Ile Glu Leu<br>                  165                  170                175 | 528 |
| ttt gat cac caa ggt gca gag cca gcc ttc tta ttc ggc ctt gaa ttg<br>Phe Asp His Gln Gly Ala Glu Pro Ala Phe Leu Phe Gly Leu Glu Leu<br>                  180                  185                190 | 576 |
| atc ata tgc gga tta gaa aaa caa ctt aaa tgt gaa agt ggg tcc gcg<br>Ile Ile Cys Gly Leu Glu Lys Gln Leu Lys Cys Glu Ser Gly Ser Ala<br>                195                  200                205 | 624 |
| tac agc cgc gcg cgt acg aaa aac aat tac ggg tct acc atc gag ggc<br>Tyr Ser Arg Ala Arg Thr Lys Asn Asn Tyr Gly Ser Thr Ile Glu Gly<br>210                  215                 220 | 672 |
| ctg ctc gat ctc ccg gac gac gac gcc ccc gaa gag gcg ggg ctg gcg<br>Leu Leu Asp Leu Pro Asp Asp Asp Ala Pro Glu Glu Ala Gly Leu Ala<br>225                  230                 235                240 | 720 |
| gct ccg cgc ctg tcc ttt ctc ccc gcg gga cac acg cgc aga ctg tcg<br>Ala Pro Arg Leu Ser Phe Leu Pro Ala Gly His Thr Arg Arg Leu Ser<br>                  245                  250                255 | 768 |
| acg gcc ccc ccg acc gat gtc agc ctg ggg gac gag ctc cac tta gac<br>Thr Ala Pro Pro Thr Asp Val Ser Leu Gly Asp Glu Leu His Leu Asp<br>                  260                  265                270 | 816 |
| ggc gag gac gtg gcg atg gcg cat gcc gac gcg cta gac gat ttc gat<br>Gly Glu Asp Val Ala Met Ala His Ala Asp Ala Leu Asp Asp Phe Asp<br>                  275                  280                285 | 864 |
| ctg gac atg ttg ggg gac ggg gat tcc ccg ggt ccg gga ttt acc ccc<br>Leu Asp Met Leu Gly Asp Gly Asp Ser Pro Gly Pro Gly Phe Thr Pro<br>                  290                  295                300 | 912 |
| cac gac tcc gcc ccc tac ggc gct ctg gat atg gcc gac ttc gag ttt<br>His Asp Ser Ala Pro Tyr Gly Ala Leu Asp Met Ala Asp Phe Glu Phe<br>305                  310                 315                320 | 960 |

```
gag cag atg ttt acc gat ccc ctt gga att gac gag tac ggt ggg      1005
Glu Gln Met Phe Thr Asp Pro Leu Gly Ile Asp Glu Tyr Gly Gly
            325                 330                 335 tag                                                              1008
```

<210> SEQ ID NO 2
<211> LENGTH: 335
<212> TYPE: PRT
<213> ORGANISM: Herpes Simplex Virus

<400> SEQUENCE: 2

```
Met Ser Arg Leu Asp Lys Ser Lys Val Ile Asn Ser Ala Leu Glu Leu
 1               5                  10                  15

Leu Asn Glu Val Gly Ile Glu Gly Leu Thr Thr Arg Lys Leu Ala Gln
             20                  25                  30

Lys Leu Gly Val Glu Gln Pro Thr Leu Tyr Trp His Val Lys Asn Lys
         35                  40                  45

Arg Ala Leu Leu Asp Ala Leu Ala Ile Glu Met Leu Asp Arg His His
     50                  55                  60

Thr His Phe Cys Pro Leu Glu Gly Glu Ser Trp Gln Asp Phe Leu Arg
 65                  70                  75                  80

Asn Lys Ala Lys Ser Phe Arg Cys Ala Leu Leu Ser His Arg Asp Gly
                 85                  90                  95

Ala Lys Val His Leu Gly Thr Arg Pro Thr Glu Lys Gln Tyr Glu Thr
            100                 105                 110

Leu Glu Asn Gln Leu Ala Phe Leu Cys Gln Gln Gly Phe Ser Leu Glu
        115                 120                 125

Asn Ala Leu Tyr Ala Leu Ser Ala Val Gly His Phe Thr Leu Gly Cys
    130                 135                 140

Val Leu Glu Asp Gln Glu His Gln Val Ala Lys Glu Glu Arg Glu Thr
145                 150                 155                 160

Pro Thr Thr Asp Ser Met Pro Pro Leu Leu Arg Gln Ala Ile Glu Leu
                165                 170                 175

Phe Asp His Gln Gly Ala Glu Pro Ala Phe Leu Phe Gly Leu Glu Leu
            180                 185                 190

Ile Ile Cys Gly Leu Glu Lys Gln Leu Lys Cys Glu Ser Gly Ser Ala
        195                 200                 205

Tyr Ser Arg Ala Arg Thr Lys Asn Asn Tyr Gly Ser Thr Ile Glu Gly
    210                 215                 220

Leu Leu Asp Leu Pro Asp Asp Ala Pro Glu Ala Gly Leu Ala
225                 230                 235                 240

Ala Pro Arg Leu Ser Phe Leu Pro Ala Gly His Thr Arg Arg Leu Ser
                245                 250                 255

Thr Ala Pro Pro Thr Asp Val Ser Leu Gly Asp Glu Leu His Leu Asp
            260                 265                 270

Gly Glu Asp Val Ala Met Ala His Ala Asp Ala Leu Asp Asp Phe Asp
        275                 280                 285

Leu Asp Met Leu Gly Asp Gly Asp Ser Pro Gly Pro Gly Phe Thr Pro
    290                 295                 300

His Asp Ser Ala Pro Tyr Gly Ala Leu Asp Met Ala Asp Phe Glu Phe
305                 310                 315                 320

Glu Gln Met Phe Thr Asp Pro Leu Gly Ile Asp Glu Tyr Gly Gly
                325                 330                 335
```

```
<210> SEQ ID NO 3
<211> LENGTH: 894
<212> TYPE: DNA
<213> ORGANISM: Herpes Simplex Virus
<220> FEATURE:
<221> NAME/KEY: CDS
<222> LOCATION: (1)...(891)
<220> FEATURE:
<221> NAME/KEY: exon
<222> LOCATION: (1)...(894)
<220> FEATURE:
<221> NAME/KEY: mRNA
<222> LOCATION: (1)...(894)
<220> FEATURE:
<221> NAME/KEY: misc_binding
<222> LOCATION: (1)...(207)
<220> FEATURE:
<221> NAME/KEY: misc_binding
<222> LOCATION: (208)...(297)

<400> SEQUENCE: 3
```

| | | | | | | | | | | | | | | | | |
|---|---|---|---|---|---|---|---|---|---|---|---|---|---|---|---|---|
| atg | tct | aga | tta | gat | aaa | agt | aaa | gtg | att | aac | agc | gca | tta | gag | ctg | 48 |
| Met | Ser | Arg | Leu | Asp | Lys | Ser | Lys | Val | Ile | Asn | Ser | Ala | Leu | Glu | Leu | |
| 1 | | | | 5 | | | | | 10 | | | | | 15 | | |
| ctt | aat | gag | gtc | gga | atc | gaa | ggt | tta | aca | acc | cgt | aaa | ctc | gcc | cag | 96 |
| Leu | Asn | Glu | Val | Gly | Ile | Glu | Gly | Leu | Thr | Thr | Arg | Lys | Leu | Ala | Gln | |
| | | | 20 | | | | | 25 | | | | | 30 | | | |
| aag | cta | ggt | gta | gag | cag | cct | aca | ttg | tat | tgg | cat | gta | aaa | aat | aag | 144 |
| Lys | Leu | Gly | Val | Glu | Gln | Pro | Thr | Leu | Tyr | Trp | His | Val | Lys | Asn | Lys | |
| | | 35 | | | | | 40 | | | | | 45 | | | | |
| cgg | gct | ttg | ctc | gac | gcc | tta | gcc | att | gag | atg | tta | gat | agg | cac | cat | 192 |
| Arg | Ala | Leu | Leu | Asp | Ala | Leu | Ala | Ile | Glu | Met | Leu | Asp | Arg | His | His | |
| | 50 | | | | | 55 | | | | | 60 | | | | | |
| act | cac | ttt | tgc | cct | tta | gaa | ggg | gaa | agc | tgg | caa | gat | ttt | tta | cgt | 240 |
| Thr | His | Phe | Cys | Pro | Leu | Glu | Gly | Glu | Ser | Trp | Gln | Asp | Phe | Leu | Arg | |
| 65 | | | | | 70 | | | | | 75 | | | | | 80 | |
| aat | aac | gct | aaa | agt | ttt | aga | tgt | gct | tta | cta | agt | cat | cgc | gat | gga | 288 |
| Asn | Asn | Ala | Lys | Ser | Phe | Arg | Cys | Ala | Leu | Leu | Ser | His | Arg | Asp | Gly | |
| | | | | 85 | | | | | 90 | | | | | 95 | | |
| gca | aaa | gta | cat | tta | ggt | aca | cgg | cct | aca | gaa | aaa | cag | tat | gaa | act | 336 |
| Ala | Lys | Val | His | Leu | Gly | Thr | Arg | Pro | Thr | Glu | Lys | Gln | Tyr | Glu | Thr | |
| | | | 100 | | | | | 105 | | | | | 110 | | | |
| ctc | gaa | aat | caa | tta | gcc | ttt | tta | tgc | caa | caa | ggt | ttt | tca | cta | gag | 384 |
| Leu | Glu | Asn | Gln | Leu | Ala | Phe | Leu | Cys | Gln | Gln | Gly | Phe | Ser | Leu | Glu | |
| | | 115 | | | | | 120 | | | | | 125 | | | | |
| aat | gca | tta | tat | gca | ctc | agc | gct | gtg | ggg | cat | ttt | act | tta | ggt | tgc | 432 |
| Asn | Ala | Leu | Tyr | Ala | Leu | Ser | Ala | Val | Gly | His | Phe | Thr | Leu | Gly | Cys | |
| | 130 | | | | | 135 | | | | | 140 | | | | | |
| gta | ttg | gaa | gat | caa | gag | cat | caa | gtc | gct | aaa | gaa | gaa | agg | gaa | aca | 480 |
| Val | Leu | Glu | Asp | Gln | Glu | His | Gln | Val | Ala | Lys | Glu | Glu | Arg | Glu | Thr | |
| 145 | | | | | 150 | | | | | 155 | | | | | 160 | |
| cct | act | act | gat | agt | atg | ccg | cca | tta | tta | cga | caa | gct | atc | gaa | tta | 528 |
| Pro | Thr | Thr | Asp | Ser | Met | Pro | Pro | Leu | Leu | Arg | Gln | Ala | Ile | Glu | Leu | |
| | | | | 165 | | | | | 170 | | | | | 175 | | |
| ttt | gat | cac | caa | ggt | gca | gag | cca | gcc | ttc | tta | ttc | ggc | ctt | gaa | ttg | 576 |
| Phe | Asp | His | Gln | Gly | Ala | Glu | Pro | Ala | Phe | Leu | Phe | Gly | Leu | Glu | Leu | |
| | | | 180 | | | | | 185 | | | | | 190 | | | |
| atc | ata | tgc | gga | tta | gaa | aaa | caa | ctt | aaa | tgt | gaa | agt | ggg | tct | gat | 624 |
| Ile | Ile | Cys | Gly | Leu | Glu | Lys | Gln | Leu | Lys | Cys | Glu | Ser | Gly | Ser | Asp | |
| | | 195 | | | | | 200 | | | | | 205 | | | | |
| cca | tcg | ata | cac | acg | cgc | aga | ctg | tcg | acg | gcc | ccc | cga | acc | gat | gtc | 672 |
| Pro | Ser | Ile | His | Thr | Arg | Arg | Leu | Ser | Thr | Ala | Pro | Pro | Thr | Asp | Val | |
| | 210 | | | | | 215 | | | | | 220 | | | | | |
| agc | ctg | ggg | gac | gag | ctc | cac | tta | gac | ggc | gag | gac | gtg | gcg | atg | gcg | 720 |

-continued

```
Ser Leu Gly Asp Glu Leu His Leu Asp Gly Glu Asp Val Ala Met Ala
225                 230                 235                 240 cat gcc gac gcg cta gac gat ttc gat ctg gac atg ttg ggg gac ggg      768
His Ala Asp Ala Leu Asp Asp Phe Asp Leu Asp Met Leu Gly Asp Gly
                245                 250                 255 gat tcc ccg ggt ccg gga ttt acc ccc cac gac tcc gcc ccc tac ggc      816
Asp Ser Pro Gly Pro Gly Phe Thr Pro His Asp Ser Ala Pro Tyr Gly
            260                 265                 270 gct ctg gat atg gcc gac ttc gag ttt gag cag atg ttt acc gat gcc      864
Ala Leu Asp Met Ala Asp Phe Glu Phe Glu Gln Met Phe Thr Asp Ala
        275                 280                 285 ctt gga att gac gag tac ggt ggg ttc tag                              894
Leu Gly Ile Asp Glu Tyr Gly Gly Phe
    290                 295
```

<210> SEQ ID NO 4
<211> LENGTH: 297
<212> TYPE: PRT
<213> ORGANISM: Herpes Simplex Virus

<400> SEQUENCE: 4

```
Met Ser Arg Leu Asp Lys Ser Lys Val Ile Asn Ser Ala Leu Glu Leu
1               5                   10                  15

Leu Asn Glu Val Gly Ile Glu Gly Leu Thr Thr Arg Lys Leu Ala Gln
            20                  25                  30

Lys Leu Gly Val Glu Gln Pro Thr Leu Tyr Trp His Val Lys Asn Lys
        35                  40                  45

Arg Ala Leu Leu Asp Ala Leu Ala Ile Glu Met Leu Asp Arg His His
    50                  55                  60

Thr His Phe Cys Pro Leu Glu Gly Glu Ser Trp Gln Asp Phe Leu Arg
65                  70                  75                  80

Asn Asn Ala Lys Ser Phe Arg Cys Ala Leu Leu Ser His Arg Asp Gly
                85                  90                  95

Ala Lys Val His Leu Gly Thr Arg Pro Thr Glu Lys Gln Tyr Glu Thr
            100                 105                 110

Leu Glu Asn Gln Leu Ala Phe Leu Cys Gln Gln Gly Phe Ser Leu Glu
        115                 120                 125

Asn Ala Leu Tyr Ala Leu Ser Ala Val Gly His Phe Thr Leu Gly Cys
    130                 135                 140

Val Leu Glu Asp Gln Glu His Gln Val Ala Lys Glu Glu Arg Glu Thr
145                 150                 155                 160

Pro Thr Thr Asp Ser Met Pro Pro Leu Leu Arg Gln Ala Ile Glu Leu
                165                 170                 175

Phe Asp His Gln Gly Ala Glu Pro Ala Phe Leu Phe Gly Leu Glu Leu
            180                 185                 190

Ile Ile Cys Gly Leu Glu Lys Gln Leu Lys Cys Glu Ser Gly Ser Asp
        195                 200                 205

Pro Ser Ile His Thr Arg Arg Leu Ser Thr Ala Pro Pro Thr Asp Val
    210                 215                 220

Ser Leu Gly Asp Glu Leu His Leu Asp Gly Glu Asp Val Ala Met Ala
225                 230                 235                 240

His Ala Asp Ala Leu Asp Asp Phe Asp Leu Asp Met Leu Gly Asp Gly
                245                 250                 255

Asp Ser Pro Gly Pro Gly Phe Thr Pro His Asp Ser Ala Pro Tyr Gly
            260                 265                 270

Ala Leu Asp Met Ala Asp Phe Glu Phe Glu Gln Met Phe Thr Asp Ala
```

```
                275                 280                 285
Leu Gly Ile Asp Glu Tyr Gly Gly Phe
    290                 295

<210> SEQ ID NO 5
<211> LENGTH: 450
<212> TYPE: DNA
<213> ORGANISM: Human cytomegalovirus
<220> FEATURE:
<221> NAME/KEY: mRNA
<222> LOCATION: (382)...(450)

<400> SEQUENCE: 5
gaattcctcg agtttaccac tccctatcag tgatagagaa aagtgaaagt cgagtttacc      60
actccctatc agtgatagag aaaagtgaaa gtcgagttta ccactcccta tcagtgatag    120
agaaaagtga agtcgagtt taccactccc tatcagtgat agagaaaagt gaaagtcgag    180
tttaccactc cctatcagtg atagagaaaa gtgaaagtcg agtttaccac tccctatcag    240
tgatagagaa aagtgaaagt cgagtttacc actccctatc agtgatagag aaaagtgaaa    300
gtcgagctcg gtacccgggt cgagtaggcg tgtacggtgg gaggcctata taagcagagc    360
tcgtttagtg aaccgtcaga tcgcctggag acgccatcca cgctgttttg acctccatag    420
aagacaccgg gaccgatcca gcctccgcgg                                      450

<210> SEQ ID NO 6
<211> LENGTH: 450
<212> TYPE: DNA
<213> ORGANISM: Human cytomegalovirus
<220> FEATURE:
<221> NAME/KEY: mRNA
<222> LOCATION: (382)...(450)

<400> SEQUENCE: 6
gaattcctcg acccgggtac cgagctcgac tttcactttt ctctatcact gatagggagt      60
ggtaaactcg actttcactt ttctctatca ctgatagggga gtggtaaact cgactttcac    120
ttttctctat cactgatagg gagtggtaaa ctcgactttc acttttctct atcactgata    180
gggagtggta aactcgactt tcactttttct ctatcactga tagggagtgg taaactcgac    240
tttcactttt ctctatcact gatagggagt ggtaaactcg actttcactt ttctctatca    300
ctgatagggga gtggtaaact cgagtaggcg tgtacggtgg gaggcctata taagcagagc    360
tcgtttagtg aaccgtcaga tcgcctggag acgccatcca cgctgttttg acctccatag    420
aagacaccgg gaccgatcca gcctccgcgg                                      450

<210> SEQ ID NO 7
<211> LENGTH: 398
<212> TYPE: DNA
<213> ORGANISM: Herpes Simplex Virus

<400> SEQUENCE: 7
gagctcgact ttcactttc tctatcactg atagggagtg gtaaactcga ctttcacttt       60
tctctatcac tgatagggag tggtaaactc gactttcact tttctctatc actgataggg    120
agtggtaaac tcgactttca cttttctcta tcactgatag ggagtggtaa actcgacttt    180
cactttctc tatcactgat agggagtggt aaactcgact ttcactttc tctatcactg    240
atagggagtg gtaaactcga ctttcacttt tctctatcac tgatagggag tggtaaactc    300
gagatccggc gaattcgaac acgcagatgc agtcggggcg cgcgggtccg aggtccactt    360
```

| | |
|---|---|
| cgcatattaa ggtgacgcgt gtggcctcga acaccgag | 398 |

<210> SEQ ID NO 8
<211> LENGTH: 6244
<212> TYPE: DNA
<213> ORGANISM: Herpes Simplex Virus

<400> SEQUENCE: 8

| | |
|---|---|
| ctcgagttta ccactcccta tcagtgatag agaaaagtga agtcgagtt taccactccc | 60 |
| tatcagtgat agagaaaagt gaaagtcgag tttaccactc cctatcagtg atagagaaaa | 120 |
| gtgaaagtcg agtttaccac tccctatcag tgatagagaa agtgaaagt cgagtttacc | 180 |
| actccctatc agtgatagag aaagtgaaa gtcgagttta ccactcccta tcagtgatag | 240 |
| agaaaagtga agtcgagtt taccactccc tatcagtgat agagaaaagt gaaagtcgag | 300 |
| ctcggtaccc gggtcgagta ggcgtgtacg gtgggaggcc tatataagca gagctcgttt | 360 |
| agtgaaccgt cagatcgcct ggagacgcca tccacgctgt tttgacctcc atagaagaca | 420 |
| ccgggaccga tccagcctcc gcggccccga attcgagctc ggtaccgggc cccccctcga | 480 |
| ggtcgacggt atcgataagc ttgatatcga attccaggag gtggagatcc gcgggtccag | 540 |
| ccaaacccca cacccatttt ctcctccctc tgccctata tcccggcacc cctcctcct | 600 |
| agcccttcc ctcctcccga gacgggggg aggagaaaag gggagttcag gtcgacatga | 660 |
| ctgagctgaa ggcaaaggaa cctcgggctc ccacgtggc gggcggcgcg cctcccccca | 720 |
| ccgaggtcgg atcccagctc ctgggtcgcc cggaccctgg cccttccag gggagccaga | 780 |
| cctcagaggc ctcgtctgta gtctccgcca tccccatctc cctggacggg ttgctcttcc | 840 |
| cccggccctg tcaggggcag aaccccccag acgggaagac gcaggaccca cgtcgttgt | 900 |
| cagacgtgga gggcgcattt cctggagtcg aagccccgga gggggcagga gacagcagct | 960 |
| cgagacctcc agaaaaggac agcggcctgc tggacagtgt cctcgacacg ctcctggcgc | 1020 |
| cctcgggtcc cgggcagagc acgccagcc ctgccacctg cgaggccatc agcccgtggt | 1080 |
| gcctgtttgg ccccgacctt cccgaagacc cccgggctgc ccccgctacc aaaggggtgt | 1140 |
| tggccccgct catgagccga cccgaggaca aggcaggcga cagctctggg acggcagcgg | 1200 |
| cccacaaggt gctgcccagg ggactgtcac catccaggca gctgctgctc ccctcctctg | 1260 |
| ggagccctca ctggccggca gtgaagccat ccccgcagcc cgctgcggtg caggtagacg | 1320 |
| aggaggacag ctccgaatcc gagggcaccg tgggcccgct cctgaagggc aacctcgggg | 1380 |
| cactgggagg cacggcggcc ggaggaggag ctgccccgt cgcgtctgga gcggccgcag | 1440 |
| gaggcgtcgc ccttgtcccc aaggaagatt ctcgcttctc ggcgcccagg gtctccttgg | 1500 |
| cggagcagga cgcgccggtg gcgcctgggc gctcccgct ggccacctcg gtggtggatt | 1560 |
| tcatccacgt gccatcctg cctctcaacc acgctttcct ggccaccgc accaggcagc | 1620 |
| tgctggaggg ggagagctac gacgcgggg ccgcggccgc cagcccttc gtcccgcagc | 1680 |
| ggggctcccc ctctgcctcg tccacccctg tggcgggcgg cgacttcccc gactgcacct | 1740 |
| acccgcccga cgccgagccc aaagatgacg cgttccccct tacgcgac ttccagccgc | 1800 |
| ccgccctcaa gataaggag gaggaagaag ccgccgaggc cgcggcgcgc tccccgcgta | 1860 |
| cgtacctggt ggctggtgca aacccgccg ccttcccgga cttccagctg gcagcgccgc | 1920 |
| cgccaccctc gctgccgcct cgagtgccct cgtccagacc cggggaagcg gcggtggcgg | 1980 |
| cctccccagg cagtgcctcc gtctcctcct cgtcctcgtc ggggtcgacc ctggagtgca | 2040 |
| tcctgtacaa ggcagaaggc gcgccgcccc agcagggccc cttcgcgccg ctgccctgca | 2100 |

```
agcctccggg cgccggcgcc tgcctgctcc cgcgggacgg cctgccctcc acctccgcct    2160
cgggcgcagc cgccggggcc gccctgcgc tctacccgac gctcggcctc aacggactcc     2220
cgcaactcgg ctaccaggcc gccgtgctca aggagggcct gccgcaggtc tacacgccct    2280
atctcaacta cctgaggccg gattcagaag ccagtcagag cccacagtac agcttcgagt    2340
cactacctca gaagatttgt ttgatctgtg gggatgaagc atcaggctgt cattatggtg    2400
tcctcacctg tgggagctgt aaggtcttct ttaaagggc aatggaaggg cagcataact     2460
atttatgtgc tggaagaaat gactgcattg ttgataaaat ccgcaggaaa aactgcccgg    2520
cgtgtcgcct tagaaagtgc tgtcaagctg gcatggtcct tggagggcga aagtttaaaa    2580
agttcaataa agtcagagtc atgagagcac tcgatgctgt tgctctccca cagccagtgg    2640
gcattccaaa tgaaagccaa cgaatcactt tttctccaag tcaagagata cagttaattc    2700
cccctctaat caacctgtta atgagcattg aaccagatgt gatctatgca ggacatgaca    2760
acacaaagcc tgatacctcc agttctttgc tgacgagtct taatcaacta ggcgagcggc    2820
aacttctttc agtggtaaaa tggtccaaat ctcttccagg ttttcgaaac ttacatattg    2880
atgaccagat aactctcatc cagtattctt ggatgagttt aatggtattt ggactaggat    2940
ggagatccta caaacatgtc agtgggcaga tgctgtattt tgcacctgat ctaatattaa    3000
atgaacagcg gatgaaagaa tcatcattct attcactatg ccttaccatg tggcagatac    3060
cgcaggagtt tgtcaagctt caagttagcc aagaagagtt cctctgcatg aaagtattac    3120
tacttcttaa tacaattcct ttggaaggac taagaagtca aagccagttt gaagagatga    3180
gatcaagcta cattagagag ctcatcaagg caattggttt gaggcaaaaa ggagttgttt    3240
ccagctcaca gcgtttctat cagctcacaa aacttcttga taacttgcat gatcttgtca    3300
aacaacttca cctgtactgc ctgaatacat ttatccagtc ccgggcgctg agtgttgaat    3360
ttccagaaat gatgtctgaa gttattgctg cacagttacc caagatattg gcagggatgg    3420
tgaaaccact tctctttcat aaaaagtgaa tgtcaattat ttttcaaaga attaagtgtt    3480
gtggtatgtc tttcgttttg gtcaggatta tgacgtctcg agtttttata atattctgaa    3540
agggaattcc tgcagcccgg gggatccact agttctagag gatccagaca tgataagata    3600
cattgatgag tttggacaaa ccacaactag aatgcagtga aaaaaatgct ttatttgtga    3660
aatttgtgat gctattgctt tatttgtaac cattataagc tgcaataaac aagttaacaa    3720
caacaattgc attcatttta tgtttcaggt tcaggggag tgtgtgggagg ttttttaaag    3780 caagtaaaac ctctacaaat gtggtatggc tgattatgat cctgcaagcc tcgtcgtctg    3840 gccgaccac gctatctgtg caaggtcccc ggacgcgcgc tccatgagca gagcgcccgc    3900
cgccgaggca agactcgggc ggcgccctgc ccgtcccacc aggtcaacag gcggtaaccg    3960
gcctcttcat cgggaatgcg cgcgaccttc agcatcgccg gcatgtcccc tggcggacgg    4020
gaagtatcag ctcgaccaag cttggcgaga ttttcaggag ctaaggaagc taaaatggag    4080
aaaaaaatca ctggatatac caccgttgat atatcccaat ggcatcgtaa agaacatttt    4140
gaggcatttc agtcagttgc tcaatgtacc tataaccaga ccgttcagct gcattaatga    4200
atcggccaac gcgcggggag aggcggtttg cgtattgggc gctcttccgc ttcctcgctc    4260
actgactcgc tgcgctcggt cgttcggctg cggcgagcgg tatcagctca ctcaaaggcg    4320
gtaatacggt tatccacaga atcaggggat aacgcaggaa agaacatgtg agcaaaaggc    4380
cagcaaaagg ccaggaaccg taaaaaggcc gcgttgctgg cgtttttcca taggctccgc    4440
```

-continued

```
cccccctgacg agcatcacaa aaatcgacgc tcaagtcaga ggtggcgaaa cccgacagga     4500
ctataaagat accaggcgtt tccccctgga agctccctcg tgcgctctcc tgttccgacc     4560
ctgccgctta ccggatacct gtccgccttt ctcccttcgg gaagcgtggc gctttctcaa     4620
tgctcacgct gtaggtatct cagttcggtg taggtcgttc gctccaagct gggctgtgtg     4680
cacgaacccc ccgttcagcc cgaccgctgc gccttatccg gtaactatcg tcttgagtcc     4740
aacccggtaa gacacgactt atcgccactg gcagcagcca ctggtaacag gattagcaga     4800
gcgaggtatg taggcggtgc tacagagttc ttgaagtggt ggcctaacta cggctacact     4860
agaaggacag tatttggtat ctgcgctctg ctgaagccag ttaccttcgg aaaaagagtt     4920
ggtagctctt gatccggcaa acaaaccacc gctggtagcg gtggtttttt tgtttgcaag     4980
cagcagatta cgcgcagaaa aaaggatct caagaagatc ctttgatctt ttctacgggg      5040
tctgacgctc agtggaacga aaactcacgt taagggattt tggtcatgag attatcaaaa     5100
aggatcttca cctagatcct tttaaattaa aaatgaagtt ttaaatcaat ctaaagtata     5160
tatgagtaaa cttggtctga cagttaccaa tgcttaatca gtgaggcacc tatctcagcg     5220
atctgtctat ttcgttcatc catagttgcc tgactcccg tcgtgtagat aactacgata      5280
cgggagggct taccatctgg ccccagtgct gcaatgatac cgcgagaccc acgctcaccg     5340
gctccagatt tatcagcaat aaaccagcca gccggaaggg ccgagcgcag aagtggtcct     5400
gcaactttat ccgcctccat ccagtctatt aattgttgcc gggaagctag agtaagtagt     5460
tcgccagtta atagtttgcg caacgttgtt gccattgcta caggcatcgt ggtgtcacgc     5520
tcgtcgtttg gtatggcttc attcagctcc ggttcccaac gatcaaggcg agttacatga     5580
tcccccatgt tgtgcaaaaa agcggttagc tccttcggtc ctccgatcgt tgtcagaagt     5640
aagttggccg cagtgttatc actcatggtt atggcagcac tgcataattc tcttactgtc     5700
atgccatccg taagatgctt ttctgtgact ggtgagtact caaccaagtc attctgagaa     5760
tagtgtatgc ggcgaccgag ttgctcttgc ccggcgtcaa tacgggataa taccgcgcca     5820
catagcagaa ctttaaaagt gctcatcatt ggaaaacgtt cttcggggcg aaaactctca     5880
aggatcttac cgctgttgag atccagttcg atgtaaccca ctcgtgcacc caactgatct     5940
tcagcatctt ttactttcac cagcgtttct gggtgagcaa aaacaggaag caaaatgcc      6000
gcaaaaaagg gaataagggc gacacggaaa tgttgaatac tcatactctt ccttttcaa      6060
tattattgaa gcatttatca gggttattgt ctcatgagcg gatacatatt tgaatgtatt     6120
tagaaaaata aacaaatagg ggttccgcgc acatttcccc gaaaagtgcc acctgacgtc     6180
taagaaacca ttattatcat gacattaacc tataaaaata ggcgtatcac gaggcccttt     6240
cgtc                                                                  6244
```

<210> SEQ ID NO 9
<211> LENGTH: 4963
<212> TYPE: DNA
<213> ORGANISM: Herpes Simplex Virus

<400> SEQUENCE: 9

```
ctcgagttta ccactcccta tcagtgatag agaaaagtga agtcgagtt taccactccc       60
tatcagtgat agagaaaagt gaaagtcgag tttaccactc cctatcagtg atagagaaaa     120
gtgaaagtcg agtttaccac tccctatcag tgatagagaa aagtgaaagt cgagtttacc     180
actccctatc agtgatagag aaaagtgaaa gtcgagttta ccactcccta tcagtgatag     240
agaaaagtga agtcgagtt taccactccc tatcagtgat agagaaaagt gaaagtcgag     300
```

```
ctcggtaccc gggtcgagta ggcgtgtacg gtgggaggcc tatataagca gagctcgttt    360
agtgaaccgt cagatcgcct ggagacgcca tccacgctgt tttgacctcc atagaagaca    420
ccgggaccga tccagcctcc gcggccccga attccggcca cgaccatgac catgaccctc    480
cacaccaaag catctgggat ggccctactg catcagatcc aagggaacga gctggagccc    540
ctgaaccgtc cgcagctcaa gatcccsctg gagcggcccc tgggcgaggt gtacctggac    600
agcagcaagc ccgccgtgta caactacccc gagggcgccg cctacgagtt caacgccgcg    660
gccgccgcca cgcgcaggt ctacggtcag accggcctcc cctacggccc cgggtctgag    720
gctgcggcgt tcggctccaa cggcctgggg ggtttccccc cactcaacag cgtgtctccg    780
agcccgctga tgctactgca cccgccgccg cagctgtcgc ctttcctgca gccccacggc    840
cagcaggtgc cctactacct ggagaacgag cccagcggct acacggtgcg cgaggccggc    900
ccgccggcat tctacaggcc aaattcagat aatcgacgcc agggtggcag agaaagattg    960
gccagtacca atgacaaggg aagtatggct atggaatctg ccaaggagac tcgctactgt   1020
gcagtgtgca atgactatgc ttcaggctac cattatggag tctggtcctg tgagggctgc   1080
aaggccttct tcaagagaag tattcaagga cataacgact atatgtgtcc agccaccaac   1140
cagtgcacca ttgataaaaa caggaggaag agctgccagg cctgccggct ccgcaaatgc   1200
tacgaagtgg gaatgatgaa aggtgggata cgaaaagacc gaagaggagg gagaatgttg   1260
aaacacaagc gccagagaga tgatgggag gcaggggtg aagtgggtc tgctggagac    1320 atgagagctg ccaacctttg gccaagcccg ctcatgatca aacgctctaa gaagaacagc   1380
ctggccttgt ccctgacggc cgaccagatg gtcatggcct tgttggatgc tgagccccc   1440 atactctatt ccgagtatga tcctaccaga cccttcagtg aagcttcgat gatgggctta   1500
ctgaccaacc tggcagacag ggagctggtt cacatgatca actgggcgaa gagggtgcca   1560
ggctttgtgg atttgaccct ccatgatcag gtccaccttc tagaatgtgc ctggctagag   1620
atcctgatga ttggtctcgt ctggcgctcc atggagcacc cagtgaagct actgtttgct   1680
cctaacttgc tcttggacag gaaccaggga aaatgtgtag agggcatggt ggagatcttc   1740
gacatgctgc tggctacatc atctcggttc cgcatgatga atctgcaggg agaggagttt   1800
gtgtgcctca aatctattat tttgcttaat tctggagtgt acacatttct gtccagcacc   1860
ctgaagtctc tggaagagaa ggaccatatc caccgagtcc tggacaagat cacagacact   1920
ttgatccacc tgatggccaa ggcaggcctg acctgcagc agcagcacca gcggctggcc   1980
cagctcctcc tcatcctctc ccacatcagg cacatgagta acaaaggcat ggagcatctg   2040
tacagcatga agtgcaagaa cgtggtgccc ctctatgacc tgctgctgga gatgctggac   2100
gcccaccgcc tacatgcgcc cactagccgt ggagggcat ccgtggagga gacggaccaa   2160
agccacttgg ccactgcggg ctctacttca tcgcattcct tgcaaaagta ttacatcacg   2220
ggggaggcag agggtttccc tgccacagtc tgagagctcc ctggcggaat tcgagctcgg   2280
tacccgggga tcctctagag gatccagaca tgataagata cattgatgag tttggacaaa   2340
ccacaactag aatgcagtga aaaaaatgct ttatttgtga aatttgtgat gctattgctt   2400
tatttgtaac cattataagc tgcaataaac aagttaacaa caacaattgc attcatttta   2460
tgtttcaggt tcaggggag gtgtgggagg ttttttaaag caagtaaaac ctctacaaat   2520
gtggtatggc tgattatgat cctgcaagcc tcgtcgtctg gccggaccac gctatctgtg   2580
caaggtcccc ggacgcgcgc tccatgagca gagcgcccgc cgccgaggca agactcgggc   2640
```

```
ggcgccctgc cgtcccacc aggtcaacag gcggtaaccg gcctcttcat cgggaatgcg    2700
cgcgaccttc agcatcgccg gcatgtcccc tggcggacgg gaagtatcag ctcgaccaag    2760
cttggcgaga ttttcaggag ctaaggaagc taaaatggag aaaaaaatca ctggatatac    2820
caccgttgat atatcccaat ggcatcgtaa agaacatttt gaggcatttc agtcagttgc    2880
tcaatgtacc tataaccaga ccgttcagct gcattaatga atcggccaac gcgcggggag    2940
aggcggtttg cgtattgggc gctcttccgc ttcctcgctc actgactcgc tgcgctcggt    3000
cgttcggctg cggcgagcgg tatcagctca ctcaaaggcg gtaatacggt tatccacaga    3060
atcaggggat aacgcaggaa agaacatgtg agcaaaaggc cagcaaaagg ccaggaaccg    3120
taaaaaggcc gcgttgctgg cgttttccca taggctccgc cccctgacg agcatcacaa    3180
aaatcgacgc tcaagtcaga ggtggcgaaa cccgacagga ctataaagat accaggcgtt    3240
tccccctgga agctccctcg tgcgctctcc tgttccgacc ctgccgctta ccggatacct    3300
gtccgccttt ctcccttcgg gaagcgtggc gctttctcaa tgctcacgct gtaggtatct    3360
cagttcggtg taggtcgttc gctccaagct gggctgtgtg cacgaacccc ccgttcagcc    3420
cgaccgctgc gccttatccg gtaactatcg tcttgagtcc aacccggtaa gacacgactt    3480
atcgccactg gcagcagcca ctggtaacag gattagcaga gcgaggtatg taggcggtgc    3540
tacagagttc ttgaagtggt ggcctaacta cggctacact agaaggacag tatttggtat    3600
ctgcgctctg ctgaagccag ttaccttcgg aaaaagagtt ggtagctctt gatccggcaa    3660
acaaaccacc gctggtagcg gtggtttttt tgtttgcaag cagcagatta cgcgcagaaa    3720
aaaaggatct caagaagatc ctttgatctt ttctacgggg tctgacgctc agtggaacga    3780
aaactcacgt taagggattt tggtcatgag attatcaaaa aggatcttca cctagatcct    3840
tttaaattaa aaatgaagtt ttaaatcaat ctaaagtata tatgagtaaa cttggtctga    3900
cagttaccaa tgcttaatca gtgaggcacc tatctcagcg atctgtctat ttcgttcatc    3960
catagttgcc tgatccccgt cgtgtagata actacgatac gggagggctt accatctggc    4020
cccagtgctg caatgatacc gcgagaccca cgctcaccgg ctccagattt atcagcaata    4080
aaccagccag ccggaagggc cgagcgcaga agtggtcctg caactttatc cgcctccatc    4140
cagtctatta attgttgccg ggaagctaga gtaagtagtt cgccagttaa tagtttgcgc    4200
aacgttgttg ccattgctac aggcatcgtg gtgtcacgct cgtcgtttgg tatggcttca    4260
ttcagctccg gttcccaacg atcaaggcga gttacatgat cccccatgtt gtgcaaaaaa    4320
gcggttagct ccttcggtcc tccgatcgtt gtcagaagta agttggccgc agtgttatca    4380
ctcatggtta tggcagcact gcataattct cttactgtca tgccatccgt aagatgcttt    4440
tctgtgactg gtgagtactc aaccaagtca ttctgagaat agtgtatgcg gcgaccgagt    4500
tgctcttgcc cggcgtcaat acgggataat accgcgccac atagcagaac tttaaaagtg    4560
ctcatcattg gaaaacgttc ttcggggcga aaactctcaa ggatcttacc gctgttgaga    4620
tccagttcga tgtaacccac tcgtgcaccc aactgatctt cagcatcttt tactttcacc    4680
agcgtttctg ggtgagcaaa aacaggaagg caaaatgccg caaaaaaggg aataagggcg    4740
acacggaaat gttgaatact catactcttc ctttttcaat attattgaag catttatcag    4800
ggttattgtc tcatgagcgg atacatattt gaatgtattt agaaaaataa acaaataggg    4860
gttccgcgca catttccccg aaaagtgcca cctgacgtct aagaaaccat tattatcatg    4920
acattaacct ataaaaatag gcgtatcacg aggccctttc gtc                     4963
```

```
<210> SEQ ID NO 10
<211> LENGTH: 42
<212> TYPE: DNA
<213> ORGANISM: Herpes Simplex Virus

<400> SEQUENCE: 10
tcgagtttac cactccctat cagtgataga gaaaagtgaa ag          42

<210> SEQ ID NO 11
<211> LENGTH: 6
<212> TYPE: PRT
<213> ORGANISM: Artificial Sequence
<220> FEATURE:
<223> OTHER INFORMATION: linker peptides

<400> SEQUENCE: 11

Ser Gly Ser Ala Tyr Ser
 1               5

<210> SEQ ID NO 12
<211> LENGTH: 10
<212> TYPE: PRT
<213> ORGANISM: Artificial Sequence
<220> FEATURE:
<223> OTHER INFORMATION: linker peptides

<400> SEQUENCE: 12

Ser Gly Ser Asp Pro Ser Ile His Thr Arg
 1               5                  10

<210> SEQ ID NO 13
<211> LENGTH: 4
<212> TYPE: PRT
<213> ORGANISM: Artificial Sequence
<220> FEATURE:
<223> OTHER INFORMATION: linker peptides

<400> SEQUENCE: 13

Tyr Gly Gly Phe
 1

<210> SEQ ID NO 14
<211> LENGTH: 19
<212> TYPE: DNA
<213> ORGANISM: Artificial Sequence
<220> FEATURE:
<223> OTHER INFORMATION: linker nucleotides

<400> SEQUENCE: 14
tccctatcag tgatagaga                                    19

<210> SEQ ID NO 15
<211> LENGTH: 12
<212> TYPE: DNA
<213> ORGANISM: Artificial Sequence
<220> FEATURE:
<223> OTHER INFORMATION: Linker nucleotides

<400> SEQUENCE: 15
aggcctatat aa                                           12

<210> SEQ ID NO 16
<211> LENGTH: 6
<212> TYPE: DNA
<213> ORGANISM: Artificial Sequence
<220> FEATURE:
<223> OTHER INFORMATION: linker nucleotides
```

```
<400> SEQUENCE: 16 ctcgag                                                                  6

<210> SEQ ID NO 17
<211> LENGTH: 19
<212> TYPE: DNA
<213> ORGANISM: Artificial Sequence
<220> FEATURE:
<223> OTHER INFORMATION: linker nucleotides

<400> SEQUENCE: 17
tctctatcac tgataggga                                                   19
```